US011690938B2

(12) United States Patent
Fitzgerald et al.

(10) Patent No.: US 11,690,938 B2
(45) Date of Patent: Jul. 4, 2023

(54) SURGICAL SYSTEM AND METHOD OF USE

(71) Applicants: Alfred Health, Melbourne (AU);
Monash University, Clayton (AU)

(72) Inventors: Mark Fitzgerald, Melbourne (AU);
Peter Finnegan, Melbourne (AU);
Wing Chiu, Clayton (AU); Nayeem Chowdhury, Clayton (AU); Nabil Chowdhury, Clayton (AU)

(73) Assignees: Alfred Health, Melbourne (AU);
Monash University, Clayton (AU)

( * ) Notice: Subject to any disclaimer, the term of this patent is extended or adjusted under 35 U.S.C. 154(b) by 960 days.

(21) Appl. No.: 16/462,910

(22) PCT Filed: Nov. 22, 2017

(86) PCT No.: PCT/AU2017/051286
§ 371 (c)(1),
(2) Date: May 21, 2019

(87) PCT Pub. No.: WO2018/094458
PCT Pub. Date: May 31, 2018

(65) Prior Publication Data
US 2019/0307937 A1    Oct. 10, 2019

(30) Foreign Application Priority Data

Nov. 22, 2016  (AU) ................ 2016904770

(51) Int. Cl.
*A61M 1/04* (2006.01)
*A61B 17/34* (2006.01)
*A61B 17/00* (2006.01)

(52) U.S. Cl.
CPC .......... *A61M 1/04* (2013.01); *A61B 17/3403* (2013.01); *A61B 17/3421* (2013.01);
(Continued)

(58) Field of Classification Search
CPC ................ A61M 1/04; A61B 17/3496; A61B 2017/00455; A61B 2017/3407;
(Continued)

(56) References Cited

U.S. PATENT DOCUMENTS 5,334,164 A  *  8/1994  Guy ................... A61M 39/06
                                                  604/246
5,385,552 A      1/1995  Haber et al.
(Continued)

FOREIGN PATENT DOCUMENTS

EP    1204381 B1    11/2005
EP    1599143 B1    1/2014

OTHER PUBLICATIONS

Bowness, J., Kilgour, P. M., Whiten, S., Parkin, I., Mooney, J., & Driscoll, P. (2015). Guidelines for chest drain insertion may not prevent damage to abdominal viscera. Emergency Medicine Journal : EMJ, 32(8), 620. doi:http://dx.doi.org/10.1136/emermed-2014-203689 (Year: 2015).*

(Continued)

*Primary Examiner* — Darwin P Erezo
*Assistant Examiner* — Brigid K Byrd
(74) *Attorney, Agent, or Firm* — Kilpatrick Townsend & Stockton LLP

(57) ABSTRACT

A surgical system for use in establishing and maintaining an opening to an anatomical space of a body, the system comprising an obturator assembly having a cutting portion at a distal end and a cannula, the cannula being detachably coupled to the cutting portion and deployable into the anatomical space of a patient, the cannula comprises a locking portion, and a lengthwise extendable body; a valve assembly comprising a passage for receiving the cannula, a first end for coupling to a fluid extraction device and a second end for placement external and adjacent the ana- (Continued)

tomical space; a base comprising a plate for placement on a patient external and adjacent the anatomical space, the plate has an aperture configured for receiving the obturator assembly and coupling means located about the aperture for coupling with the valve assembly; and wherein, in use, the locking portion of the cannula is configured to be retained in the valve assembly with the extendable body extended into the anatomical space to facilitate a path for fluid extraction, and wherein the cannula comprises means for retaining the cannula in its extended state.

24 Claims, 50 Drawing Sheets

(52) U.S. Cl.
CPC ...... *A61B 17/3462* (2013.01); *A61B 17/3496* (2013.01); *A61B 17/3474* (2013.01); *A61B 2017/00455* (2013.01); *A61B 2017/3407* (2013.01); *A61B 2017/349* (2013.01); *A61B 2017/3427* (2013.01); *A61B 2017/3443* (2013.01); *A61B 2017/3488* (2013.01)

(58) Field of Classification Search
CPC .... A61B 2017/3427; A61B 2017/3443; A61B 2017/3488; A61B 2017/349; A61B 17/3498; A61B 17/348–3492
See application file for complete search history.

(56) References Cited

U.S. PATENT DOCUMENTS

| | | | | |
|---|---|---|---|---|
| 5,591,191 | A | * | 1/1997 | Kieturakis ......... A61B 17/3417 604/164.01 |
| 5,807,338 | A | * | 9/1998 | Smith ................ A61B 17/3417 606/167 |
| 2002/0052610 | A1 | * | 5/2002 | Skakoon ................ A61B 34/20 606/129 |
| 2004/0049157 | A1 | * | 3/2004 | Plishka .............. A61B 17/3415 604/167.03 |
| 2005/0234390 | A1 | | 10/2005 | Buckman et al. |
| 2006/0200185 | A1 | * | 9/2006 | Marchek ............ A61B 17/3421 606/191 |
| 2007/0005087 | A1 | | 1/2007 | Smith et al. |
| 2008/0086075 | A1 | | 4/2008 | Isik et al. |
| 2009/0209971 | A1 | * | 8/2009 | Tanaka .................... A61M 1/04 606/108 |
| 2010/0324488 | A1 | | 12/2010 | Smith |

OTHER PUBLICATIONS

International Search Report and Written Opinion dated Feb. 13, 2018 in International Patent Application No. PCT/AU2017/051286.

* cited by examiner

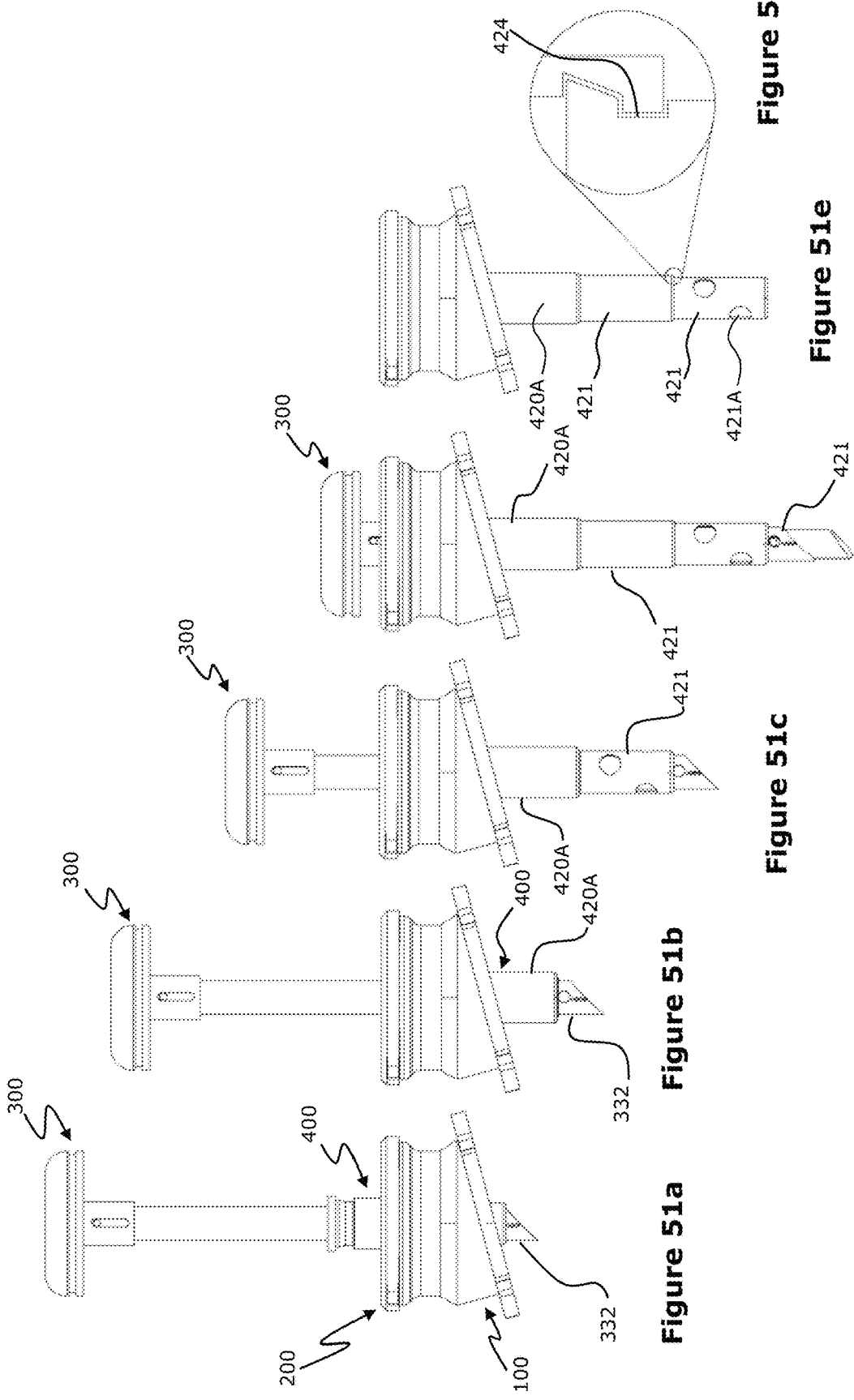

SURGICAL SYSTEM AND METHOD OF USE

The entire content of Australian Provisional Patent Application No. 2016904770 as originally filed is incorporated herein by reference.

FIELD OF THE INVENTION

The invention relates to a surgical system and method for establishing and maintaining a percutaneous cannula into an anatomical space such as a body cavity to permit controlled passage of fluid, and more particularly to a pleural decompression system and method for use in the treatment of simple and tension pneumothorax.

BACKGROUND OF THE INVENTION

Tension pneumothorax (TP) is a life-threatening condition occurring in 1-3% of major trauma patients who have sustained penetrating or blunt chest trauma including blast injury. It is associated with hypoxia in 50% of spontaneously breathing trauma patients and respiratory arrest in 9.3% of the patients. TP has been identified as the cause of death in 3-4% of fatally wounded combat casualties and is responsible for 33% of preventable deaths on the battlefield.

Decompressing the pleural space and venting air or blood is the definitive emergency intervention for tension pneumothorax and failure to decompress a tension pneumothorax is a well-recognized cause of avoidable, early trauma death. Needle Thoracostomy (NT) is a technique currently recommended as the emergency intervention for achieving rapid pleural decompression. The conventional NT method involves the use of a decompression needle (see FIG. 1) for piercing through the chest of a patient to access and extract fluid build-up in the pleural space (see FIG. 2).

However, the conventional NT method has a high risk of failure attributable to several factors including improper needle placement and inappropriate catheter length. It is understood that deficient needle length for effective pleural decompression may relate to increased anterior Chest Wall Thickness (CWT) of military personnel. Potential solutions thus far have been two-fold; using a longer catheter and considering other sites of access. However inter-population difference in CWT means that the "one-length NT fits all" approach is flawed and the variable length approach is logistically complicated for a field operator to determine and deploy under stress.

The applicant has determined that it would be advantageous to provide an improved, easy to use surgical system and method that is suitable for use in the treatment of simple and tension pneumothorax despite inter-population differences in CWT. The present invention seeks to at least in part alleviate the problems identified above.

SUMMARY OF THE INVENTION

According to an aspect of the present invention, there is provided a surgical system for use in establishing and maintaining an opening to an anatomical space of a body, the system comprising: an obturator assembly having a cutting portion at a distal end and a cannula, the cannula being detachably coupled to the cutting portion and deployable into the anatomical space of a patient, the cannula comprises a locking portion, and a lengthwise extendable body; a valve assembly comprising a passage for receiving the cannula, a first end for coupling to a fluid extraction device and a second end for placement external and adjacent the anatomical space; a base comprising a plate for placement on a patient external and adjacent the anatomical space, the plate has an aperture configured for receiving the obturator assembly and coupling means located about the aperture for coupling with the valve assembly; and wherein, in use, the locking portion of the cannula is configured to be retained in the valve assembly with the extendable body extended into the anatomical space to facilitate a path for fluid extraction, and wherein the cannula comprises means for retaining the cannula in its extended state.

According to another aspect of the present invention, there is provided a pleural decompression system for use in the treatment of simple and/or tension pneumothorax, the system comprising: an obturator assembly having a cutting portion at a distal end and a cannula, the cannula being detachably coupled to the cutting portion and deployable into a pleural space of a patient, the cannula comprises a locking portion, and a lengthwise extendable body; a valve assembly comprising a passage for receiving the cannula, a first end for coupling to a fluid extraction device and a second end for placement above an intercostal space; a base comprising a plate for placement on a patient above an intercostal space, the plate has an aperture configured for receiving the obturator assembly and coupling means located about the aperture for coupling with the valve assembly; and wherein, in use, the locking portion of the cannula is configured to be retained in the valve assembly with the extendable body extended into the chest wall of the patient to facilitate a path for pleural fluid extraction, and wherein the cannula comprises means for retaining the cannula in its extended state.

According to another aspect of the invention, the surgical system is provided for use in the treatment of simple and/or tension pneumothorax.

Preferably, the cannula is configured to have a minimum length of about 4 cm and a maximum length of about 9 cm.

Preferably, a coiled spring is mounted around the cannula body to provide a bias around the body to move towards an extended configuration.

Preferably, the means for retaining the cannula in its extended state comprises an anchoring portion located at a distal end of the cannula. Preferably, the anchoring portion is in the form of a helical flange. Preferably, the helical flange is operable between an anchoring configuration in which the flange is collapsed in the longitudinal direction, and an extraction configuration in which the flange is extended in the longitudinal direction.

Alternatively, the cannula comprises two or more telescopic sections extendable from the cannula body. Preferably, the means for retaining the cannula in its extended state comprises locking means for locking each telescopic section in its extended state when the cannula is in an extended state.

Preferably, the coupling means is configured to receive the valve assembly at an angle inclined to an axis perpendicular to the plane of the plate.

Preferably, an underside of the plate is provided with adhesive means for securing the plate to the patient. Preferably, the adhesive means is foam-backed adhesive.

Preferably, the system further comprises an indicator extending from the plate for assisting a user with placement of the plate above the intercostal space.

Preferably, the system further comprises side portions extending in opposite directions from the plate for stabilising the plate from movement when applied to the torso.

Preferably, the system further comprises an electrode embedded in the plate configured for outputting cardiac spatial data to an external monitoring device.

Preferably, the valve assembly comprises a one-way efflux valve.

Preferably, the first end of the valve is configured to receive a cap for coupling with a fluid extracting device.

Preferably, the obturator assembly comprises a hollow stem and the cutting portion being located at the distal end of the stem.

Preferably, the obturator assembly further comprises a spring-loaded inner stylet housed within the stem and movable relative to the stem, the stylet having a handle located at a proximate end and a blunt portion located at a distal end of the stem, wherein the obturator assembly is configured to operate between a retracted cutting configuration in which the blunt portion of the stylet is received within the stem to expose the cutting portion and an extended configuration in which the blunt portion extends past the cutting portion.

Preferably, the obturator assembly is configured with locking means to hold the stem and stylet in the cutting and extended configurations.

Preferably, the locking means comprises one or more complementary protrusion and aperture formations on the stem and the stylet.

Preferably, the obturator assembly transforms from the cutting configuration to the extended configuration by a user pushing the stylet handle such that the blunt portion extends past the cutting portion and the locking means engages the stylet in the extended configuration.

Preferably, the cutting portion comprises a cutting blade having a chamfered tip.

According to another aspect of the invention, there is provided a method of establishing and maintaining an opening to an anatomical space of a body, the method comprising the steps of: affixing a base comprising a plate on a patient external and adjacent the anatomical space of the patient, the plate having an aperture configured for receiving an obturator assembly and coupling means located about the aperture for coupling with a valve assembly; coupling the valve assembly to the base, the valve assembly comprising a passage for receiving the cannula and an open end for coupling to a fluid extraction device; cutting through muscular tissues into the anatomical space with a cutting portion of the obturator assembly by inserting the obturator assembly through the valve assembly passage and the plate aperture, and pushing a handle of the obturator assembly so that the cutting portion cuts through the tissues, a blunt portion of the obturator assembly automatically extends past the cutting portion with a loss of cutting pressure and locks the blunt portion relative to the cutting portion to prevent visceral organ injury; deploying a cannula into the anatomical space from the obturator assembly by securing a locking portion of the cannula to the valve assembly and removing the obturator assembly, the cannula further comprises a lengthwise extendable body extendable into an anatomical part of the patient to facilitate a path for fluid extraction into the valve assembly, the cannula having means for retaining the cannula in its extended state in use; extracting fluid from the anatomical space by coupling the fluid extraction device to the valve assembly.

According to another aspect of the invention, there is provided a method of extracting fluid from a pleural cavity of a patient using a pleural decompression system in the treatment of simple and/or tension pneumothorax, the method comprising the steps of: affixing a base comprising a plate on a patient above an intercostal space of the pleural cavity, the plate having an aperture configured for receiving an obturator assembly and coupling means located about the aperture for coupling with a valve assembly; coupling the valve assembly to the base, the valve assembly comprising a passage for receiving the cannula and an open end for coupling to a fluid extraction device; cutting through muscular tissues into the pleural cavity with a cutting portion of the obturator assembly by inserting the obturator assembly through the valve assembly passage and the plate aperture, and pushing a handle of the obturator assembly so that the cutting portion cuts through the tissues, a blunt portion of the obturator assembly automatically extends past the cutting portion with a loss of cutting pressure and locks the blunt portion relative to the cutting portion to prevent visceral organ injury; deploying a cannula into the pleural cavity from the obturator assembly by securing a locking portion of the cannula to the valve assembly and removing the obturator assembly, the cannula further comprises a lengthwise extendable body extendable into the chest wall of the patient to facilitate a path for pleural fluid extraction into the valve assembly, the cannula having means for retaining the cannula in its extended state in use; extracting fluid from the pleural cavity by coupling the fluid extraction device to the valve assembly.

Preferably, the cannula is configured to have a minimum length of about 4 cm and a maximum length of about 9 cm.

Preferably, a coiled spring is mounted around the cannula body to provide a bias around the body to move towards an extended configuration.

Preferably, the cannula comprises two or more telescopic sections extendable from the cannula body.

Preferably, the method further comprises the step of: locating a mid-point of an upper arm of a supine-positioned patient between the olecranon and the acromion when the elbow of the patient is flexed to 90 degrees with the patient's forearm in a mid prone position; projecting a line, perpendicular to the upper arm, from the mid-point of the upper arm across to the torso of the patient; and marking the area of contact between the projecting line and the torso as a safe zone for performing pleural decompression.

According to another aspect of the invention, there is provided a base which, in use, receives an obturator assembly for establishing and maintaining an opening to an anatomical space of a body, the base comprising a plate for placement on a patient external and adjacent the anatomical space, the plate having an aperture configured to receive the obturator assembly.

According to another aspect of the invention, there is provided a base which, in use, receives an obturator assembly for the treatment of simple and/or tension pneumothorax, comprising a plate for placement on a patient above an intercostal space, the plate having an aperture configured to receive the obturator assembly.

Preferably, an underside of the plate is provided with adhesive means for securing the plate to the patient. Preferably, the adhesive means is foam-backed adhesive.

Preferably, the base further comprises an indicator extending from the plate for assisting a user with placement of the plate external and adjacent or above the anatomical or intercostal space.

Preferably, the plate further comprises coupling means located about the aperture for receiving a valve assembly operable to seal the aperture in use.

Preferably, the coupling means is configured to receive the valve assembly at an angle oblique to an axis perpendicular to the plane of the plate.

Preferably, the base further comprises side portions extending in opposite directions from the plate for stabilising the plate from movement when applied to the torso.

Preferably, the base further comprises an electrode embedded in the plate configured for outputting cardiac spatial data to an external monitoring device.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Throughout this specification and the claims which follow, unless the context requires otherwise, the term "fluid" would be understood to include gaseous fluids such as air as well as liquid fluids such as blood and other bodily fluids.

BRIEF DESCRIPTION OF THE DRAWINGS

Further aspects of the present invention and further embodiments of the aspects described in the preceding paragraphs will become apparent from the following description. The invention will now be described, by way of example only, with reference to the accompanying drawings, in which:

FIG. 51 show a series of rendered side views of the obturator assembly of FIG. 50 in use with a telescopic cannula.

DETAILED DESCRIPTION

Figure 1:
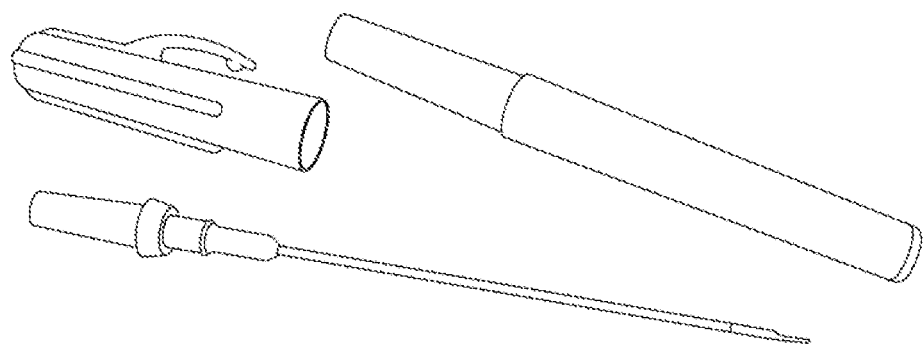
FIG. 1 is a photograph showing conventional Needle Thoracostomy (NT) device.
Figure 2:
FIG. 2 is a photograph showing a field use of a conventional NT device for treating tension pneumothorax.
Figure 3A:
FIGS. 3A to 3D are photographs showing the positioning of a patient for locating a pleural cavity in accordance with an embodiment of the invention.
Figure 3B:
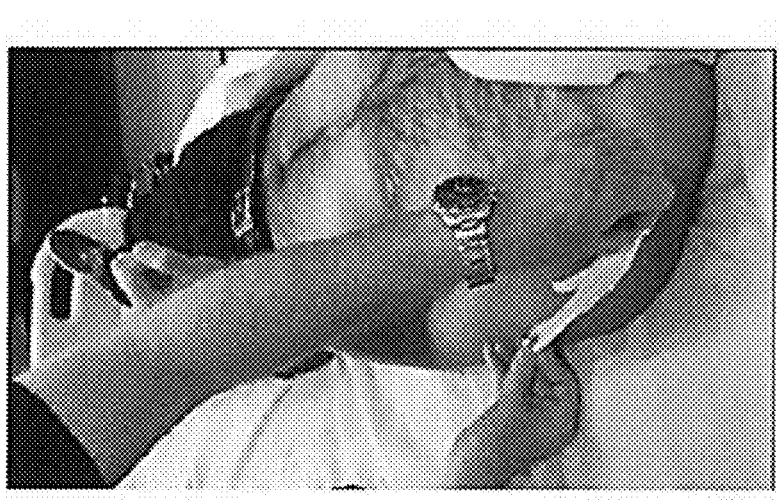
Figure 3C:
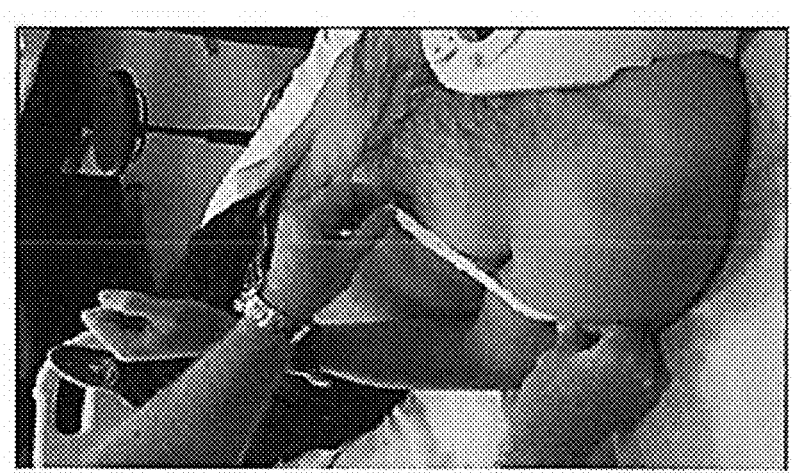
Figure 3D:
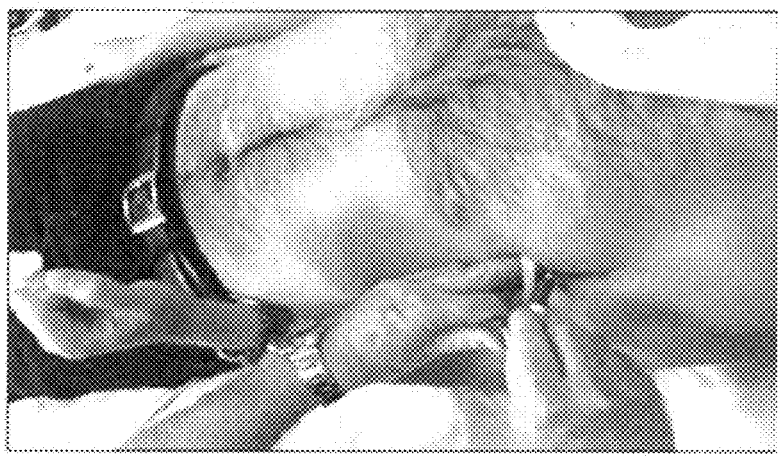

FIGS. 1 and 2 show a conventional Needle Thoracostomy (NT) device and its use in the field for treating tension pneumothorax. It can be seen that the conventional NT device comprises a fixed-length needle and catheter which is administered directly over a patient above an intercostal space for relieving pleural fluid for treating tension pneumothorax.

Preferred embodiments of the present invention seek to provide easy to use surgical pleural decompression devices and systems for the treatment of simple and tension pneumothorax despite inter-population differences in chest wall thickness. Also described herein, with reference to FIGS. 3A to 3D, is a new method of effectively locating the pleural cavity of a patient. Conventional methods for locating the pleural cavity involve identifying the fifth intercostal space by locating proxy markers such as nipple. However inherent variability of the nipple's position on a chest wall renders this an unreliable marker. It is understood that correctly locating the appropriate intercostal space on a patient's torso can be a challenging task with 40% of medical practitioners unsuccessful in a stress-free environment. This failure rate is estimated to be even higher for combat medics working under pressure as they must also deal with obstructing articles such as body armour and clothing articles on the patient.

FIGS. 3A to 3D illustrate a new method, deemed as the mid-arm point method, of locating a safe zone for administrating pleural decompression of a pleural cavity between the fourth to sixth intercostal spaces. It has been found during a study that researchers using the method were able to locate the safe zone 100% of the time. The method involves the following steps. First, the patient is positioned supine with the elbow flexed 90 degrees and forearm mid prone. Second, locate the mid-arm point of an upper arm between the olecranon and the acromion. Third, project a line, perpendicular to the upper arm, from the mid-arm point towards the torso of the patient with a tape ruler. Finally, mark the area of contact between the projecting line and the torso as a safe zone for administering pleural decompression. This new method of locating the safe zone is not only suitable for administering pleural decompression according to embodiments of the present invention, it is equally suitable for use with conventional NT devices for performing pleural decompression.

Referring now to FIGS. 4A to 4E, preferred embodiments of a surgical pleural decompression system 1 includes a base 100 mountable external and adjacent or above an intercostal space of a patient, a valve assembly 200 attachable to the base 100, the base 100 and the valve assembly 200 defines a guided passage for receiving an obturator assembly 300 configured to reach a pleural cavity by cutting through the chest wall tissues of the patient, and a cannula 400 detachably coupled to the obturator assembly 300 which is deployed as the obturator assembly 300 cuts through to the pleural cavity and creates a path for fluid extraction between the pleural cavity and the valve assembly 200. Each of the components will now be described in detail and methods of using the system will also be provided.

Figure 5A:
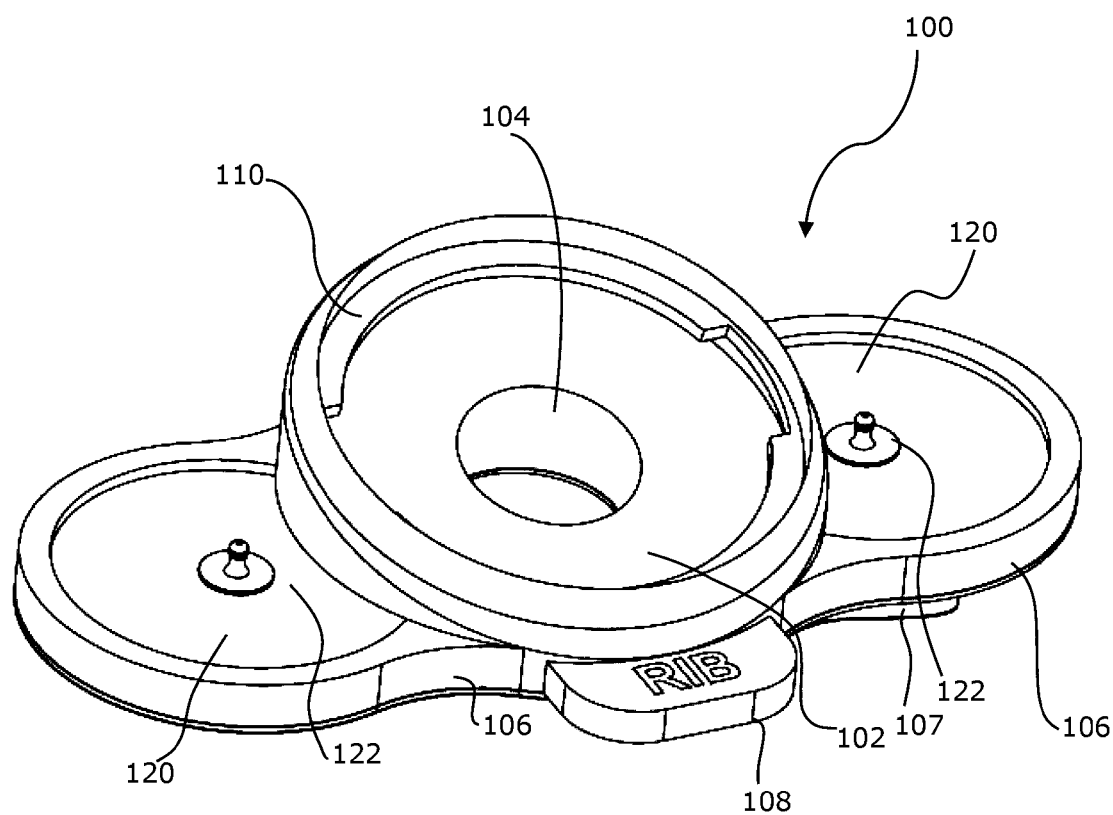
FIGS. 5A and 5B are rendered perspective views showing bases without sealed caps in accordance with embodiments of the invention.

FIGS. 5A to 7B show various embodiments and views of the base 100 for mounting above the intercostal space of the patient. The base 100 guides a user in locating the appropriate intercostal space with labelled indicators 108, and mounting the base 100 on the patient effectively marks the identified intercostal space. The base 100 also provides structural support for the pleural decompression assembly 1, and assists with guiding the insertion of the obturator assembly 300. With reference to FIGS. 5A, 6A and 7A, the base 100 comprises a plate 102 for mounting on the patient. In some configurations, the plate can be of a resilient material or a plastically deformable material to conform to the body contours of the patient. The plate 102 has an aperture 104 sized for receiving the obturator assembly 300 and the cannula 400. It is to be understood that the aperture 104 can also be sized for receiving conventional obturators, catheters and/or needles according to the NT method. An underside of the plate 102 is provided with adhesives 106, such as foamed adhesives, for securing the plate 102 to the patient after a protective layer 107 is removed prior to use. One would appreciate that any suitable adhesive for mounting the plate 102 to the patient can be used. The base 100 has one or more indicators in the form of rib alignment labels 108 to assist with positioning the aperture 104 of the base 100 for receiving the obturator assembly 300 between ribs of the patient. The rib alignment labels 108 can extend in opposite directions of the base 100 as shown in the Figures.

The base 100 is provided with a docking or coupling means 110 in the form of a threaded rim located about the aperture 104 for receiving the valve assembly 200. The rim is supported above a wall 111 of varying height such that a plane of the rim 110 is inclined relative to an axis perpendicular to the plane of the plate 102 as shown in the Figures. It is to be appreciated that while a thread rim is described for coupling with the valve assembly 200, any other suitable docking or coupling means 110 can be used, with non-limiting examples including interference fit coupling and interlocking clips for "push and click" coupling. In one configuration, the aperture 104 is also similarly angled so that obturator access occurs at an appropriate angle of entry between rib interspaces. The inclined angle of the rim 110 and/or the aperture 104 facilitates access of the pleural cavity while reducing the likelihood of damage to the intercostal neuromuscular bundle.

Side portions 120 may be provided extending in opposite directions from the plate 102 for stabilising the plate 102 from movement when applied to the torso of the patient. In one configuration, the side portions 120 and the plate 102 form a dumbbell shape for increased surface area of contact so as to prevent lateral displacement when the base 100 is mounted to the patient. The base 100 can also be provided with one or more electrodes 122 embedded in the plate 102 and/or the side portions 120 for outputting data such as information relating to cardiac spatial data to an external monitoring device (not shown). With reference to FIG. 5A, the electrodes 122 positioned as shown and mounted to the patient in accordance to the mid-arm point method for locating the intercostal space advantageously provides spatial cardiac monitoring in three orthogonal directions.

Figure 5B:
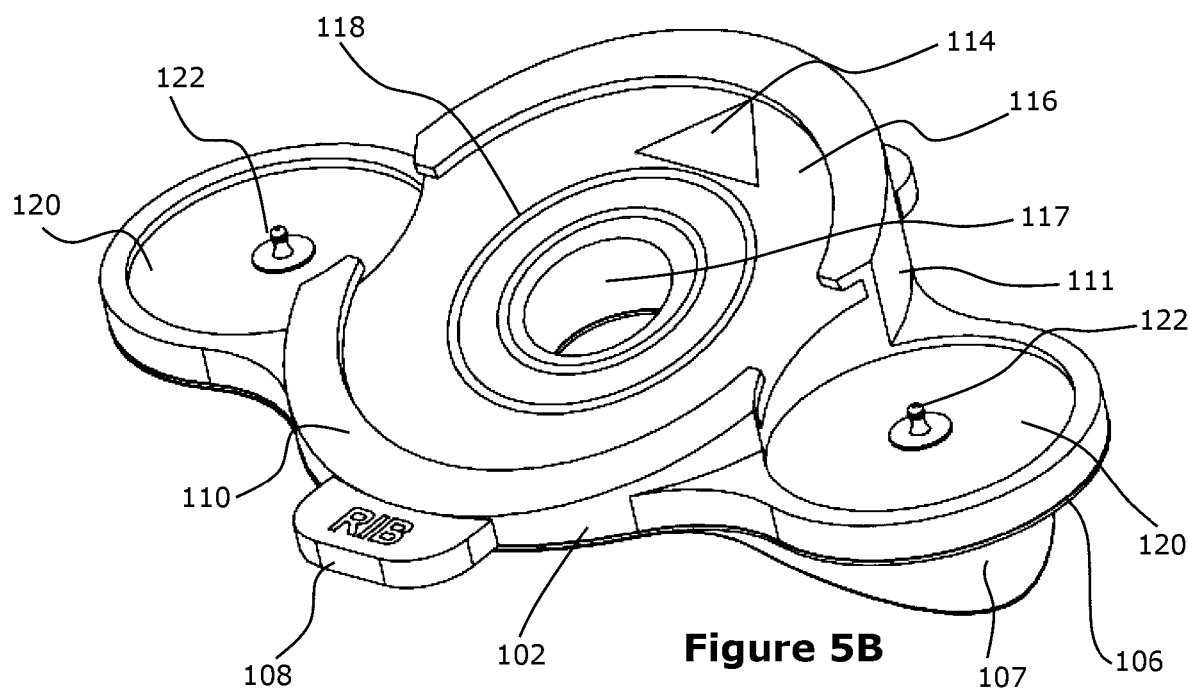
Figure 6A:
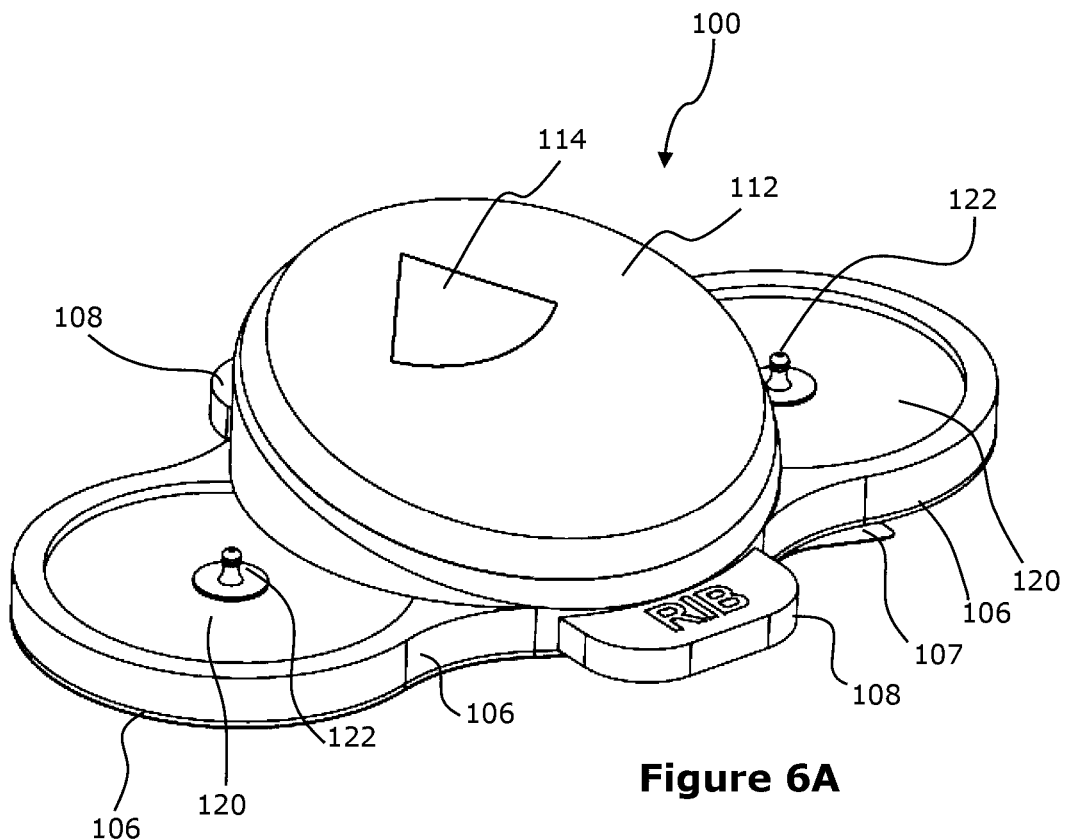
FIGS. 6A and 6B are rendered perspective views showing bases with sealed caps in accordance with embodiments of the invention.
Figure 6B:
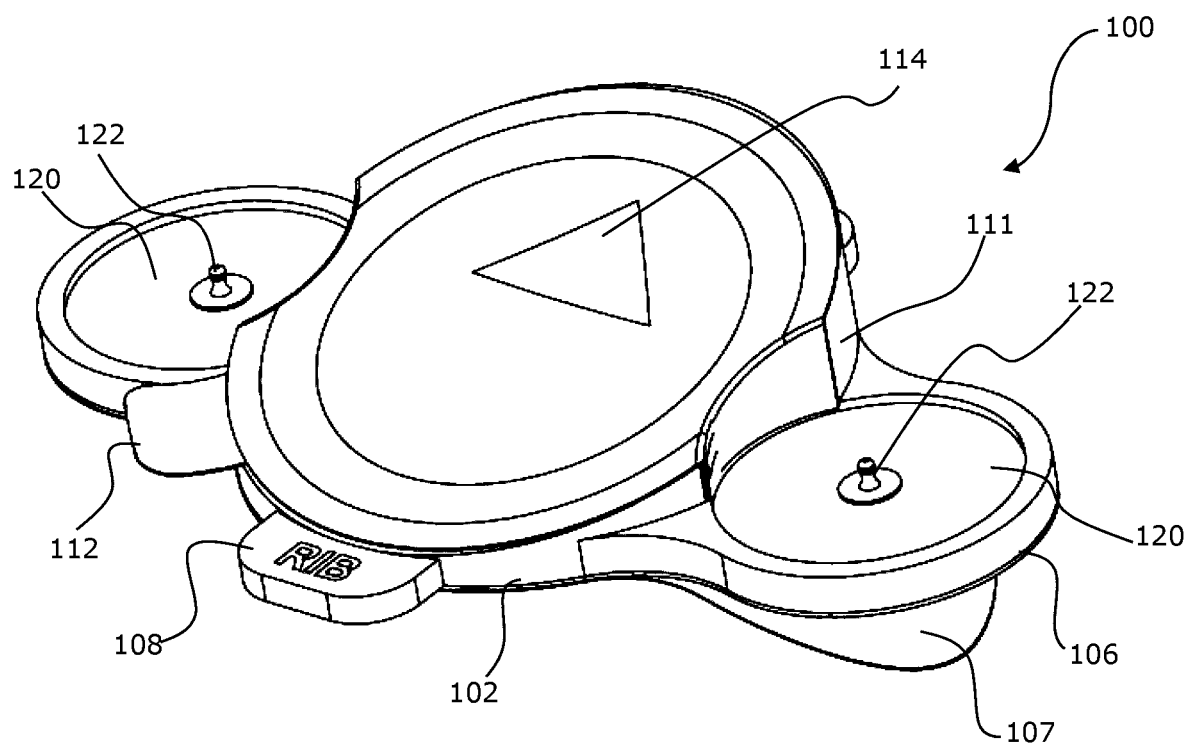
Figure 7A:
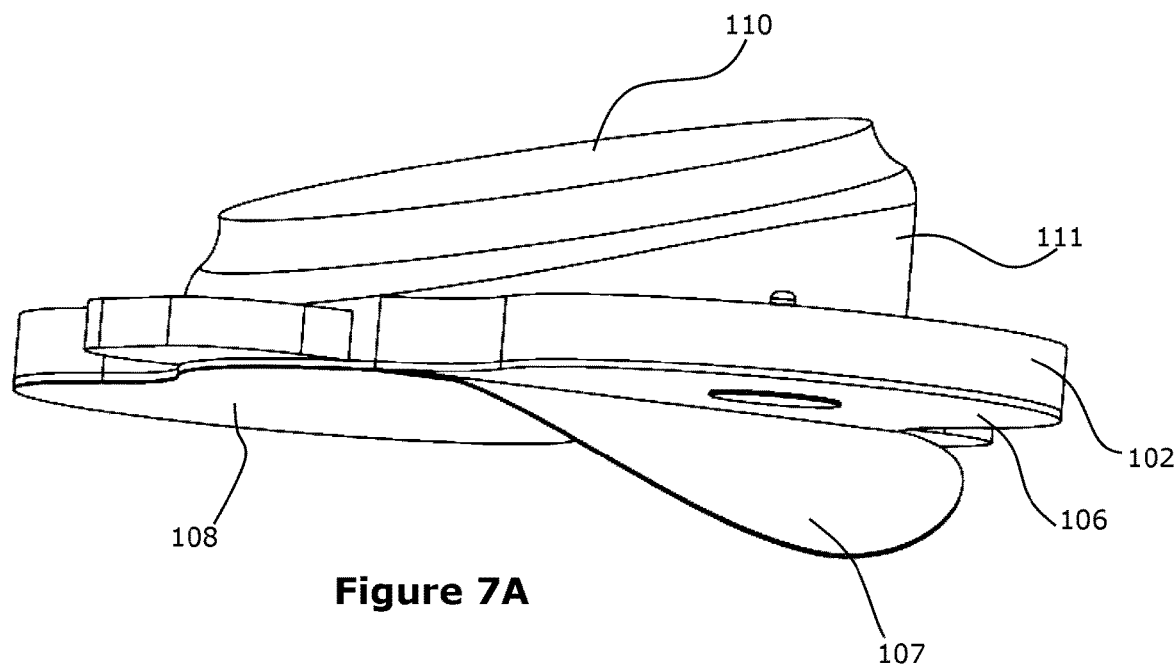
FIG. 7A is a rendered side view showing the base of FIG. 5A.
Figure 7B:
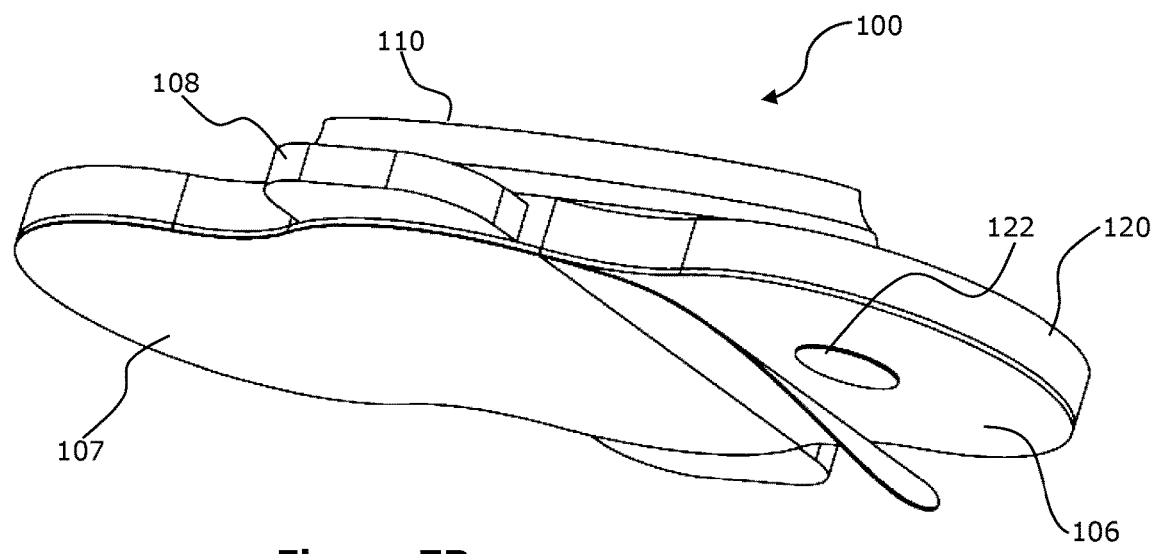
FIG. 7B is a rendered bottom perspective view showing the base of FIG. 5B.
Figure 8:
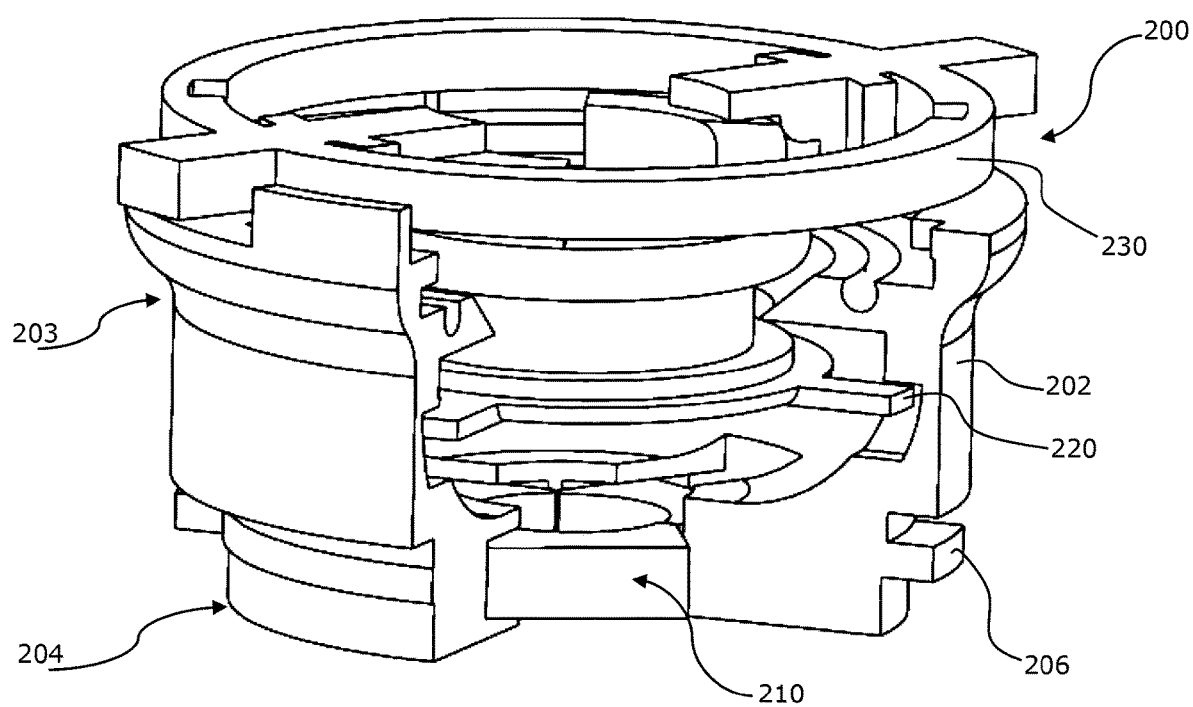
FIG. 8 is a rendered perspective view showing a valve assembly in accordance with an embodiment of the invention.
Figure 9A:
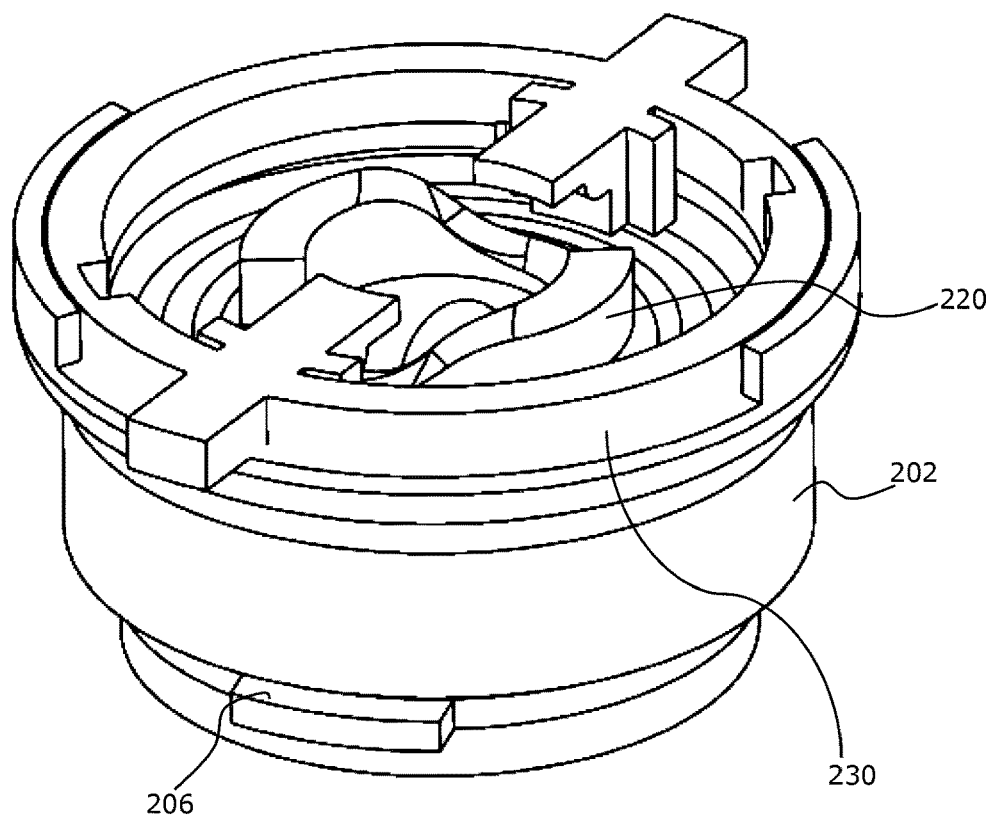
FIGS. 9A and 9B are rendered top perspective views showing different configurations of a valve locking tab in accordance with an embodiment of the invention.
Figure 9B:
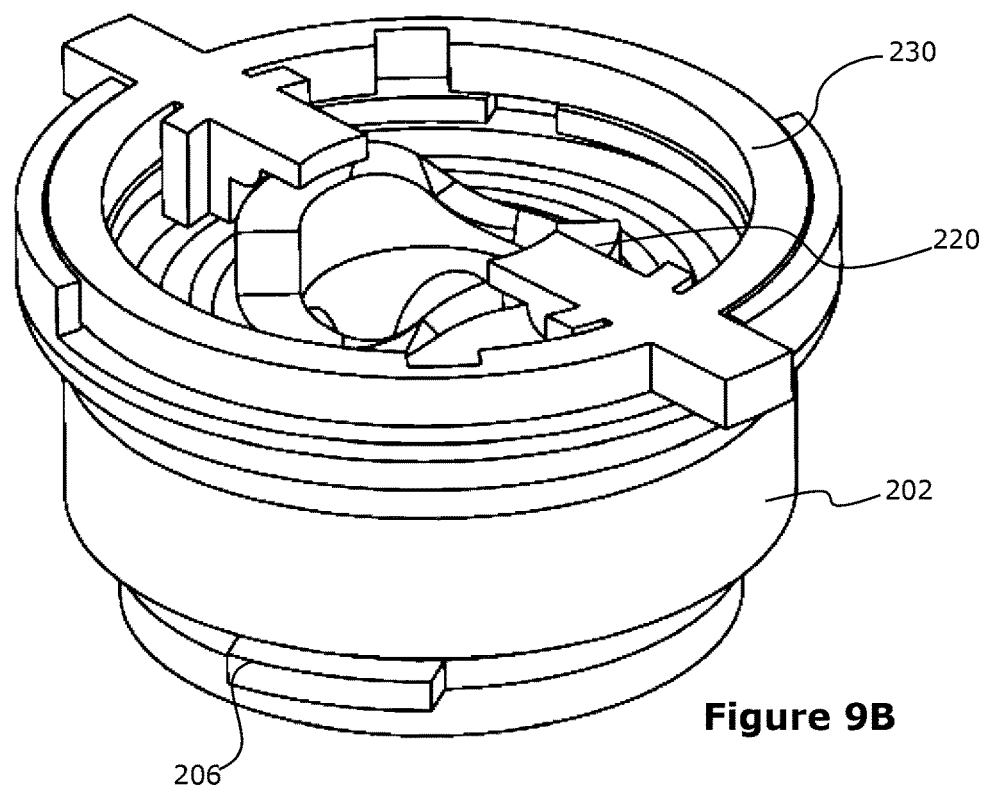

The base 100 can also be provided with an aperture cap 112 for sealing the space between the aperture 104, the wall 111 and the rim 110 as shown in FIG. 6A. The cap 112 can be vacuum fitted to create a sterile environment below the sealed space and to help ensure that asepsis is maintained after mounting the base 100 to the patient. In some embodiments, the cap is made from tin foil. The aperture cap 112 may also act as a cognitive aid to promote aseptic technique by an operator as the cap 112 will need to be removed or penetrated for access to the valve assembly 200 and the obturator assembly 300. FIGS. 5B, 6B and 7B show another embodiment the base 100. The aperture 104 can be further provided with a housing 116 enclosing the aperture 104 to define a passage 117 as shown in FIG. 5B for smooth obturator access and withdrawal. The housing 116 may also be provided with O-ring 118 for sealing with the valve assembly 200. The housing 116 also promotes asepsis by preventing environmental contamination to the space between the aperture 104, the wall 111 and the rim 110. Ventral arrow markers 114 can be provided on the aperture cap 112 and/or on the aperture valve 116 to indicate the correct orientation of the base 100 for mounting on the patient.

While the base 100 is described to be used with the pleural decompression system 1, it is to be understood that the base 100 is equally suitable for use as a standalone device for marking the intercostal position on the patient and providing stabilising structure suitable for use with conventional pleural decompression techniques as the aperture 104 can be configured and sized to receive conventional obturators, catheters, needles and NT tools.

FIGS. 8 to 17 show various embodiments and views of the valve assembly 200. The valve assembly 200 comprises a valve housing 202 having a first end 203 configured for use as an access port for receiving the obturator assembly 300 and for coupling to a fluid extraction device (not shown) once the cannula 400 has been deployed, a second end 204 configured for coupling to the base 100 and placement external and above or adjacent the intercostal space, and a passage through a valve 220 for receiving the obturator assembly 300 and the cannula 400. In one configuration the housing 202 made from a transparent material so that the contents of the valve assembly 200 and any fluid extracted from the pleural cavity into the valve assembly 200 can be easily inspected by a user. The second end 204 of the valve assembly 300 is provided with one or more docking tabs 206 for coupling to the docking rim 110 of the base 100. In one configuration, docking the valve assembly 200 is performed by pushing and clicking the docking tabs 206 within complementary recesses of the docking rim 110. The valve assembly 200 can be subsequently removed from the base 100 by rotating the valve assembly 200 with respect to the base 100 so that the docking tabs 206 moves through the threaded rim 110 and becomes uncoupled.

Figure 10A:
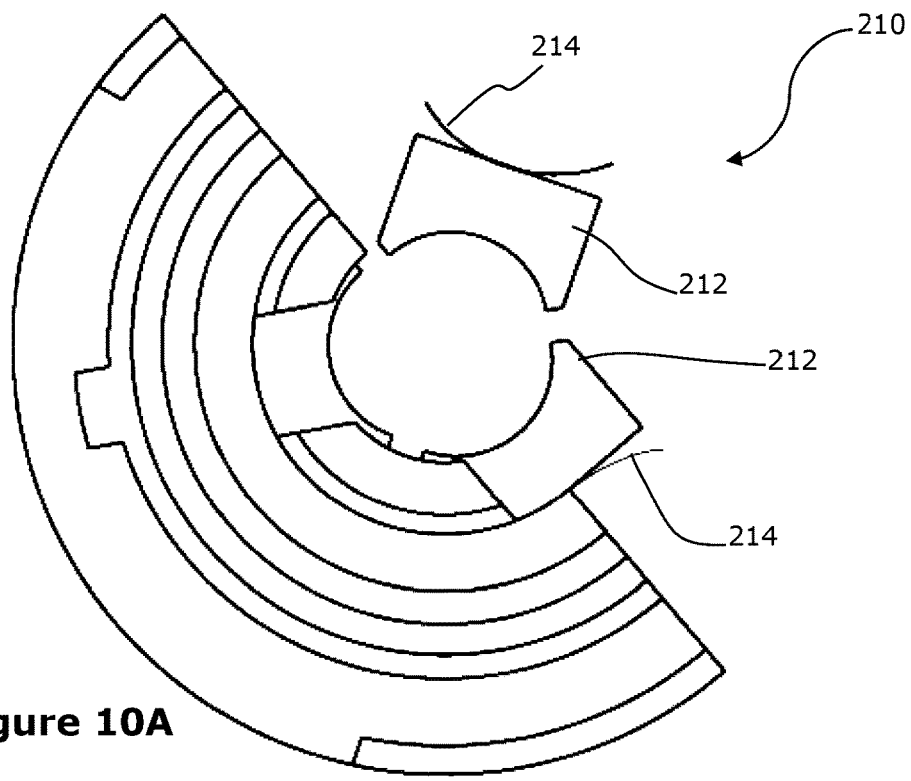
FIGS. 10A and 10B are rendered partial sectional plan views showing the valve assembly with docking locks in accordance with an embodiment of the invention.
Figure 10B:
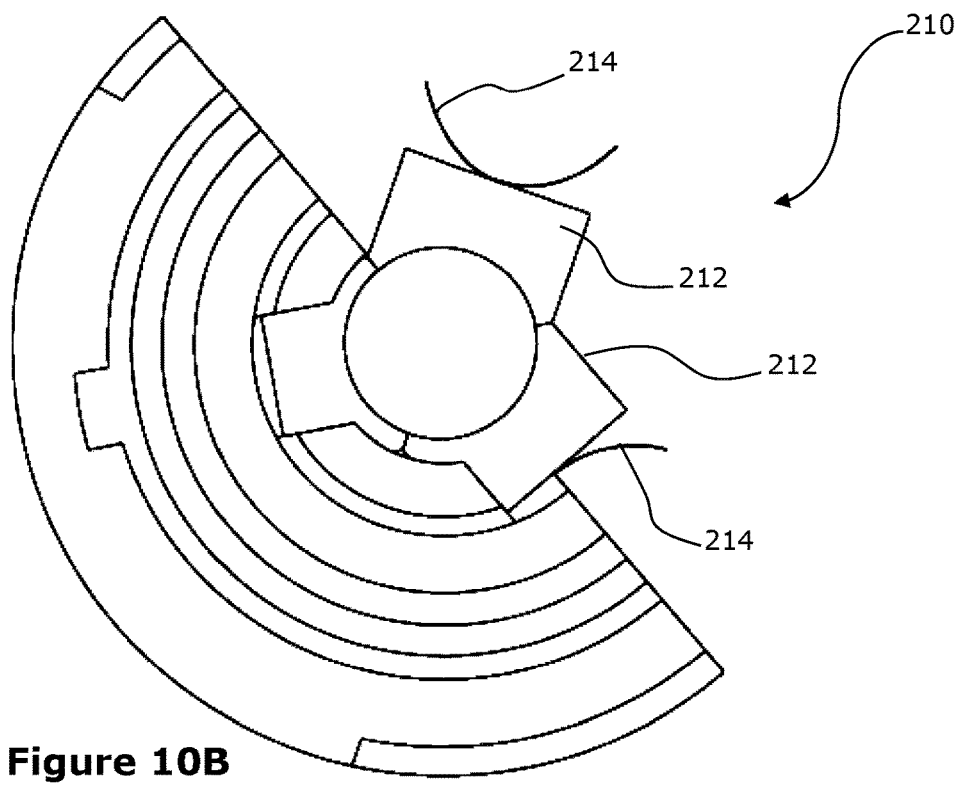
Figure 11:
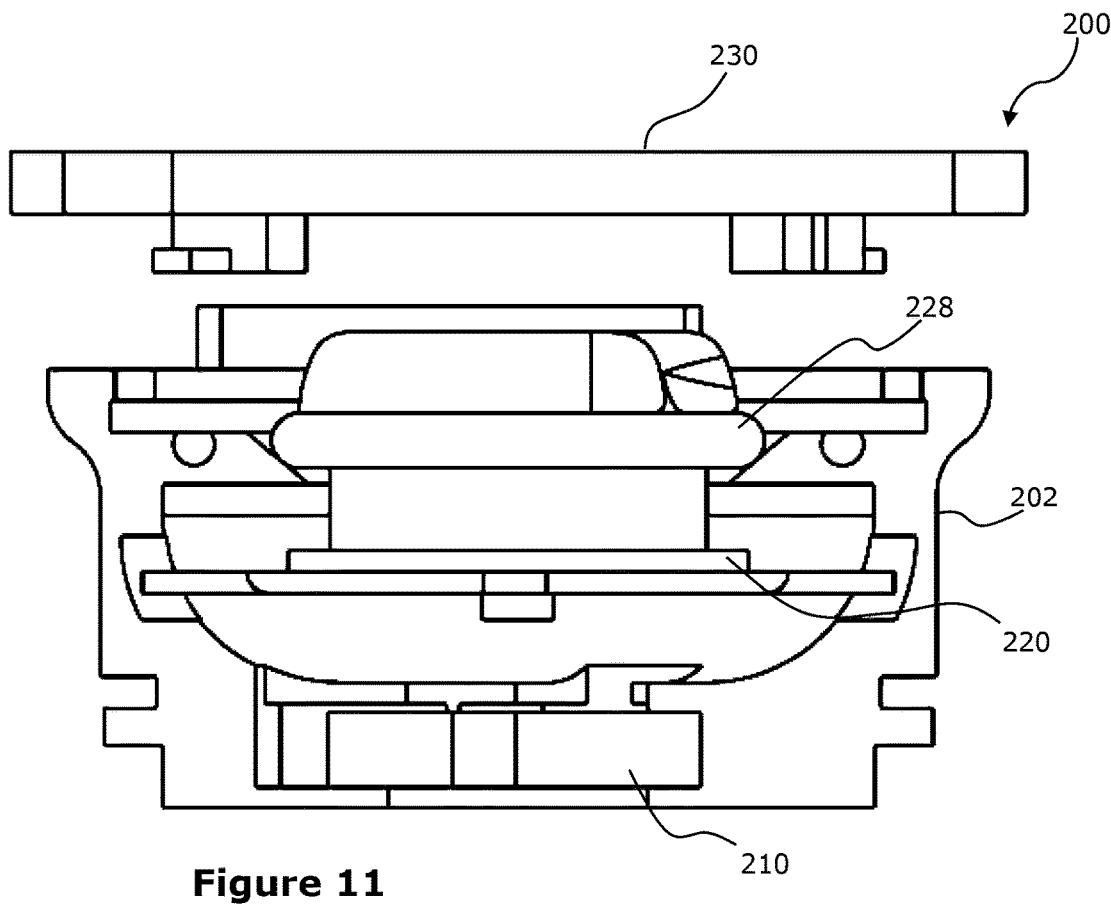
FIG. 11 is a rendered partial sectional side view showing the valve assembly of FIG. 8.
Figure 12:
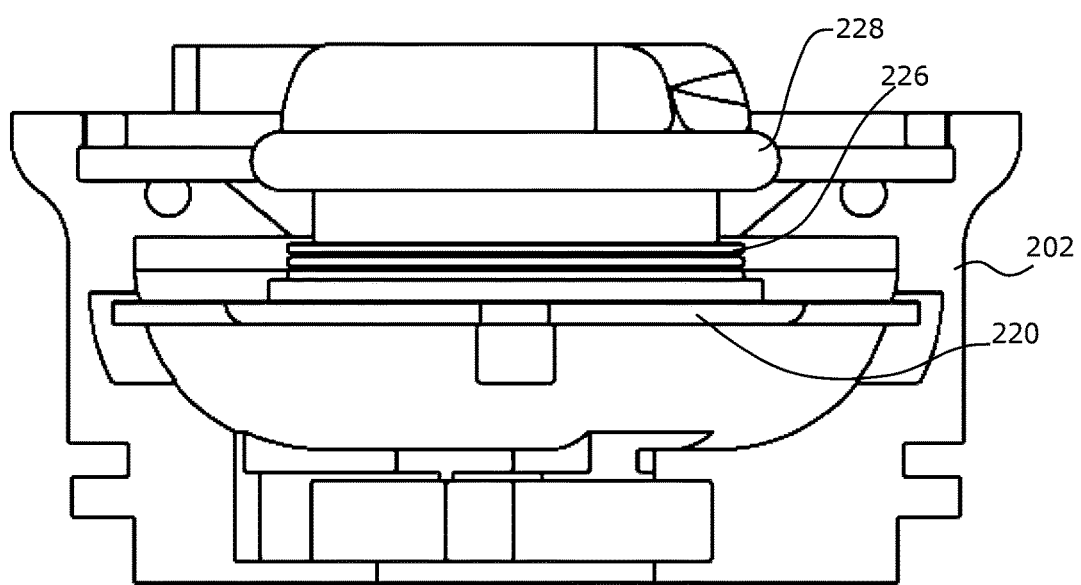
FIG. 12 is a rendered partial sectional side view showing the efflux valve of the valve assembly of FIG. 8.
Figure 15:
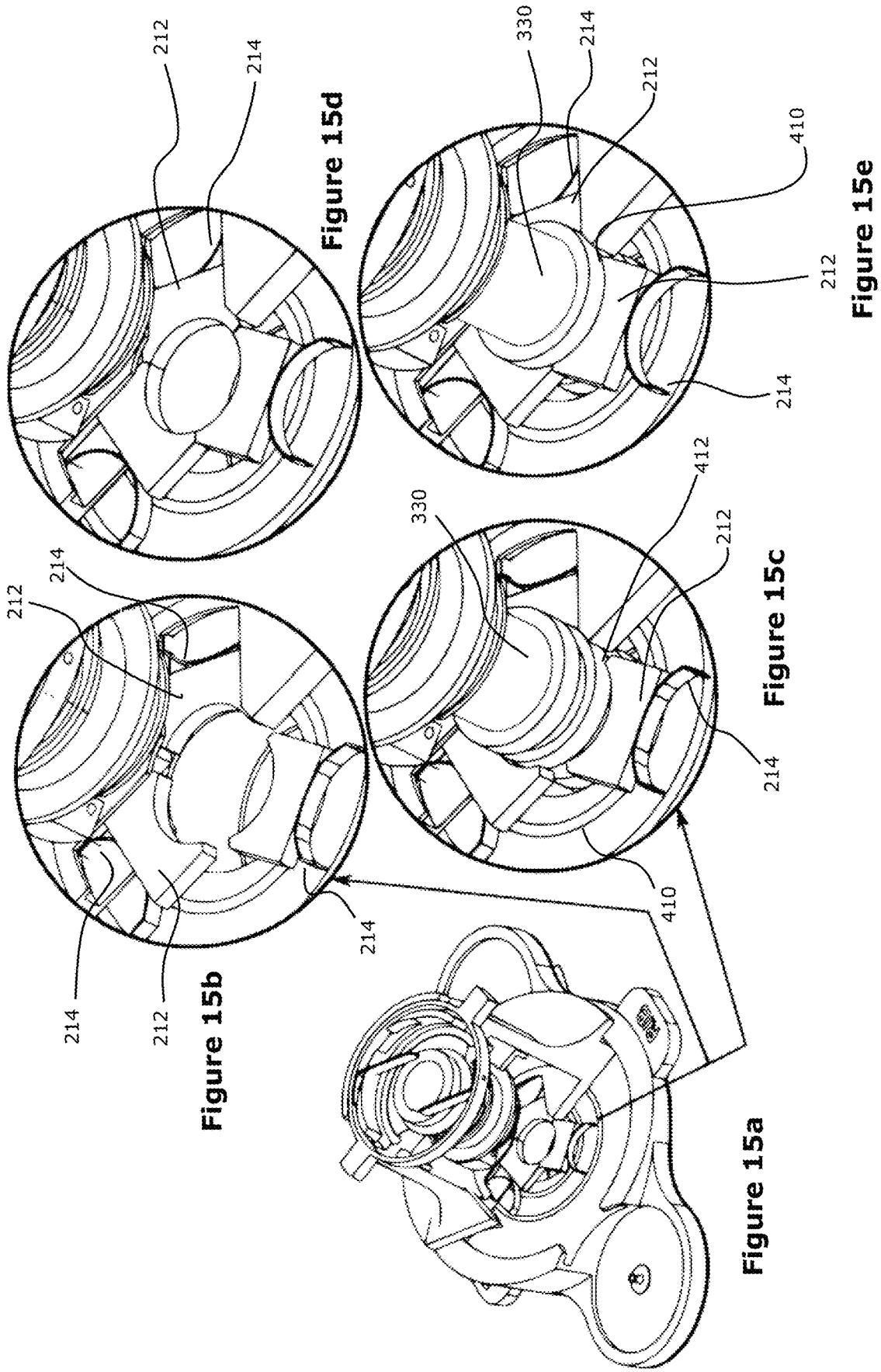
FIG. 15 is a rendered perspective sectional view showing an assembled valve assembly coupled to a base in accordance with another embodiment of the invention.

At or about the second end 204 of the valve assembly 200, there is provided inside the housing 202 a spring-loaded locking mechanism 210 for locking a corresponding locking portion 412, or a groove, of the cannula 400 by way of a 'push and click' action. The locking mechanism 210 comprises three centrally directed concave shaped locking members which forms an aperture corresponding to the shape of and dimension of the locking portion 412 of the cannula 400. Each of the locking members 212 are biased at one end with a leaf spring 214 to coerce the locking members 212 towards the middle to form the locking aperture as shown in FIGS. 10B and 15. The locking members 212 can be pushed apart with force against the left springs 214, for example during the insertion of the obturator assembly 300, to temporarily allow passage of the cannula body 420 with larger diameters as shown in FIGS. 10A and 15.

Figure 13A:
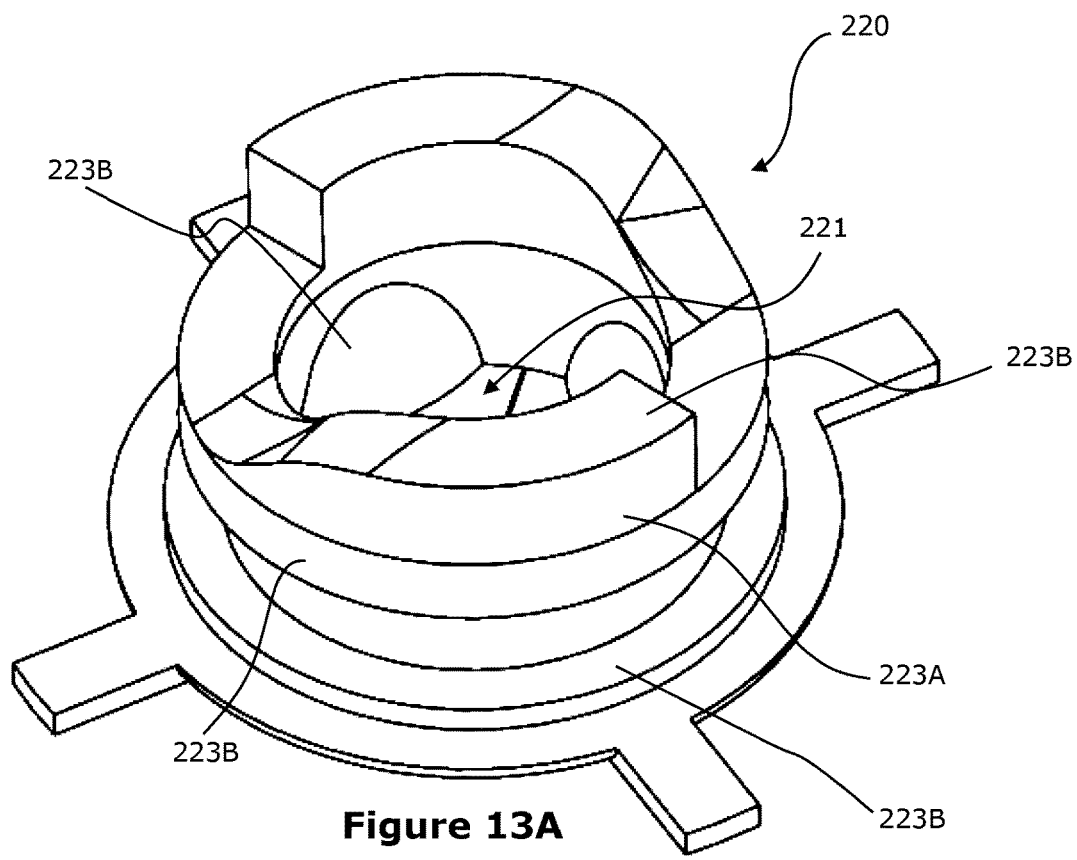
FIGS. 13A and 13B are rendered perspective sectional views showing the efflux valve of the valve assembly of FIG. 8.
Figure 13B:
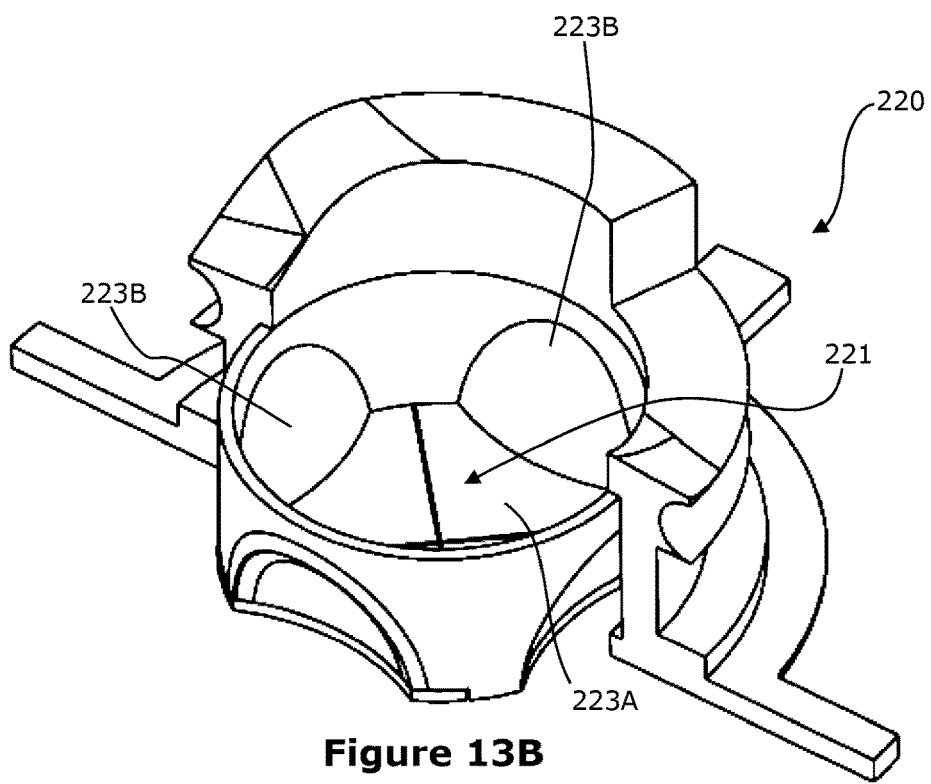

The valve housing 202 is provided with the valve 220 having a central passage 221 to control fluid flow from the pleural cavity of the patient. The valve 220 has a port door 222 for sealing an opening of the passage at a distal end of the valve 220; a flow indicator 224 in the form of a ring surrounding the valve 220 to indicate the presence of any fluid, such as gas or pleural fluids, extracted from the pleural cavity into the valve 220; a valve spring 226 to bias the flow indicator 224 in a direction towards the distal end of the valve 220; a O-ring 228 for sealing the connection between the valve 220 and the valve housing 202. In some embodiments, the port door 222 is in the form of a cork held by way of a hinge a shown in FIG. 14, and can be opened by way of inserting the obturator assembly 300 and the cannula 400 as shown in FIG. 15. In another embodiment, as seen in FIGS. 13A and 13B, the valve 220 is provided with a flex valve 223A at the bottom of the valve 220 and valve flaps 223B around the perimeter of the valve 220 configured to allow one-way movement of fluids from the patient's body to the valve housing 202 in use. In one configuration, the valve 220 is a one-way efflux valve. For efflux valve configurations, the valve can be configured with an operator adjustable valve lock to prevent efflux if required.

Figure 4A:
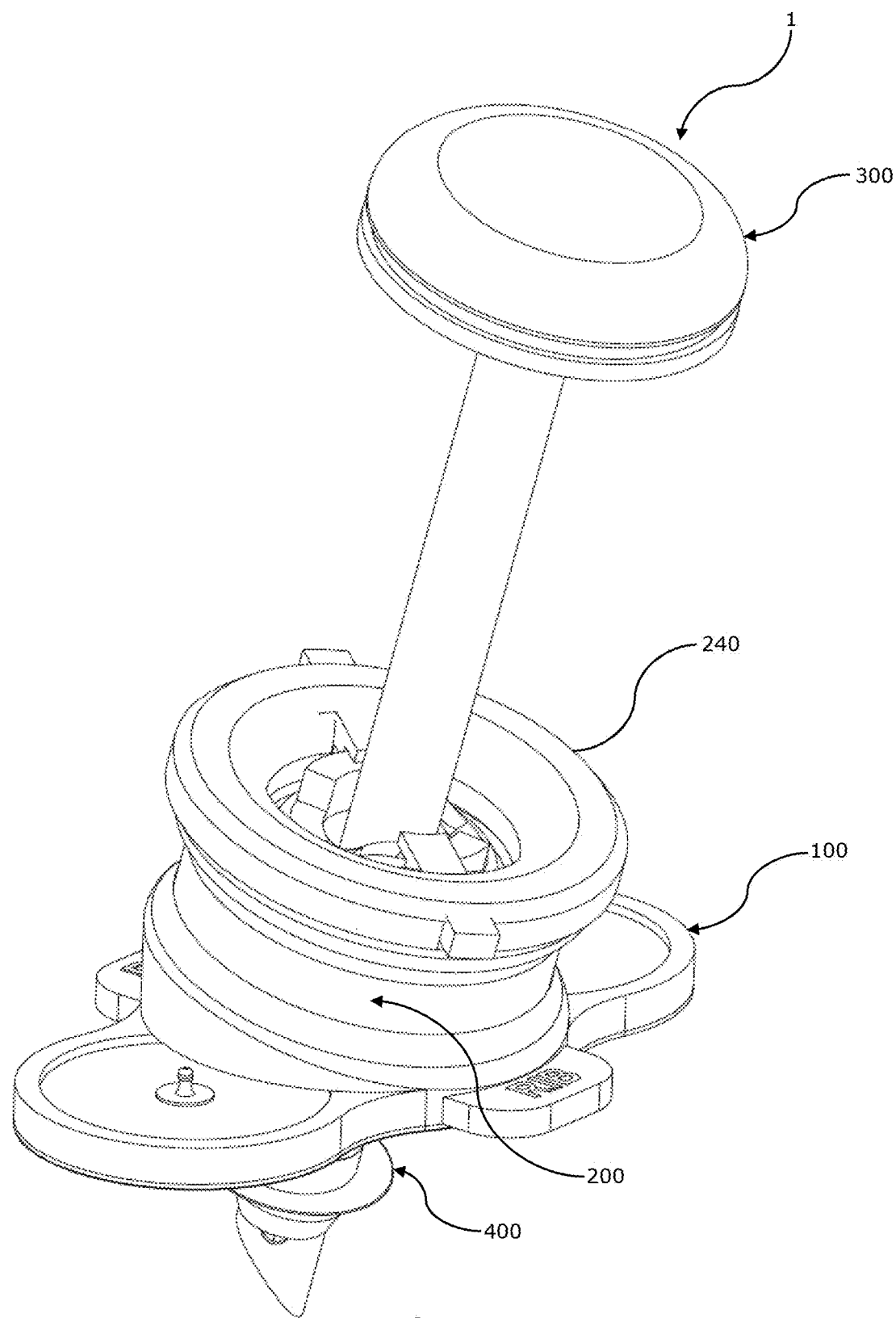
FIG. 4A is a rendered view showing an assembled surgical pleural decompression system in accordance with an embodiment of the invention.
Figure 4B:
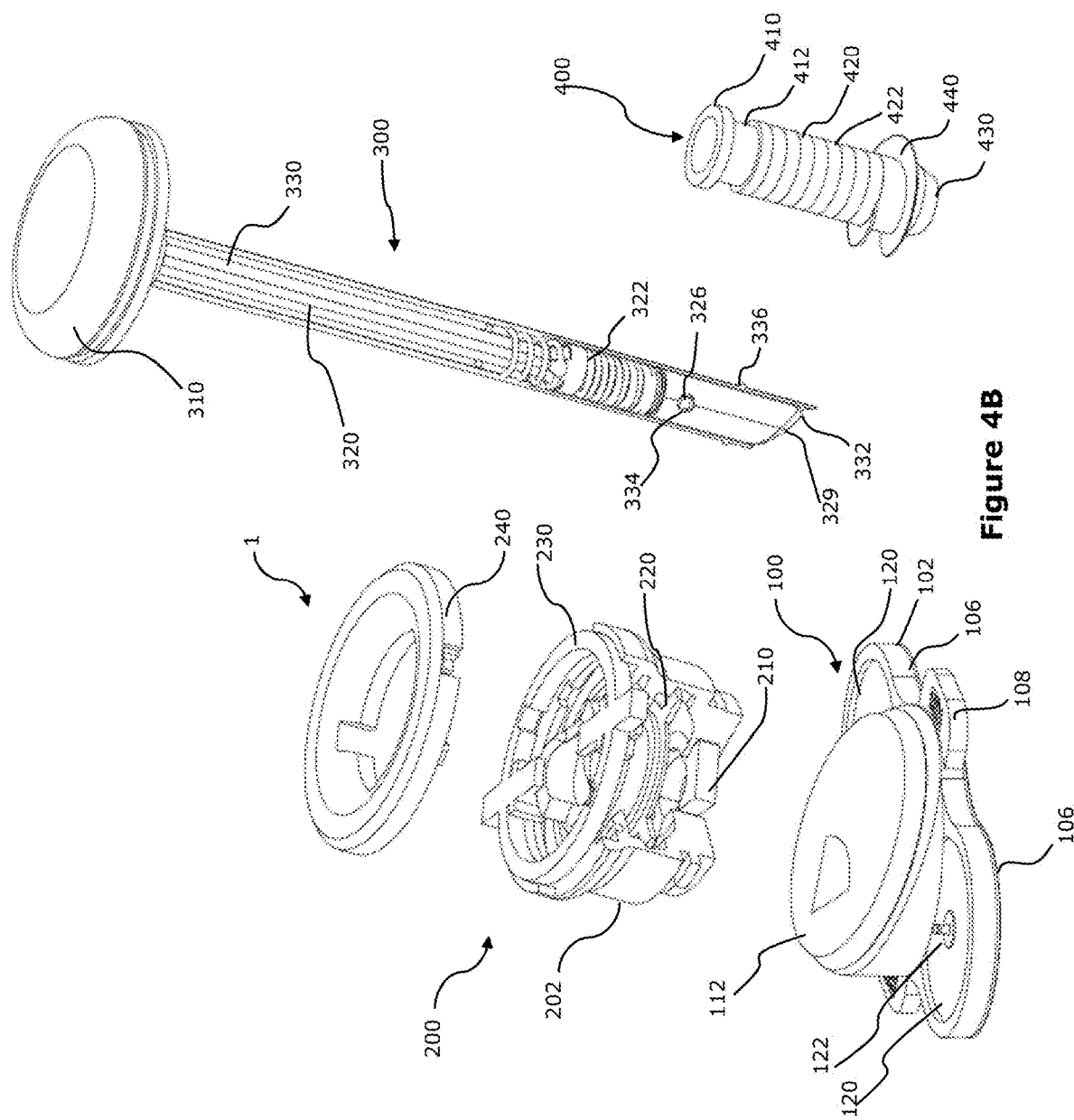
FIG. 4B is a rendered partial exploded view showing the system of FIG. 4A.
Figure 4C:
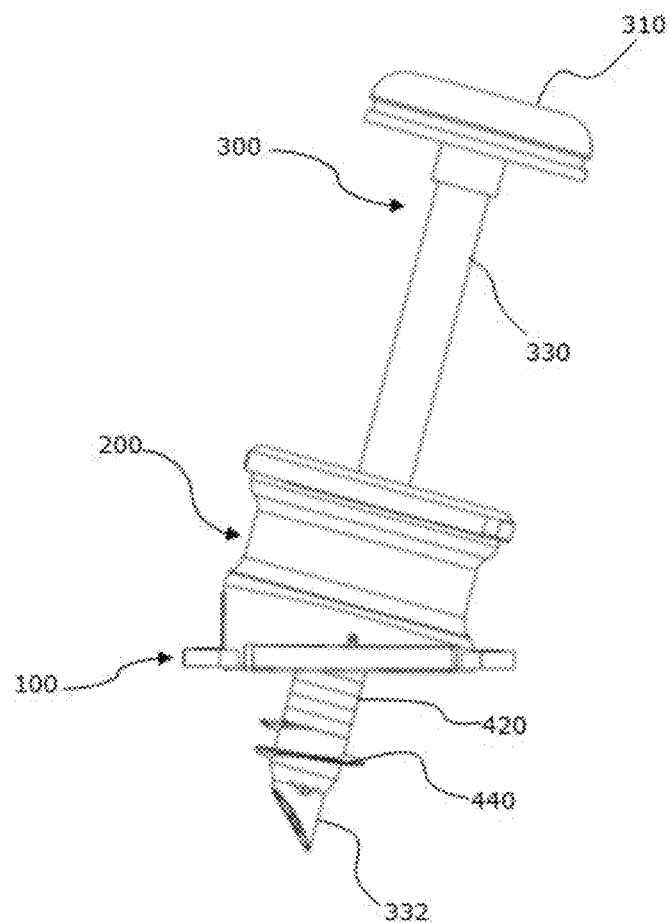
FIG. 4C is a rendered side view showing the system of FIG. 4A.
Figure 4D:
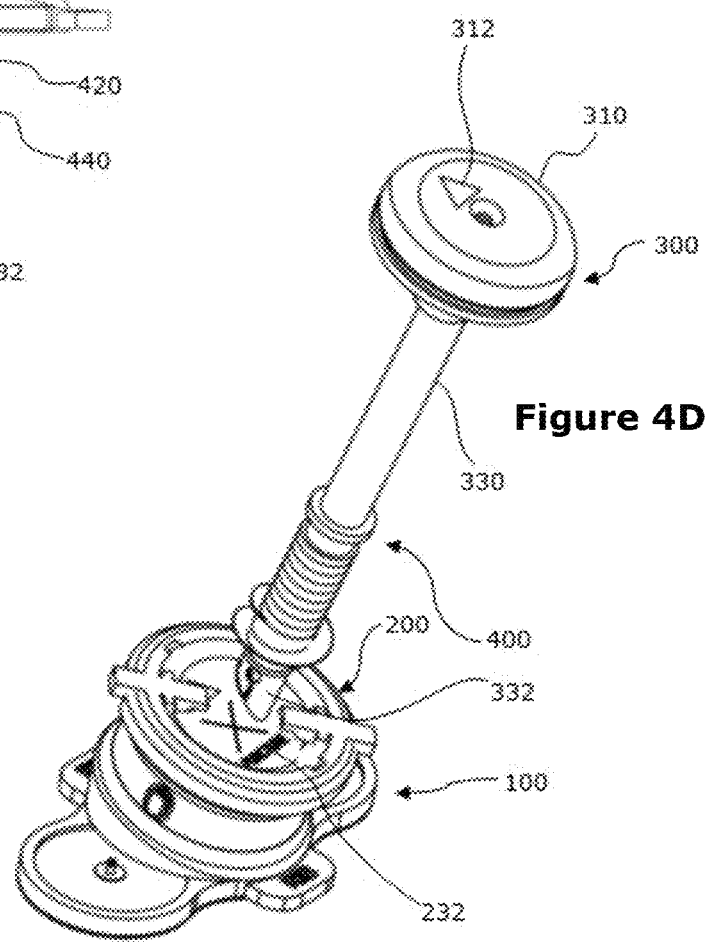
FIG. 4D is a rendered perspective view showing another assembled surgical pleural decompression system in accordance with an embodiment of the invention.
Figure 4E:
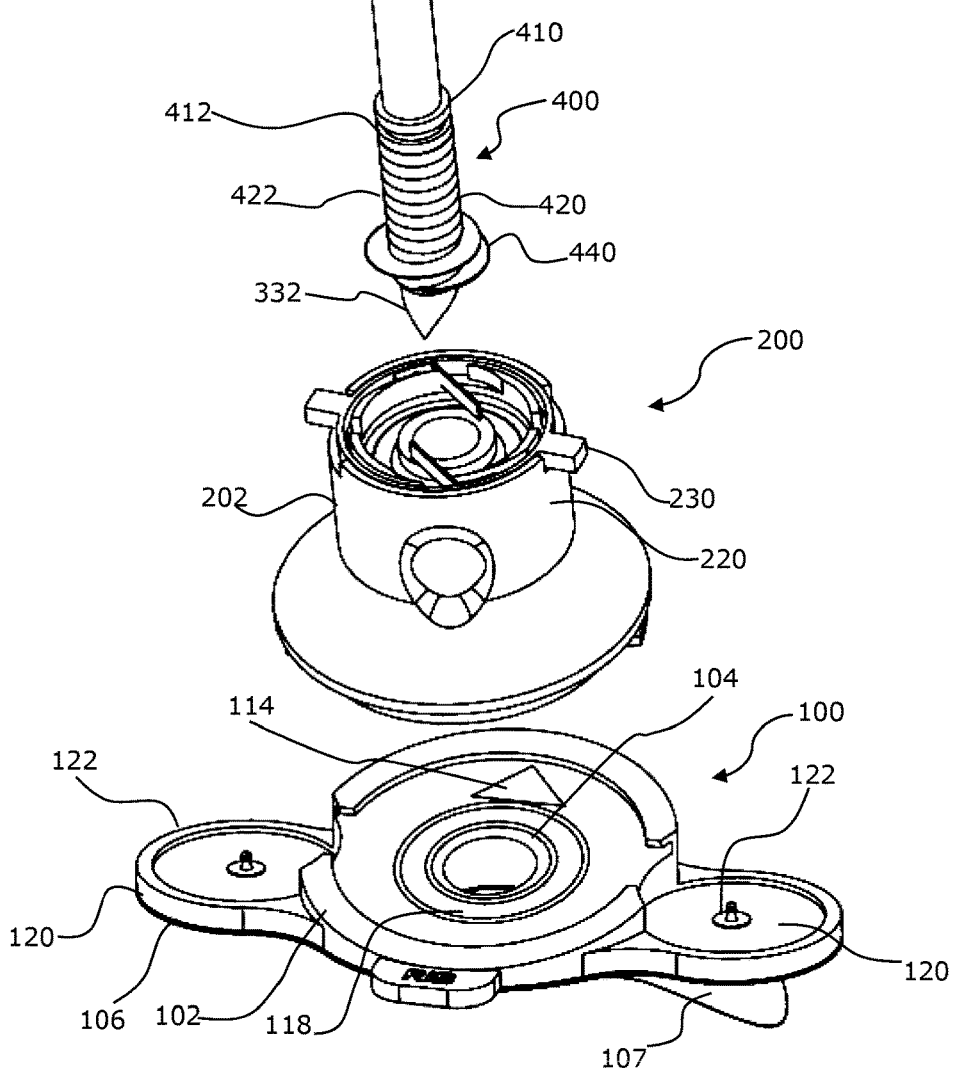
FIG. 4E is a rendered perspective view showing another assembled surgical pleural decompression system in accordance with an embodiment of the invention.
Figure 14:
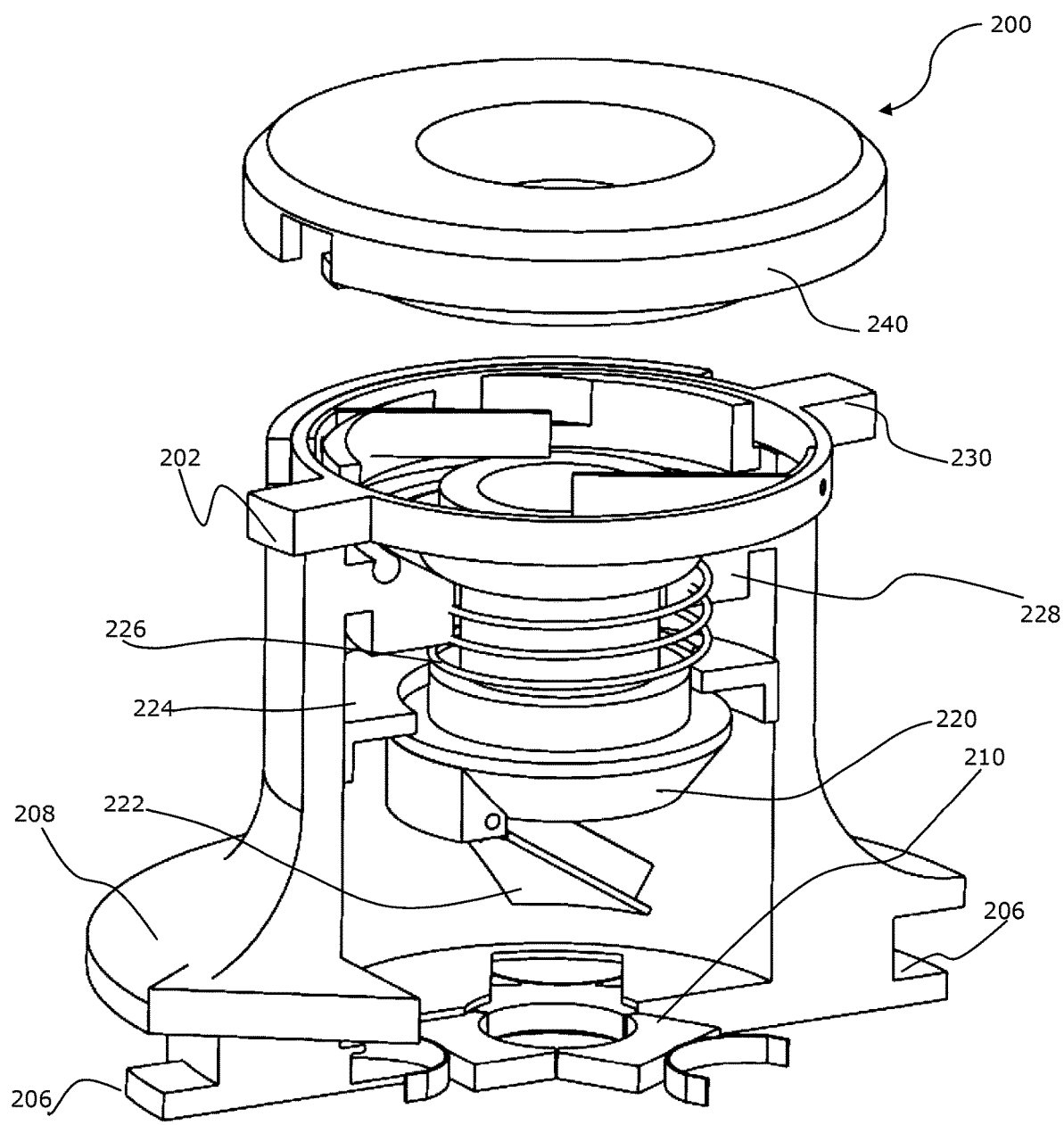
FIG. 14 is a rendered perspective sectional view showing a valve assembly in accordance with another embodiment of the invention.

The first end of the valve 203 is provided with a coupler 230 in the form of a locking ring for coupling with a sealing cap 240 which can be connected to external fluid extraction devices (not shown) such as a fluid collection bag. In the configuration as shown in FIG. 4B, the cap 240 is coupled to the valve assembly 200 by way of pushing and clicking the cap 240 on to the locking ring coupler 230. FIG. 14 shows another embodiment of the sealing cap 240 which greater surface area of the valve assembly 200 is covered by the sealing cap 240.

Figure 16:
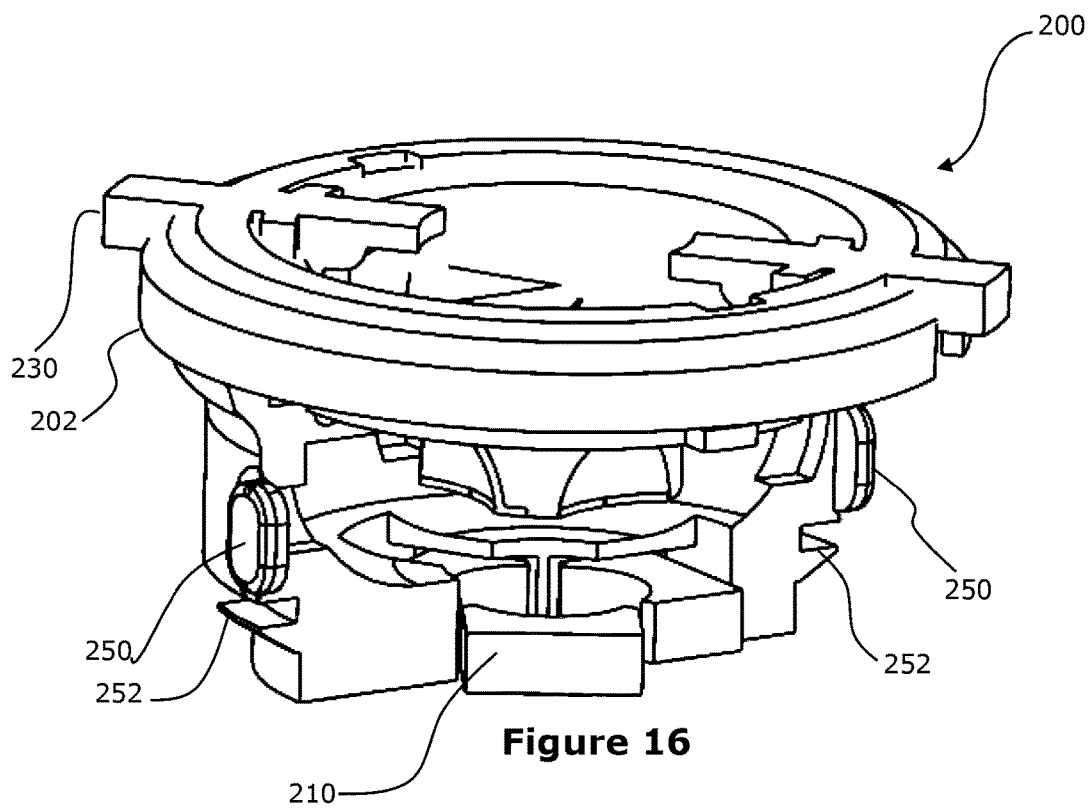
FIG. 16 is a rendered perspective sectional view showing a valve assembly having a valve seal in accordance with another embodiment of the invention.
Figure 17:
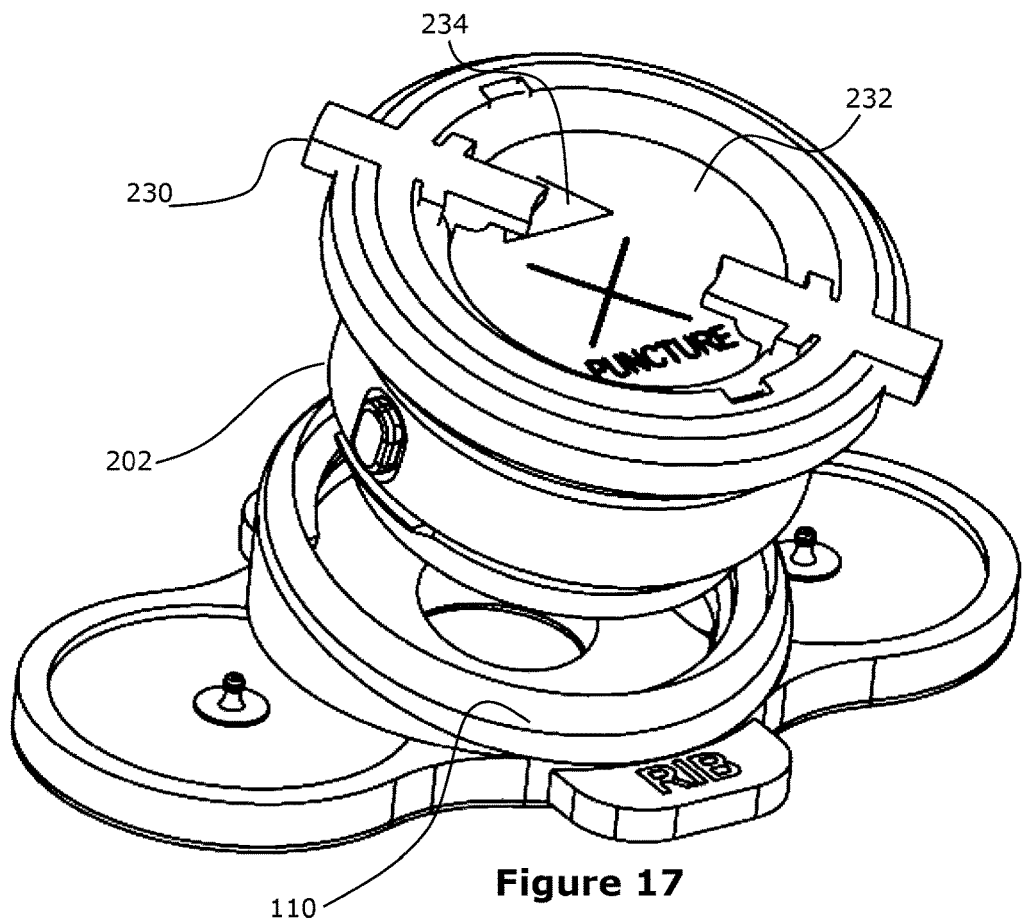
FIG. 17 is a rendered perspective sectional view showing an assembled valve assembly having a valve seal coupled to a base in accordance with another embodiment of the invention.
Figure 18:
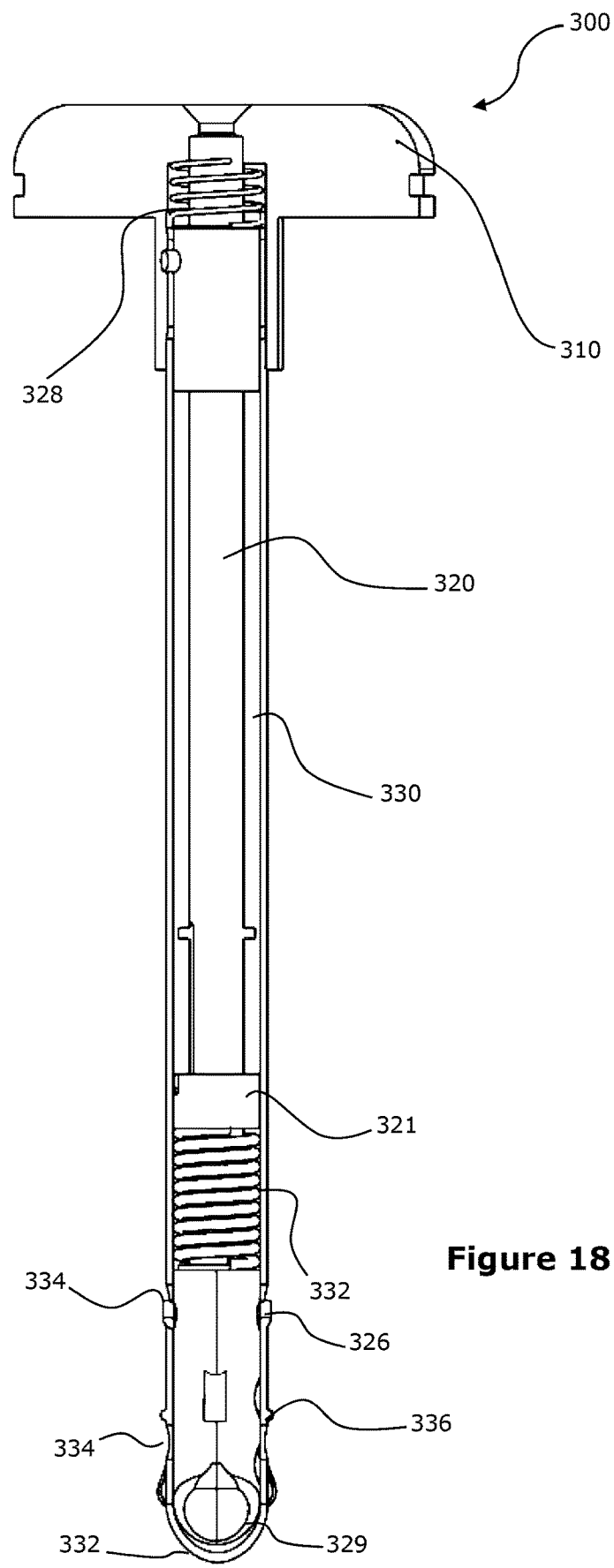
FIG. 18 is a rendered perspective view showing an obturator assembly in accordance with an embodiment of the invention.
Figure 19:
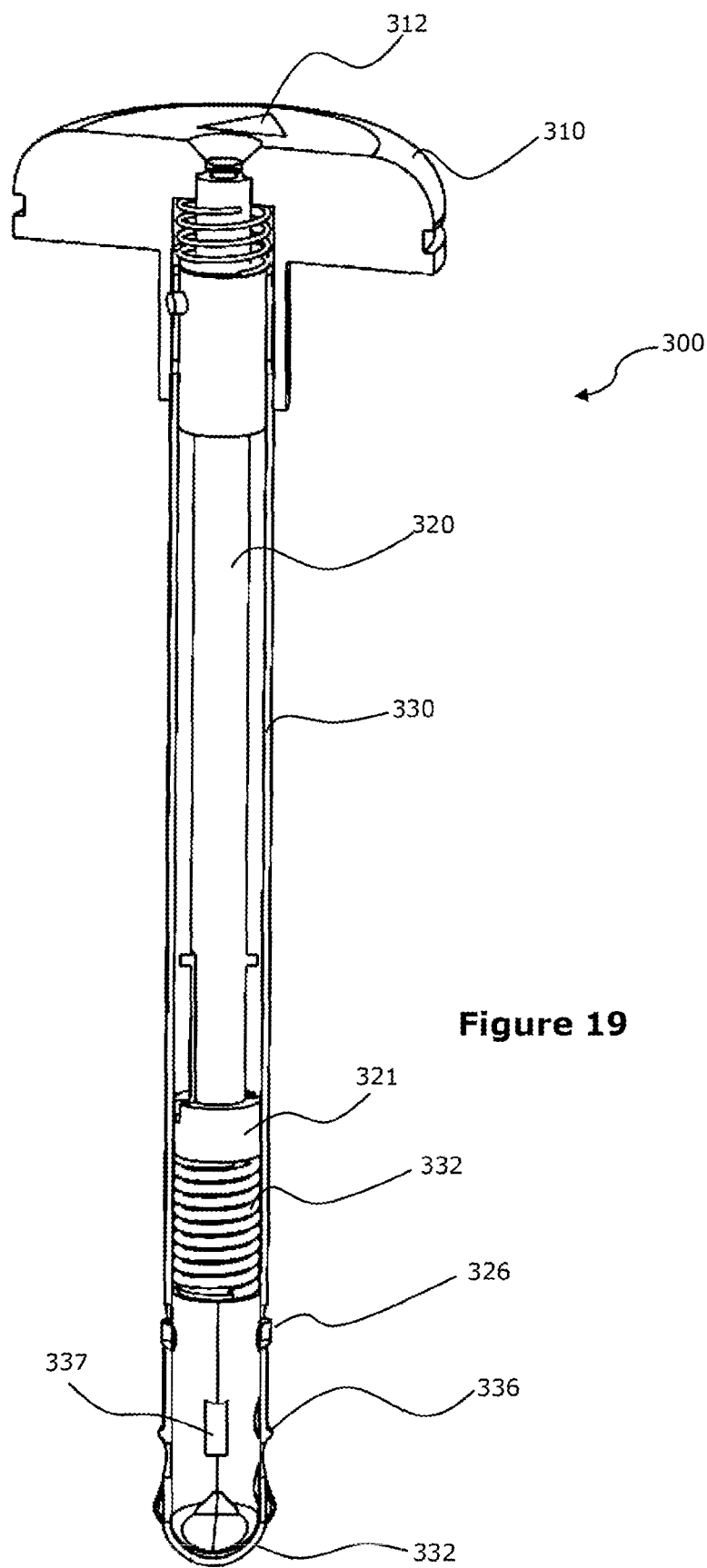
FIG. 19 is a rendered perspective view showing an obturator assembly in accordance with another embodiment of the invention.

FIGS. 16 and 17 show an alternative embodiment of the valve assembly 200. The valve assembly 200 can be provided with a removable or penetrable sealing cap 232 which can be pierced by the obturator assembly 300. The sealing cap 232 keeps the valve assembly 200 sterile prior to use. The sealing cap 232 can further be provided with alignment indicator 234 to indicate the directional orientation of the valve assembly 200 for use with respect to the base 100 and the patient. In some configurations, the valve housing 202 is provided with one or more couplers 250, 252 for coupling with the docking or coupling mechanism 110 of the base 100 as shown in FIGS. 16 and 17.

Figure 44:
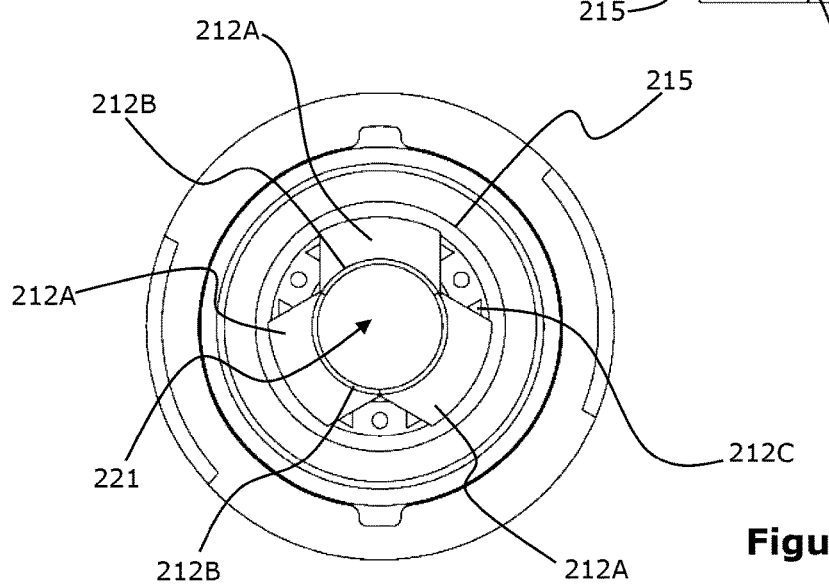
FIG. 44 is a rendered sectional top view of the valve assembly of FIG. 42 showing locking members in a closed state.
Figure 45:
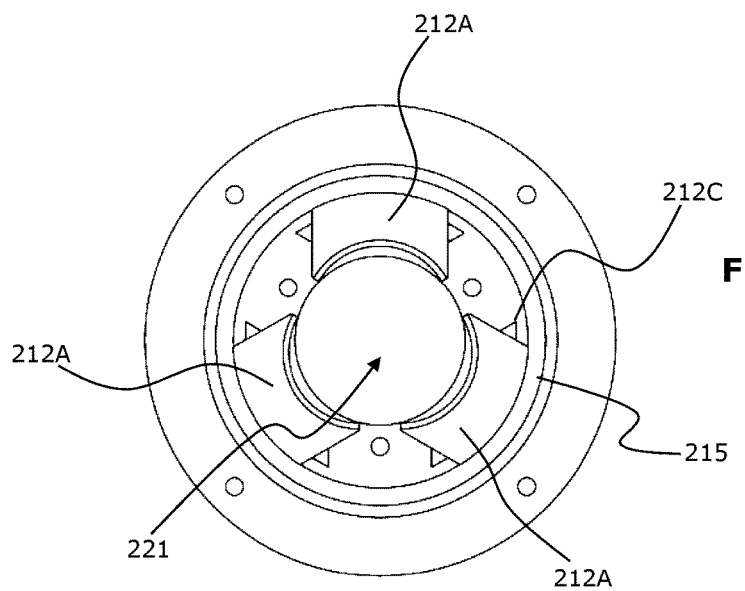
FIG. 45 is a rendered sectional top view of the valve assembly of FIG. 42 showing locking members in an opened state.
Figure 46:
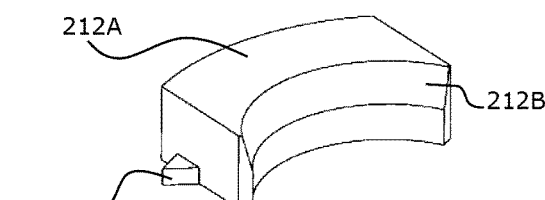
FIG. 46 is a rendered perspective view of a locking member of FIG. 42.

FIGS. 42 to 46 show another embodiment of the valve assembly 200. The valve assembly 200 may also be provided with an elastic member 215 in the form of an O-ring or expandable/collapsible band, which is configured to surround and apply a spring bias against the locking members 212A, urging the members 212A together in a closed state, as shown in FIG. 44. This provides the effect of allowing multiple locking members 212A to move between the closed state in which the locking members 212A substantially extend toward one another and an open state in which the locking members 212A are pushed back against the elastic member 215. The elastic member 215 advantageously exerts substantially an evenly spread amount of force on each of the locking members 212A, which allows a smoother passage of a cannula 400 through the valve assembly 200. Additionally, the lock members 212A may be configured with a chamfer 212B or a tapered portion as shown in FIG. 46 which interfaces with a cannula 400 to help push the locking members 212A apart as the cannula 400 slides through the opening or valve passage 221 of the valve assembly 200 between the locking members 212A. The lock members 212A may also be configured with side protrusions 212C in the form of tabs which are configured to be received within a corresponding slot or channel of the valve assembly 200 to restrict movement of the locking members 212A on a single plane (i.e. to prevent up/down movement of the locking members 212A). As described previously, the locking members 212A are configured to be moveable between an open state in which the locking members 212A are forced away from each other to allow the body of a cannula 400 to pass through, and a biased close state in which the locking members 212A are urged toward each other and form secures against a corresponding groove portion 412 of a cannula to lock the cannula in place; preventing it from being removed independently to the valve assembly 200.

Figure 20:
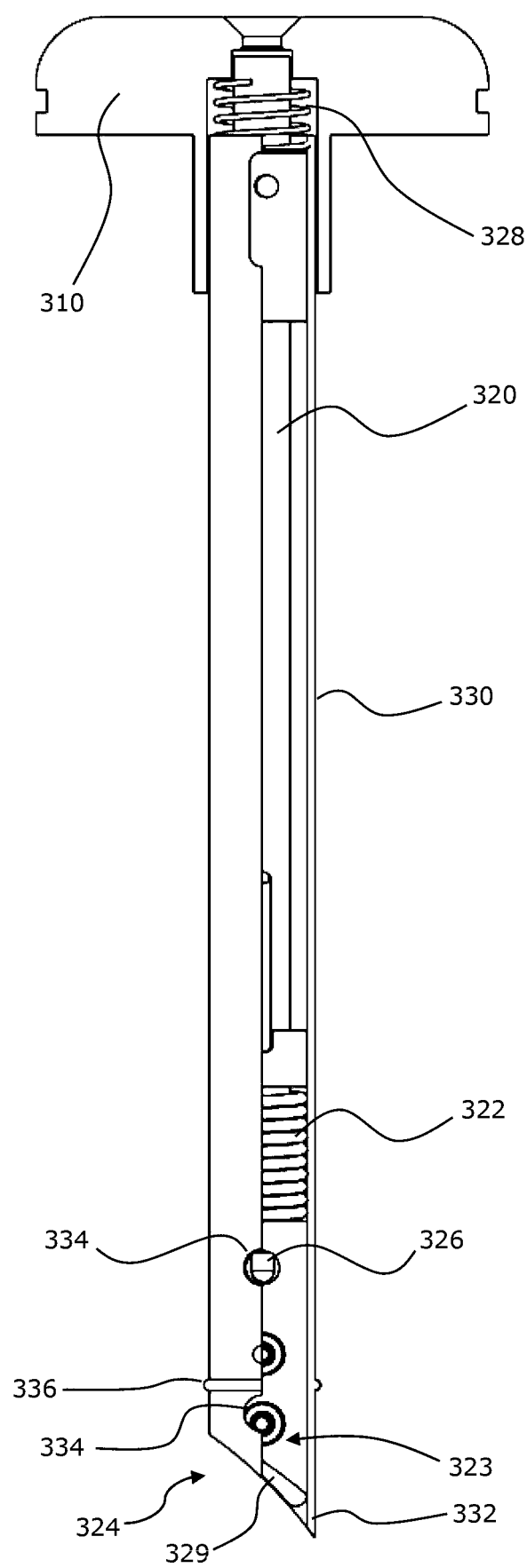
FIG. 20 is a rendered side view of the obturator assembly of FIG. 18 showing an inner stylet in a retracted configuration in accordance with an embodiment of the invention.
Figure 21:
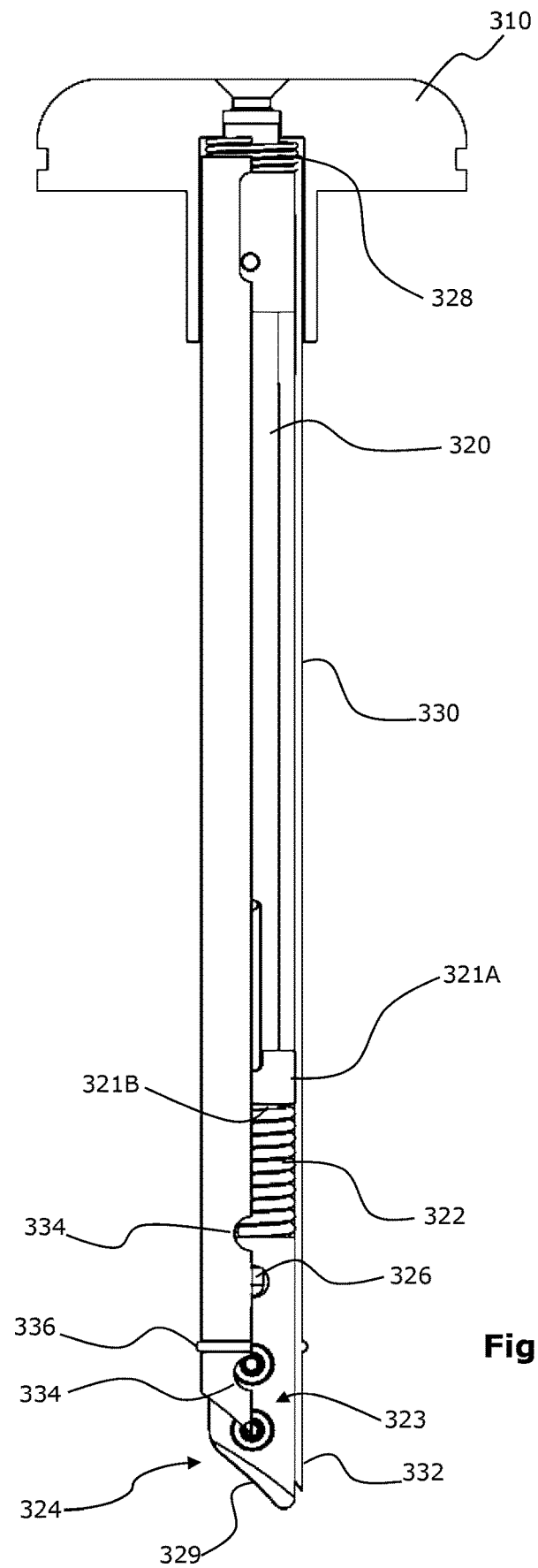
FIG. 21 is a rendered side view of the obturator assembly of FIG. 18 showing the inner stylet in a transition between the retracted configuration and an extended configuration in accordance with an embodiment of the invention.
Figure 22:
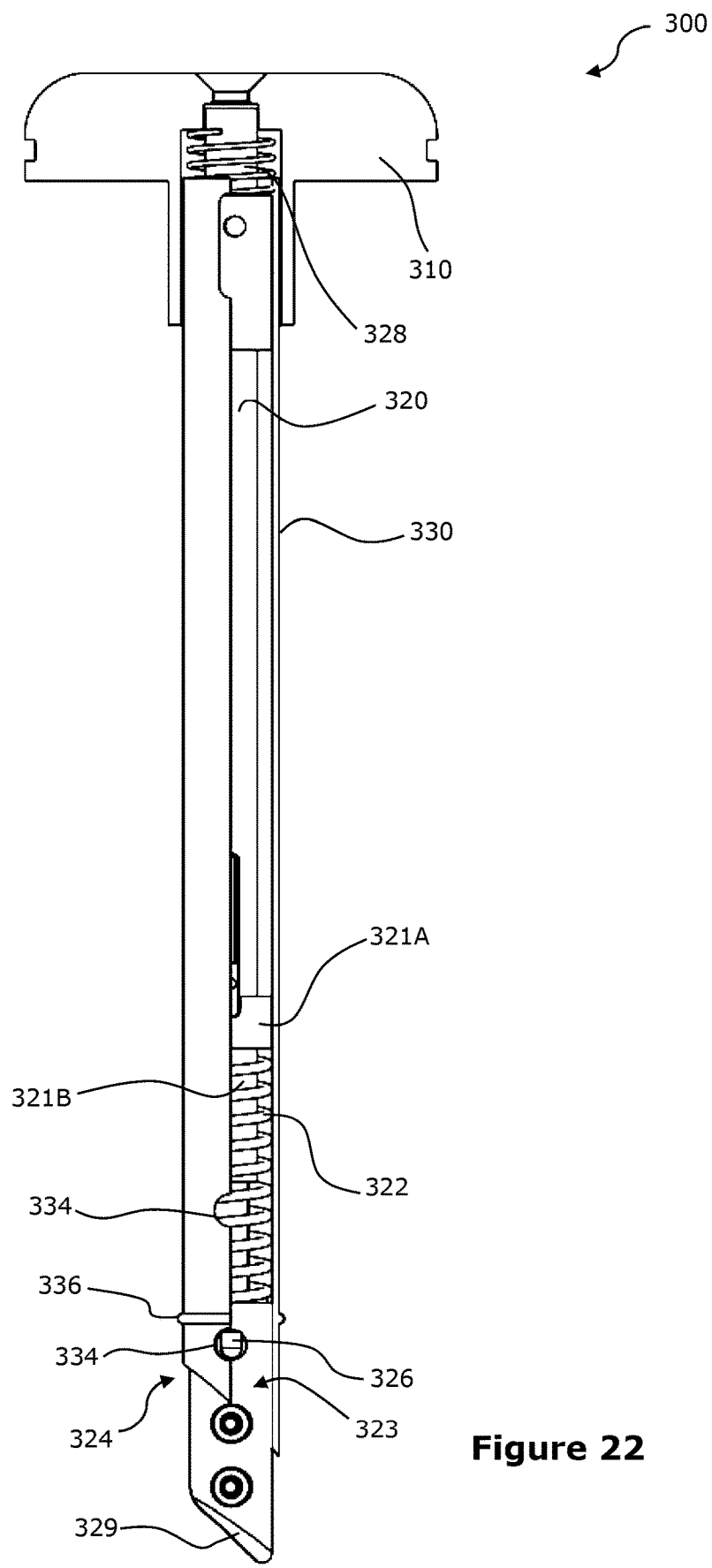
FIG. 22 is a rendered side view of the obturator assembly of FIG. 18 showing the inner stylet in a fully extended configuration in accordance with an embodiment of the invention.

Referring to FIGS. 18 to 27, the obturator assembly 300 comprises a hollow stem 330 having a cutting portion 324 at a distal end. The cutting portion 324 is provided with a cutting blade 332 for piercing through body tissues to reach the pleural cavity. The cutting blade 332 can be shaped as a chamfered blade as shown in FIGS. 20 to 22. It can be said that the chamfered cutting blade has a conical tip. The obturator assembly 300 further comprises an inner stylet 320 housed within the hollow stem 330, the stylet 320 being configured to be movable relative to the stem 330. The stylet 320 is connected at a proximate end to a handle 310 by way of a spring-loaded coupler, so that when actuated, the handle 310 can move relative to the stylet 330. The stylet 320 is connected to a blunt portion 323 located at a distal end of the stylet 320, the blunt portion 323 comprises a blunt member 329. An intermediate portion 321A, 321B connects the stylet 320 to the blunt portion 323. The blunt portion 323 comprises an extendable shaft housed telescopically within a housing tube 321B of the intermediate portion. A biasing means in the form of a spring 322 is arranged between the stylet 320 and the blunt portion 323 such that the blunt portion 323 is biased to move away from the stylet 320 and extend outwards past the cutting portion 324 of the hollow stem 330 as shown in FIGS. 20 to 22 and 27.

The relative positions of the blunt portion 323 and the cutting portion 324 of the hollow stem 330 can be locked by way of complementary protrusion and aperture formations. In one configuration as shown in FIGS. 20 to 22, the blunt portion 323 is configured with one or more protrusions 326 and the cutting portion 324 of the stem 330 is configured with apertures 334 spaced along the longitudinal axis of stem 330. As the blunt portion 323 is moved downward (toward the distal end of the stem 330) by force transmitted through the handle 310, the protrusion 326 of the blunt portion 323 engages with complementary shaped apertures 334 to lock the blunt portion 323 in place by friction. It is to be appreciated that the obturator assembly 300 can be actuated by pushing the handle 310 so that the obturator assembly 300 transforms from a retracted cutting configuration in which the blunt portion 323 is retracted and locked wholly within the stem 330, to an extended configuration in which the blunt portion 323 is locked in an extended position past the cutting portion 324 of the stem 330.

Figure 23A:
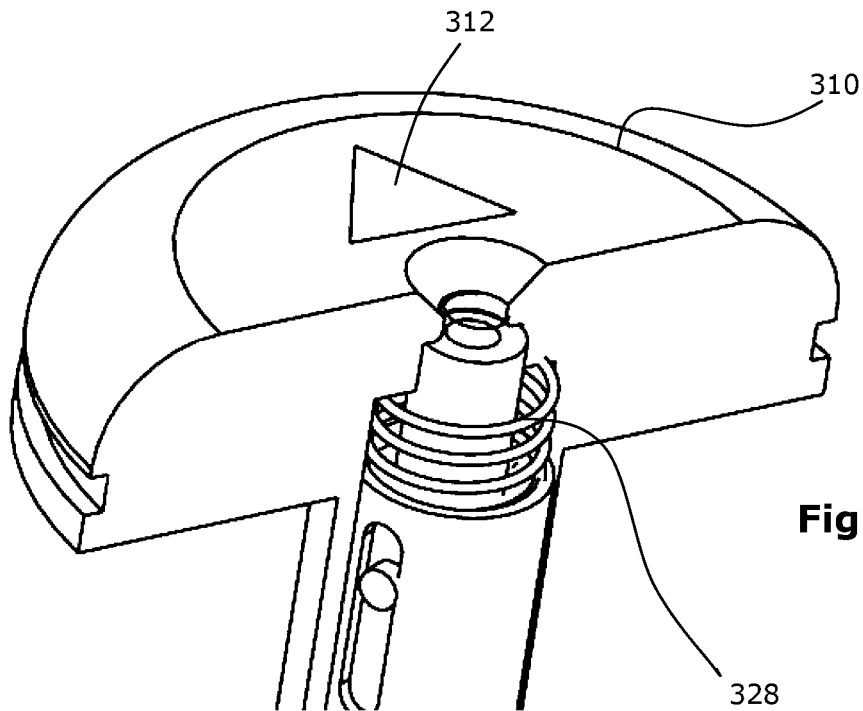
FIGS. 23A and 23B are rendered close up perspective views showing the handle of the obturator assembly of FIG. 19.
Figure 23B:
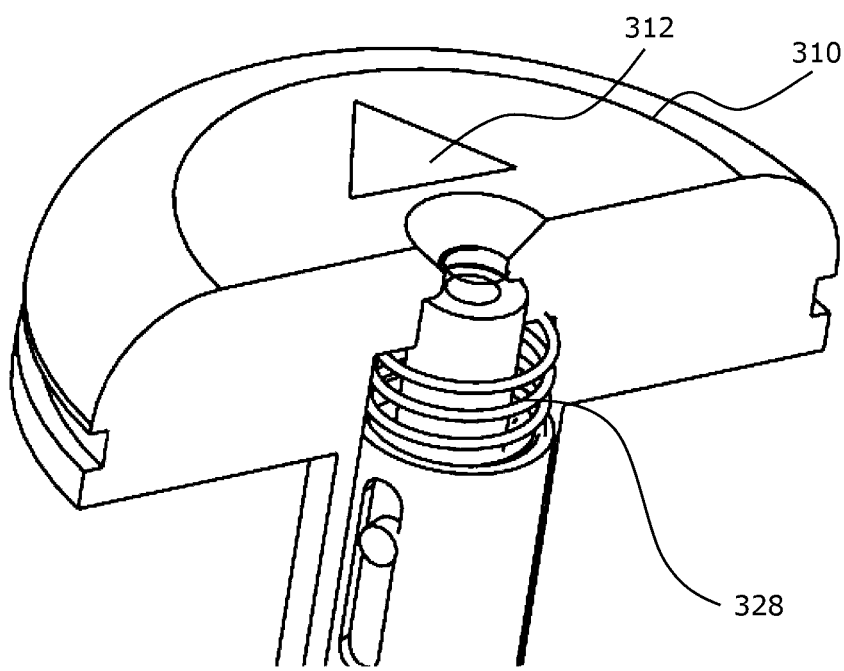
Figure 24:
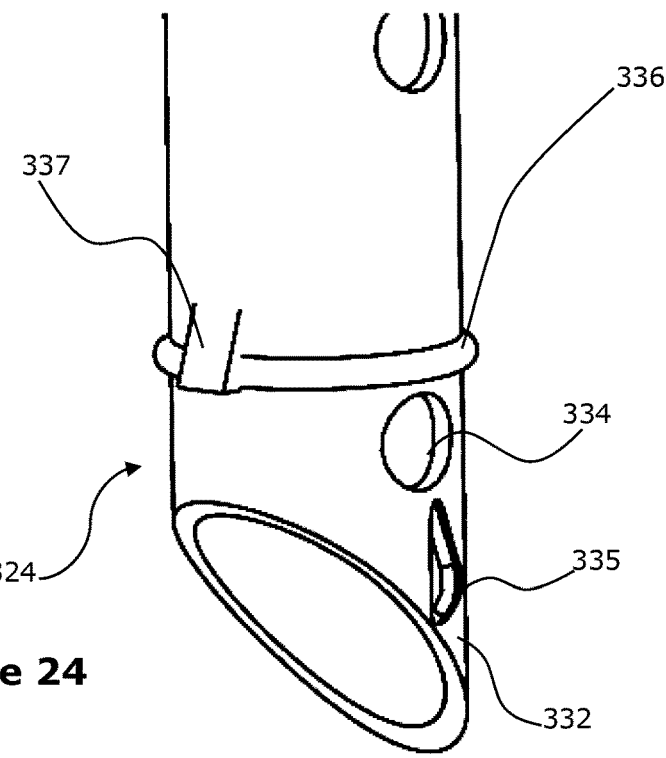
FIG. 24 is a rendered close up perspective view of a cutting portion of the obturator assembly of FIG. 19 showing a cannula release mechanism in accordance with an embodiment of the invention.

As shown in FIGS. 23 and 24, the handle 310 is coupled to the stylet 320 by way of a spring 328 connection. The spring 328 biases the handle 310 back towards its original position when force no longer applies on the handle 310. Furthermore, pushing the handle 310 has the effect of unlocking the blunt portion 323 of stylet 320 from its first locked position as shown in FIG. 21. Alignment indicators 312 can be provided to the handle 310 to assist with alignment of the obturator assembly 300 to the valve assembly 200 prior to insertion. In some configurations, the handle 310 is provided with rubber material for ease of handling and gripping by the operator.

Figure 25:
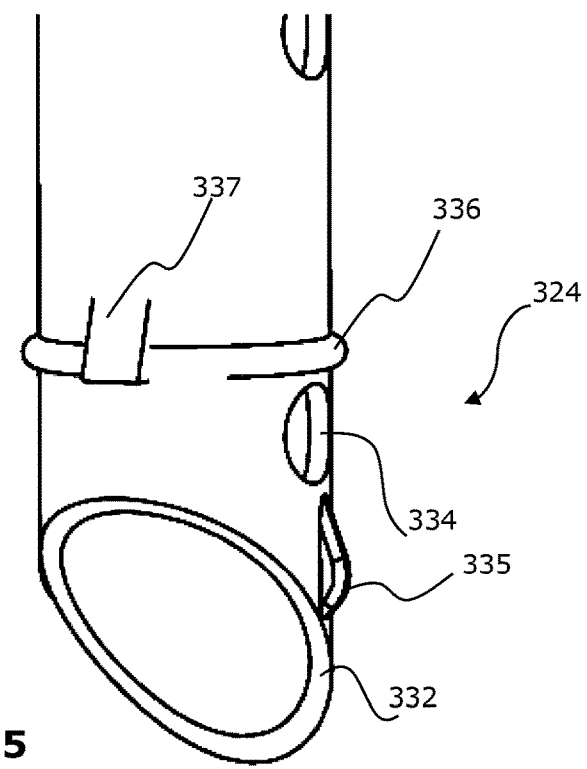
FIG. 25 is a rendered close up perspective view showing the cannula release mechanism of FIG. 24.
Figure 26:
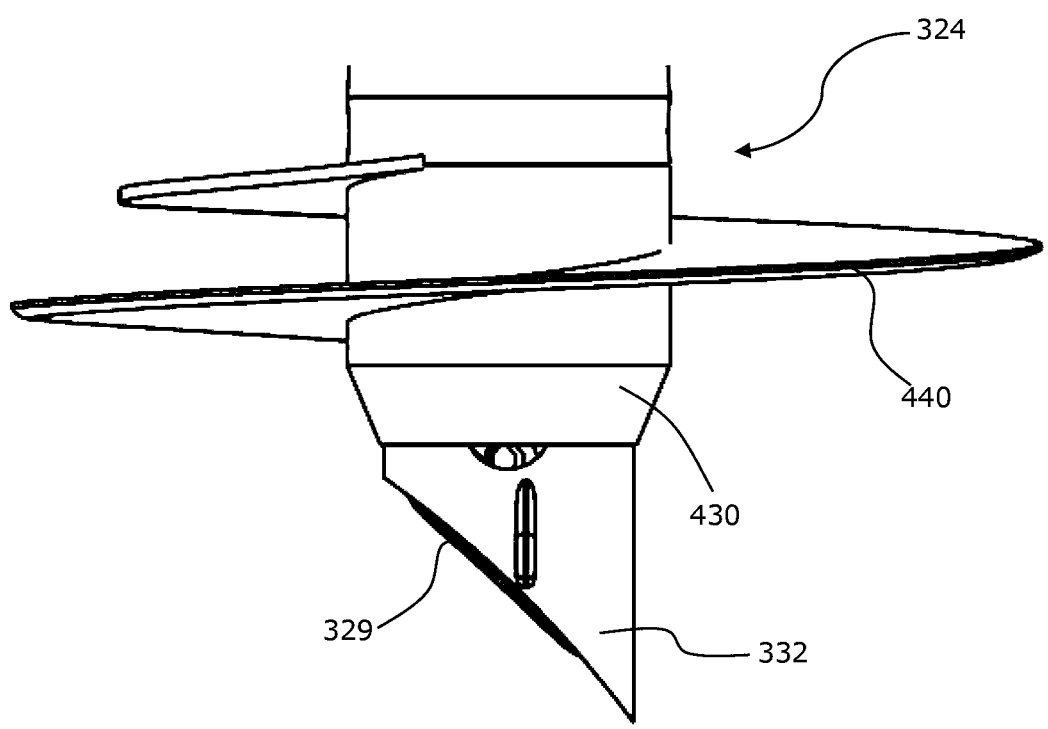
FIG. 26 is a rendered close-up side view showing a cannula mounted proximate the cutting portion of the obturator assembly in accordance with an embodiment of the invention.
Figures 27A, 27B, 27C:
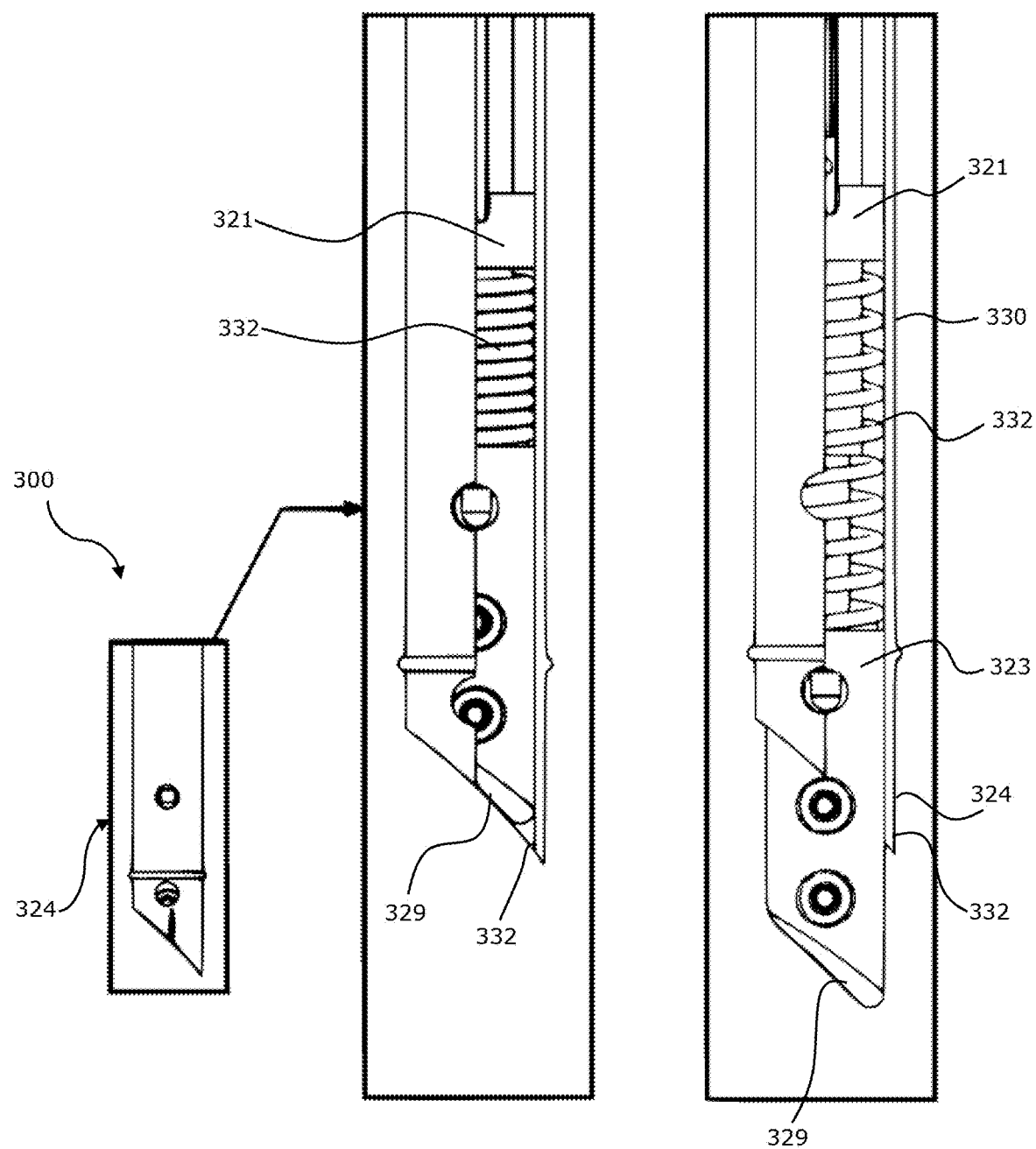
FIG. 27 is a series of close up schematic sectional side views showing an inner stylet in a retracted configuration and a fully extended configuration in accordance with an embodiment of the invention.

The cannula 400 is detachably coupled to the cutting portion 324 of the hollow stem 330 for deploying into the pleural space of the patient as the cutting portion 324 pierces through the chest tissues at the intercostal space. The cannula 400 is sized and dimensioned to be received externally on the cutting portion 324 with a flush fitting to reduce unwanted movement of the cannula 400 prior to and during insertion into the pleural cavity of the patient and for ease of coupling with the obturator assembly 300 as described below. Referring to FIGS. 24 to 26, the cannula 400 is mounted at the cutting portion 324 and held in place by coupling mechanism 336, 337 in the form of a protruding rim or ridge 336 around the perimeter of the cutting portion 324 and a protrusion 337 configured such that the cannula can be detached from the cutting portion 324 by withdrawing the obturator assembly 300 relative to the cannula 400. At least one protrusion 335 in the form of a ridge located adjacent and/or perpendicular to the cutting blade 332 may be provided to serve the function of a blunt dissector to assist with blunt separation of longitudinal muscle fibres as the obturator assembly 300 cuts through the chest wall tissues, whereby, a clean passage of the obturator assembly 300 is provided. In one configuration, two protrusions 335 are provided perpendicular to the cutting blade 332.

The cannula 400, once deployed, establishes a connection between the pleural space of the patient and the valve assembly 200, and can be used as an access port for insertion of an intercostal catheter or video endoscope after removal of the obturator assembly 300, with the resulting ability to control intra-pleural pressure via air insufflation or venting via the valve and to allow targeted examination and evacuation of the pleural cavity under direct vision, i.e. pleuroscopy/thoracoscopy.

Figure 28:
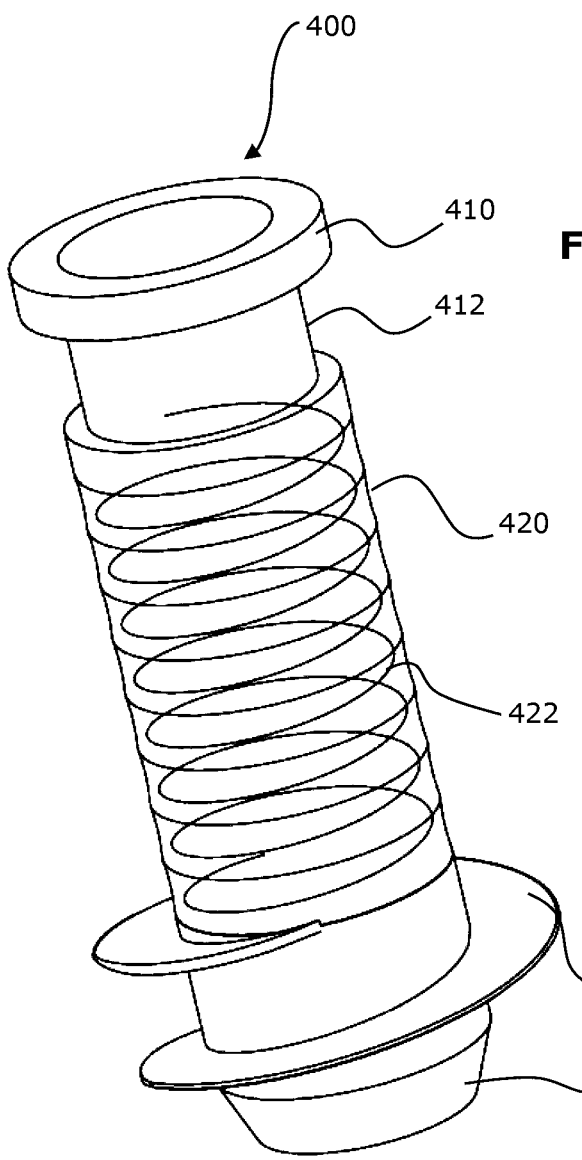
FIG. 28 is a rendered perspective view showing a cannula in accordance with an embodiment of the present invention.
Figure 29:
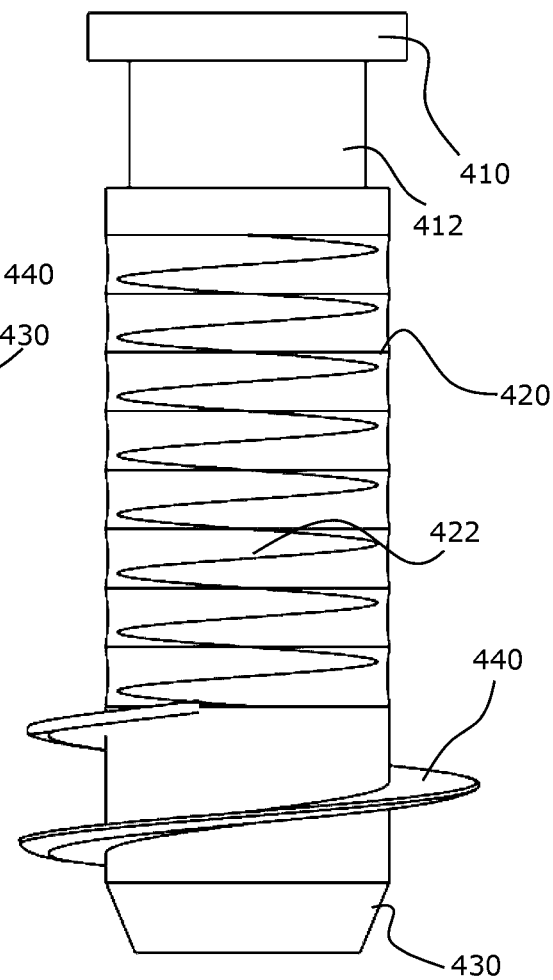
FIG. 29 is a rendered front view showing the cannula of FIG. 28 in a retracted configuration in accordance with an embodiment of the invention.
Figure 30:
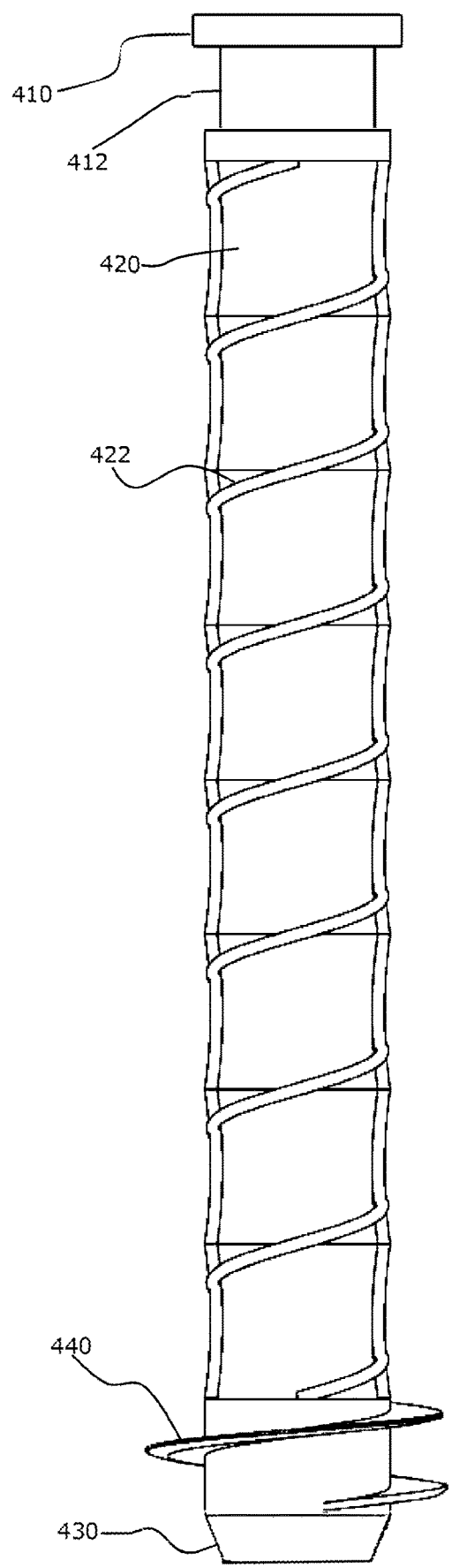
FIG. 30 is a rendered front view showing the cannula of FIG. 28 in an extended configuration in accordance with an embodiment of the invention.
Figure 31:
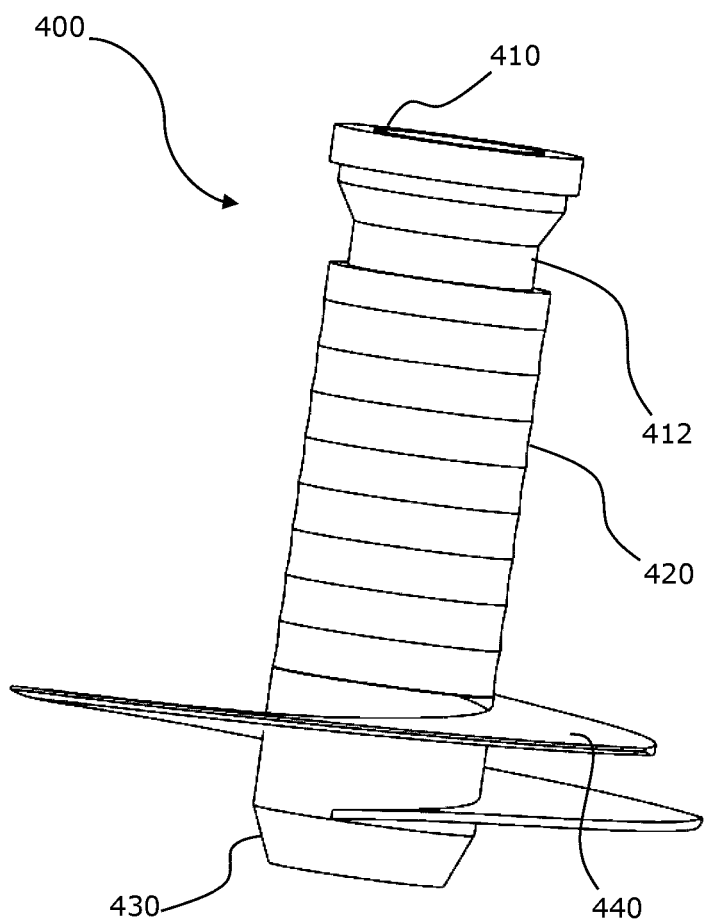
FIG. 31 is a rendered perspective view showing a cannula in accordance with another embodiment of the present invention.
Figure 32:
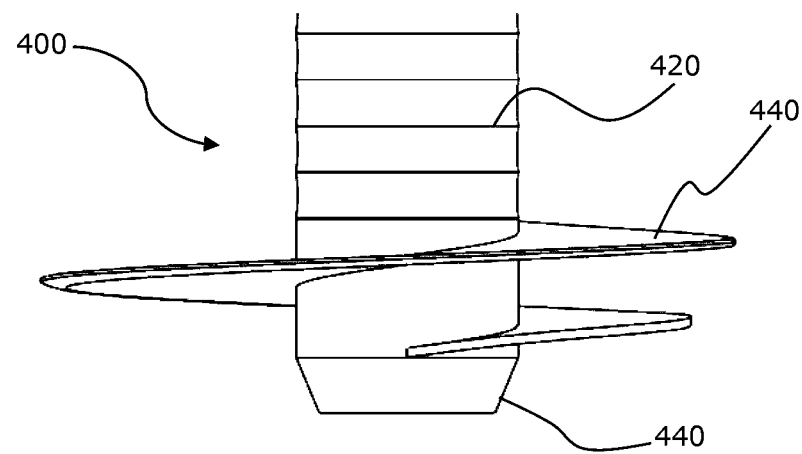
FIG. 32 is a rendered close up front view of the cannula of FIG. 31 showing an enlarged helical flange.
Figure 33:
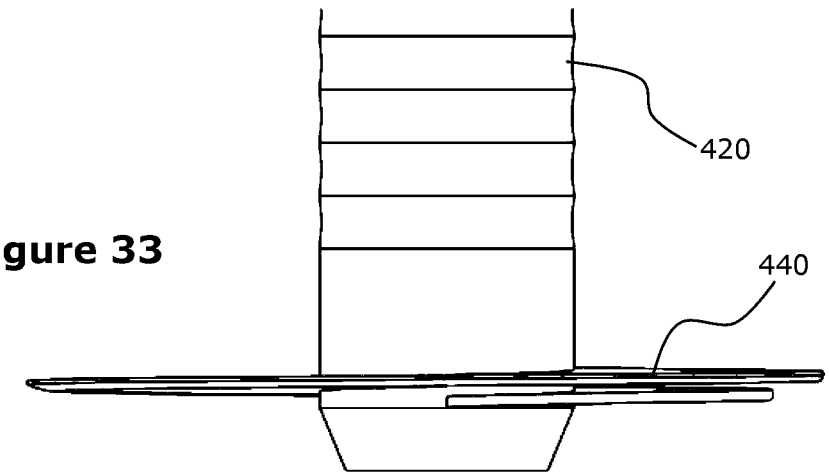
FIG. 33 is a rendered close up front view of a cannula showing a helical flange in accordance with another embodiment of the present invention.
Figure 34A:
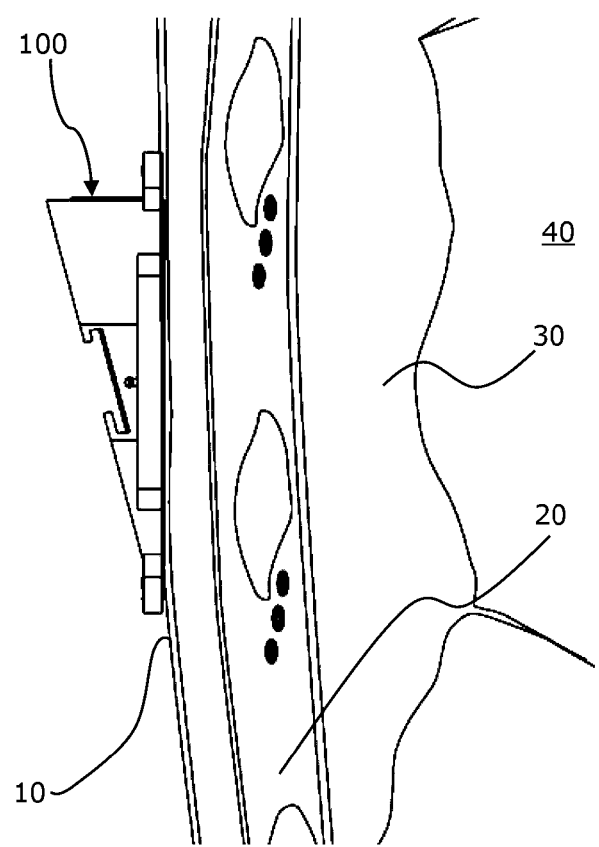
FIGS. 34A to 34G are schematic illustrations showing the steps of deploying a surgical pleural decompression system according to an embodiment of the invention.
Figure 34B:
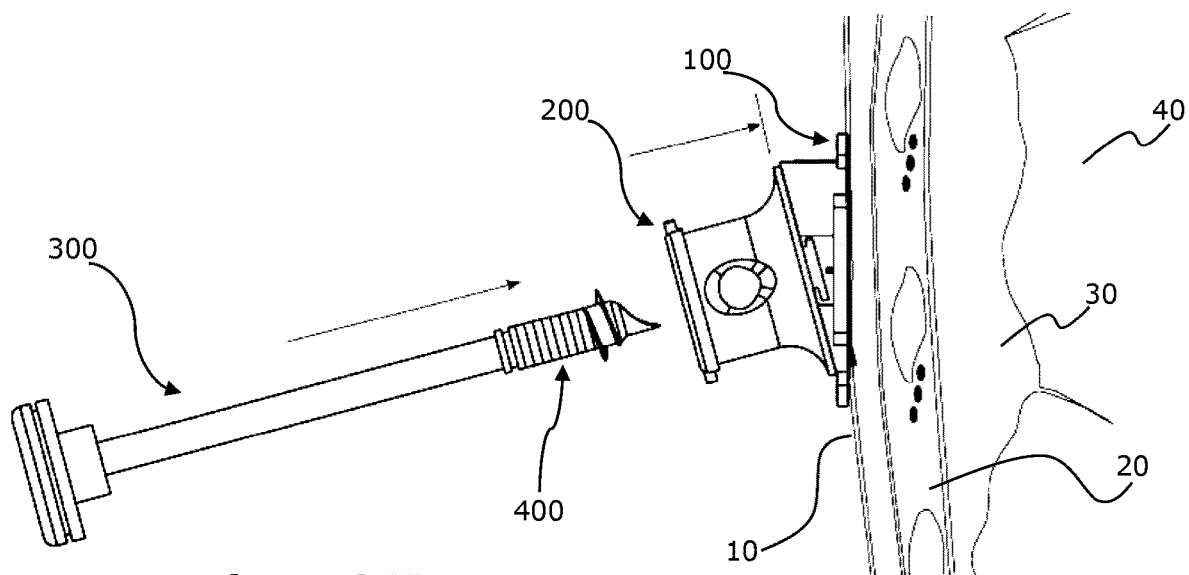
Figure 34C:
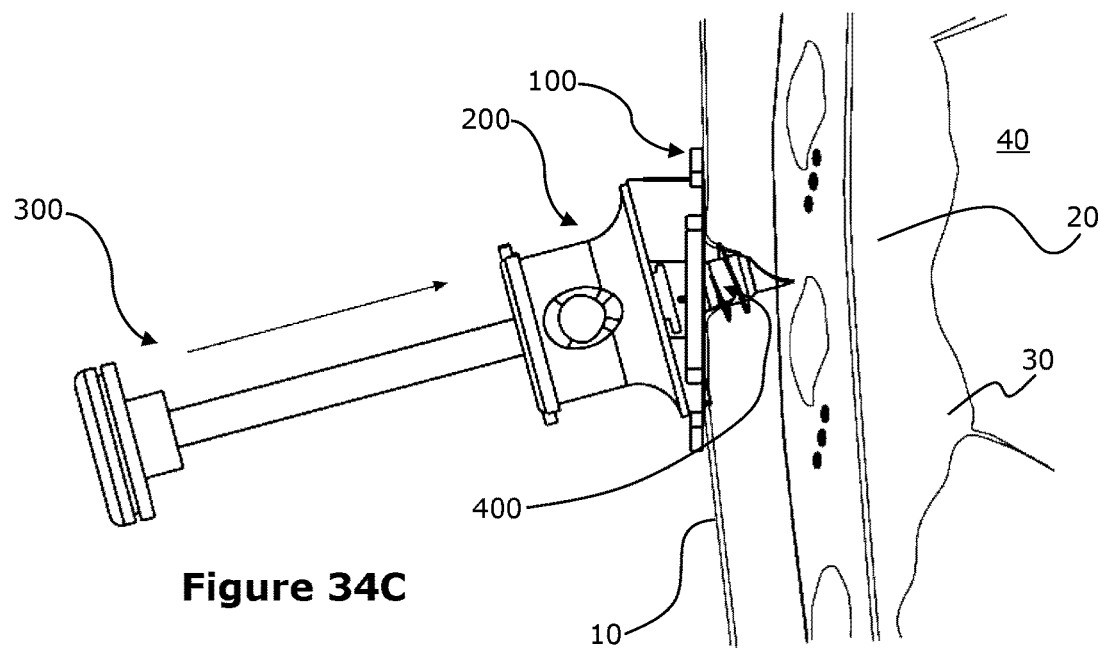
Figure 34D:
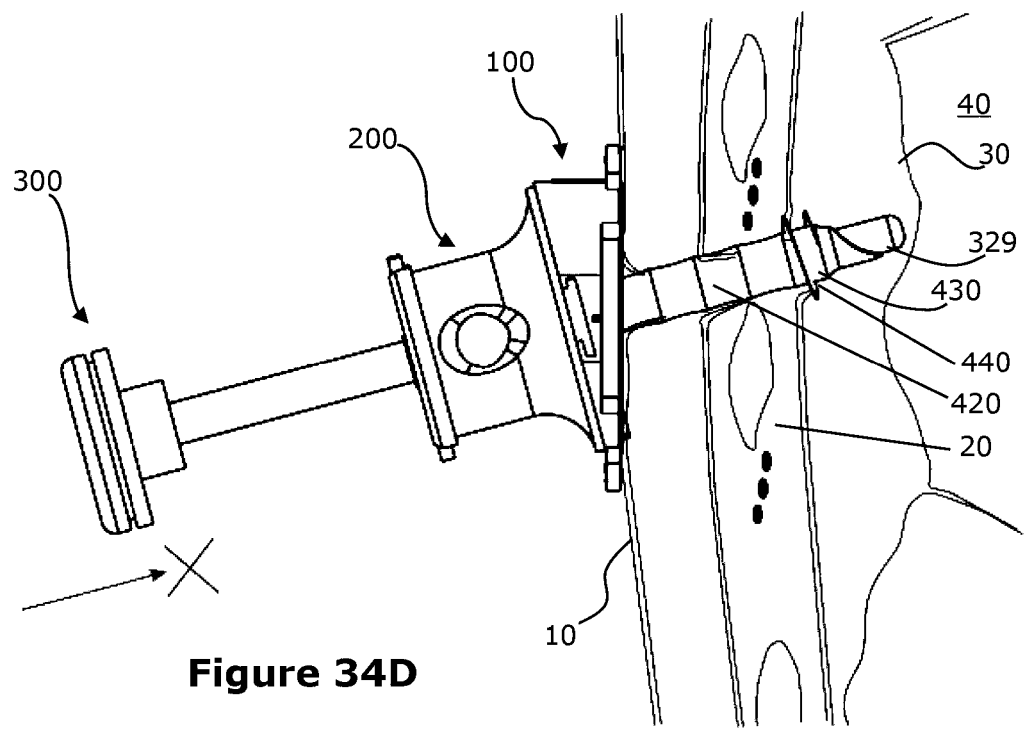
Figure 34E:
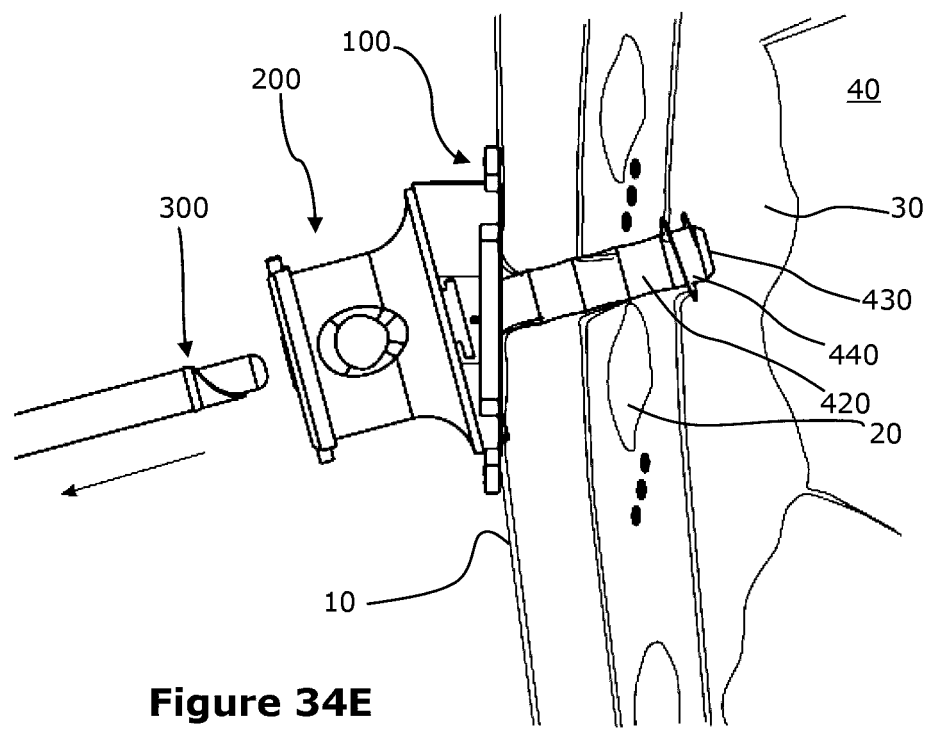
Figure 34F:
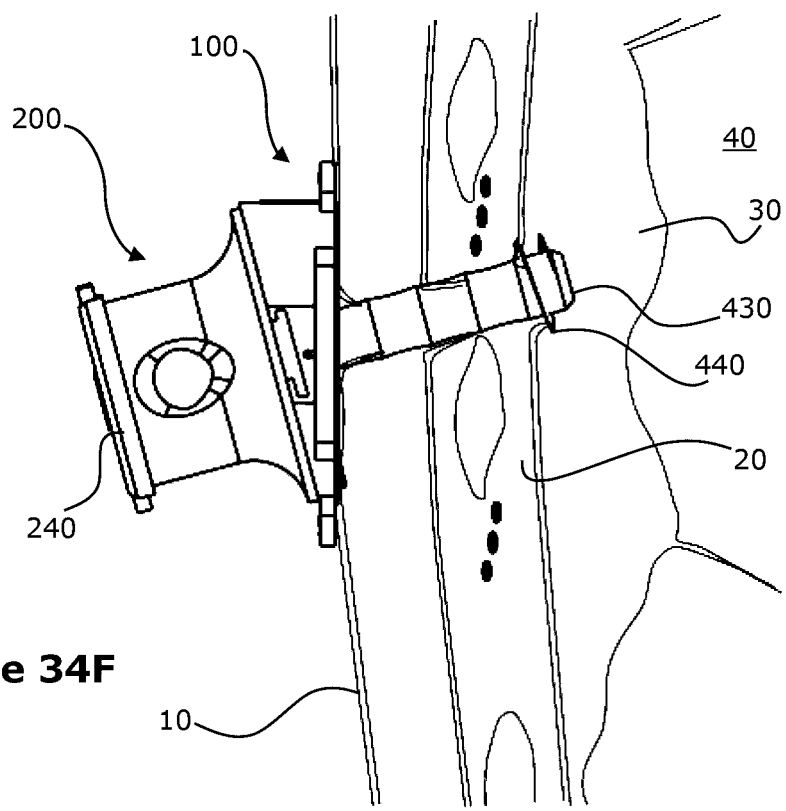
Figure 34G:
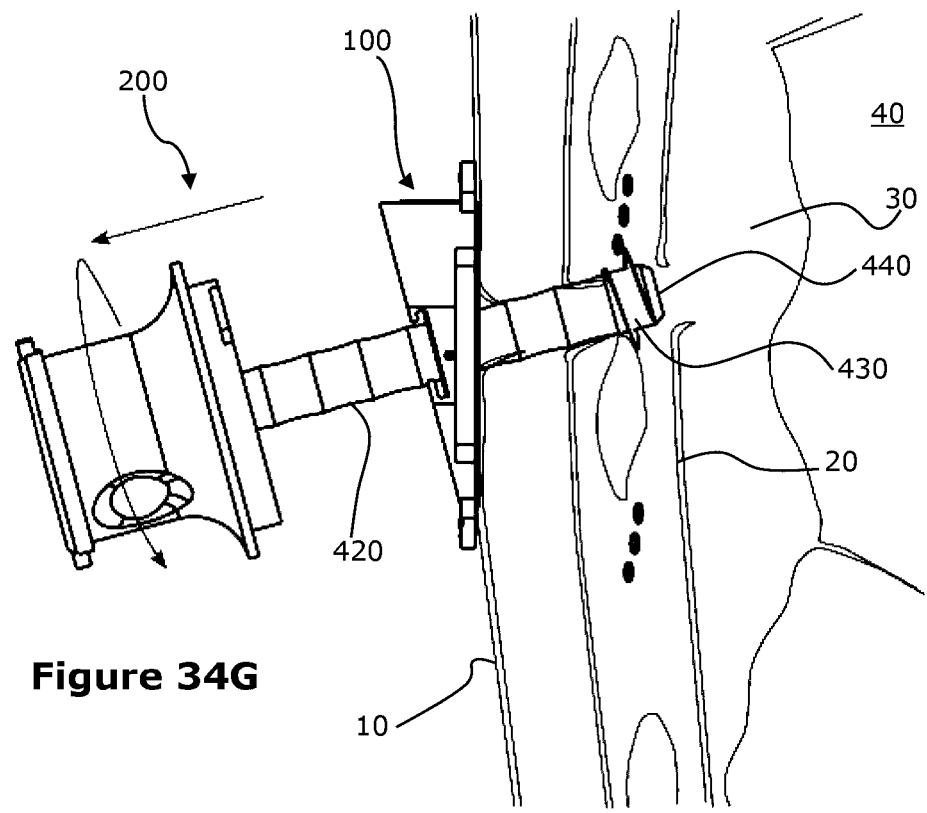
Figure 35:
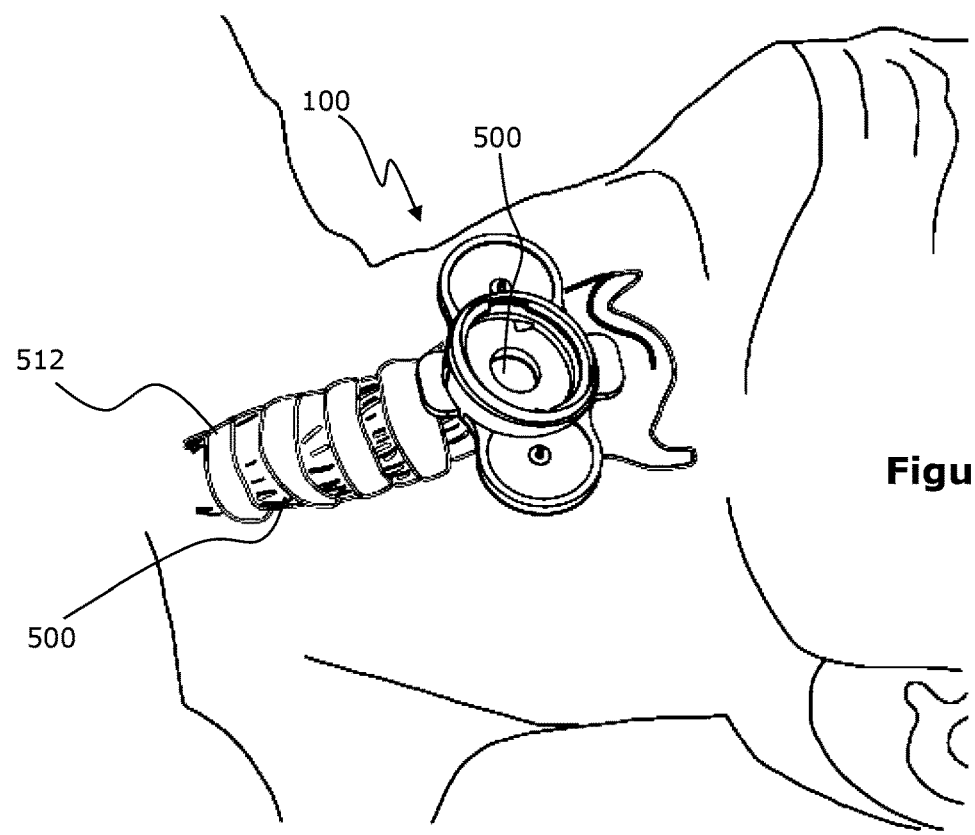
FIG. 35 is a schematic illustration showing a base according to an embodiment of the invention for deployment external and adjacent a patient's trachea.
Figure 36:
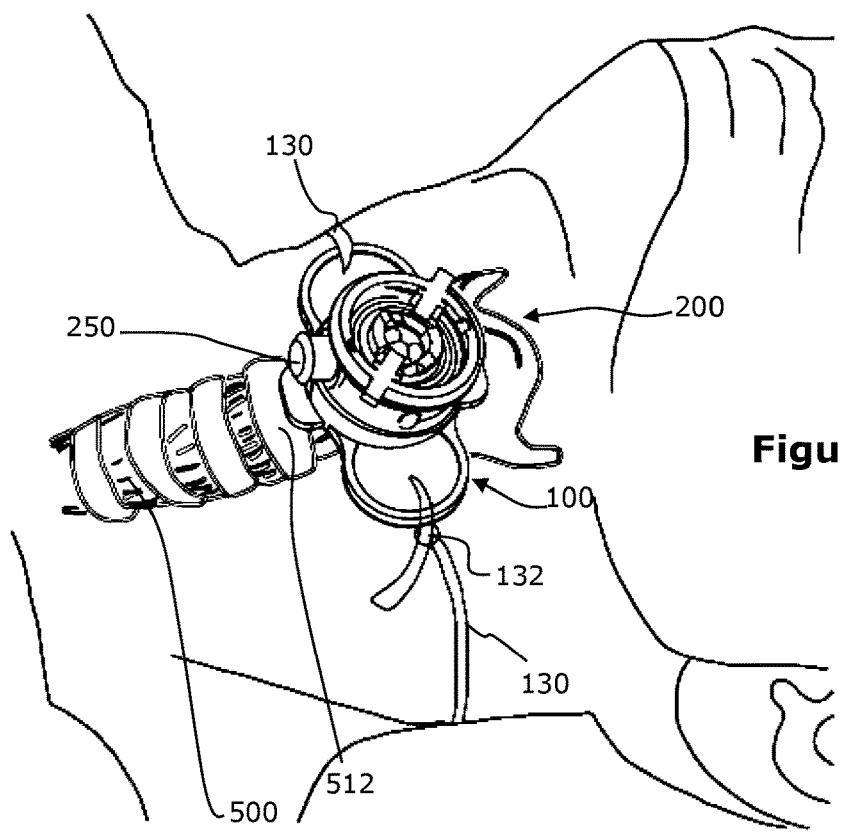
FIG. 36 is a schematic illustration showing a valve assembly according to another embodiment of the invention coupled to the base of FIG. 35.
Figure 37:
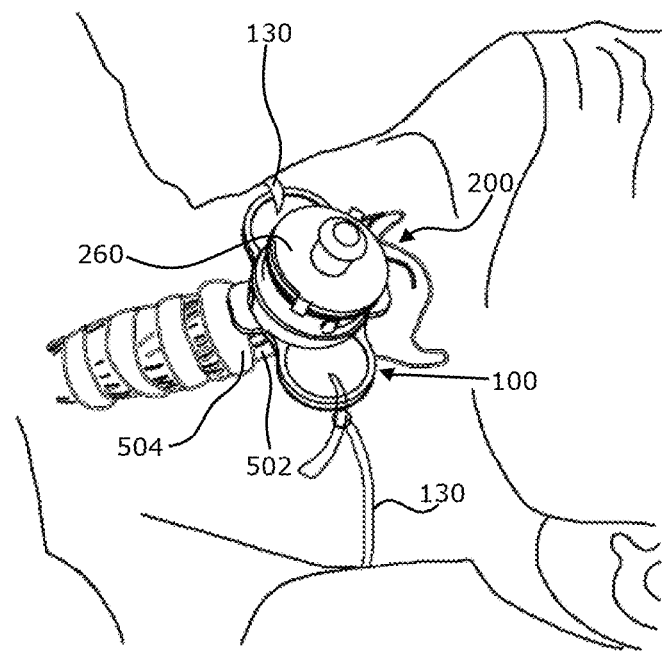
FIG. 37 is a schematic illustration showing a ventilation port according to another embodiment of the invention coupled to a valve assembly and a base deployed external and adjacent a patient's trachea.
Figure 38A:
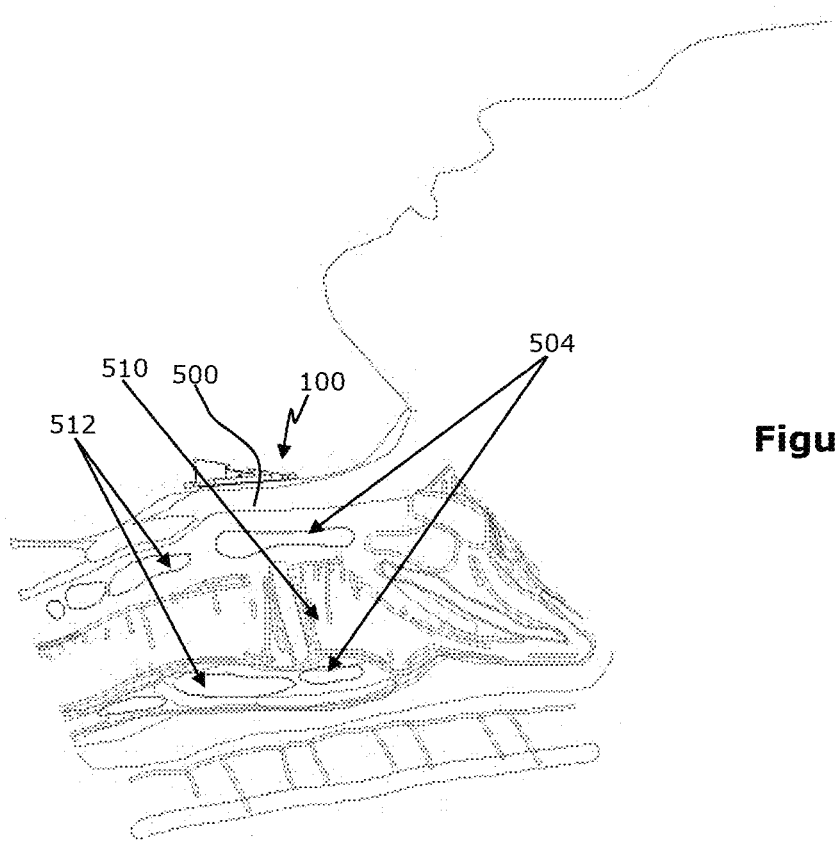
FIGS. 38A to 38E are schematic illustrations showing the steps of deploying a surgical system according to another embodiment of the invention for use in cricothyroidotomy.
Figure 38B:
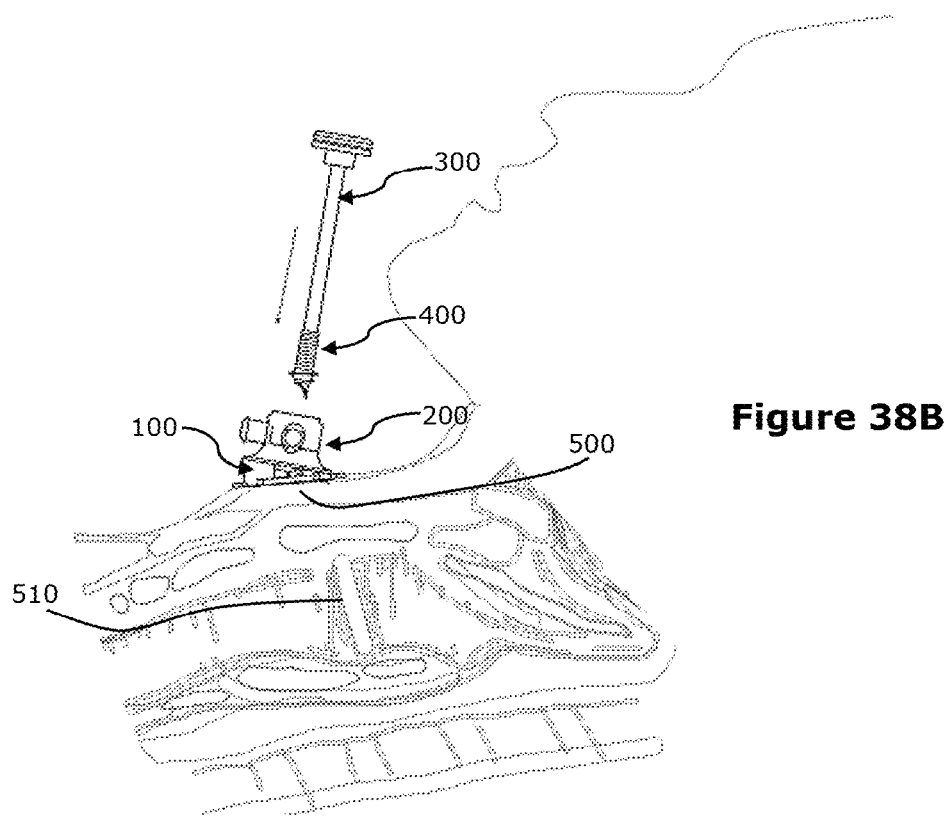
Figure 38C:
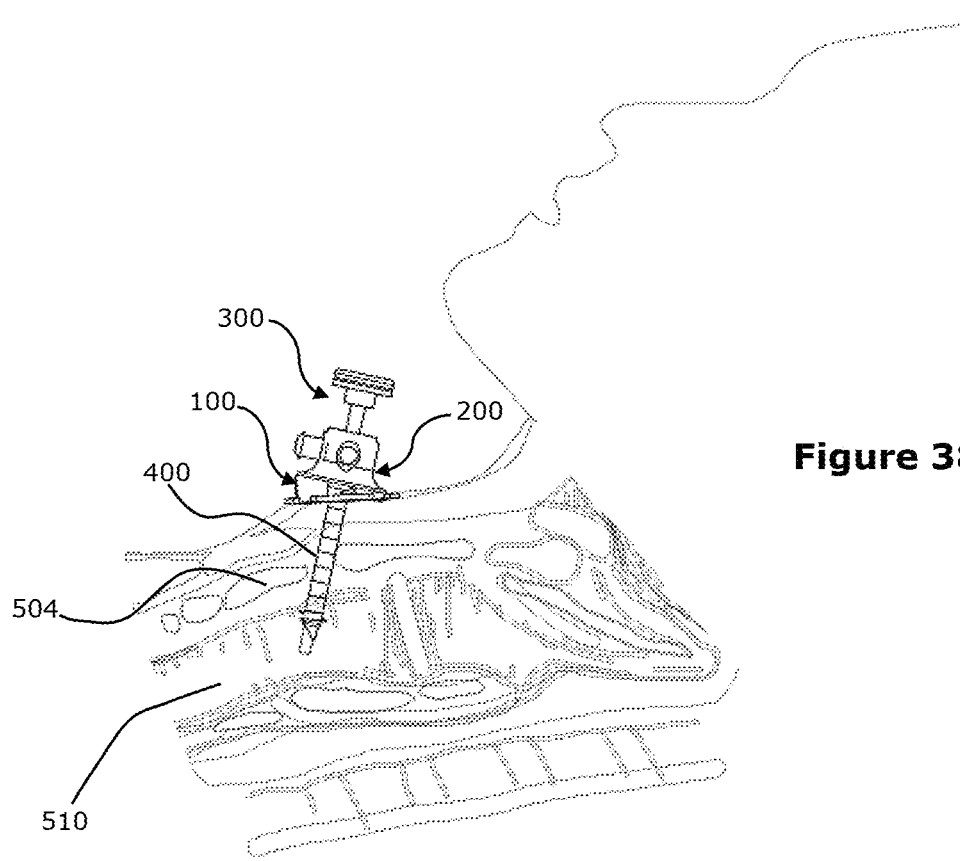
Figure 38D:
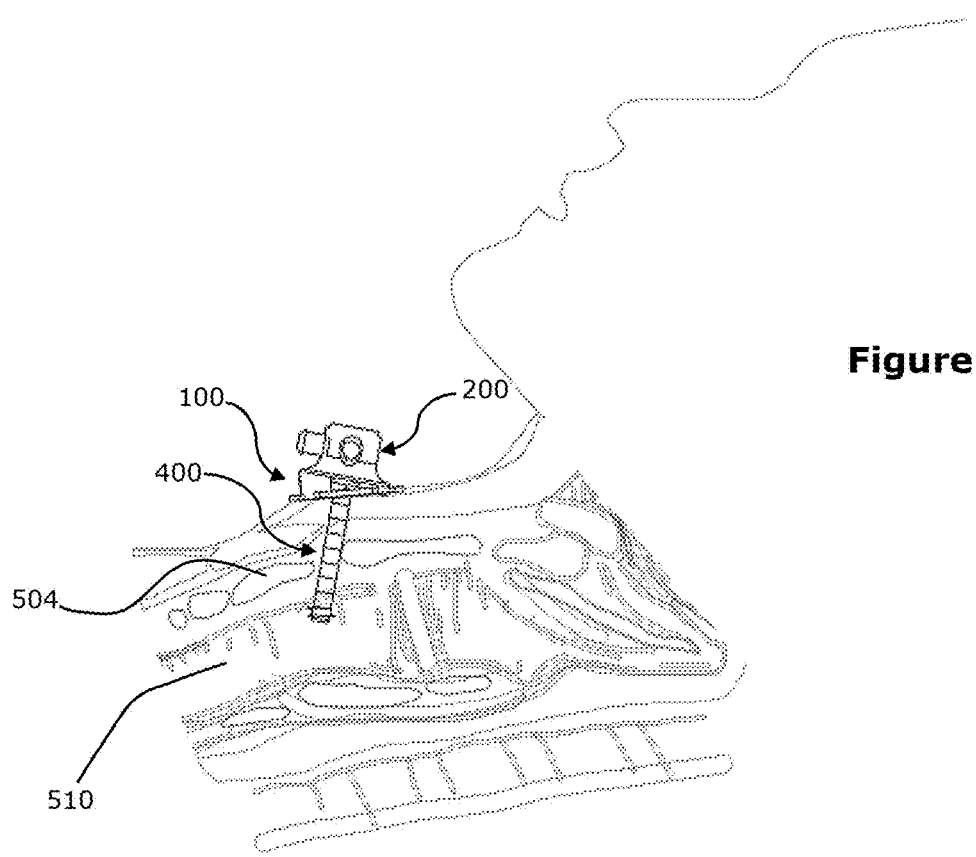
Figure 38E:
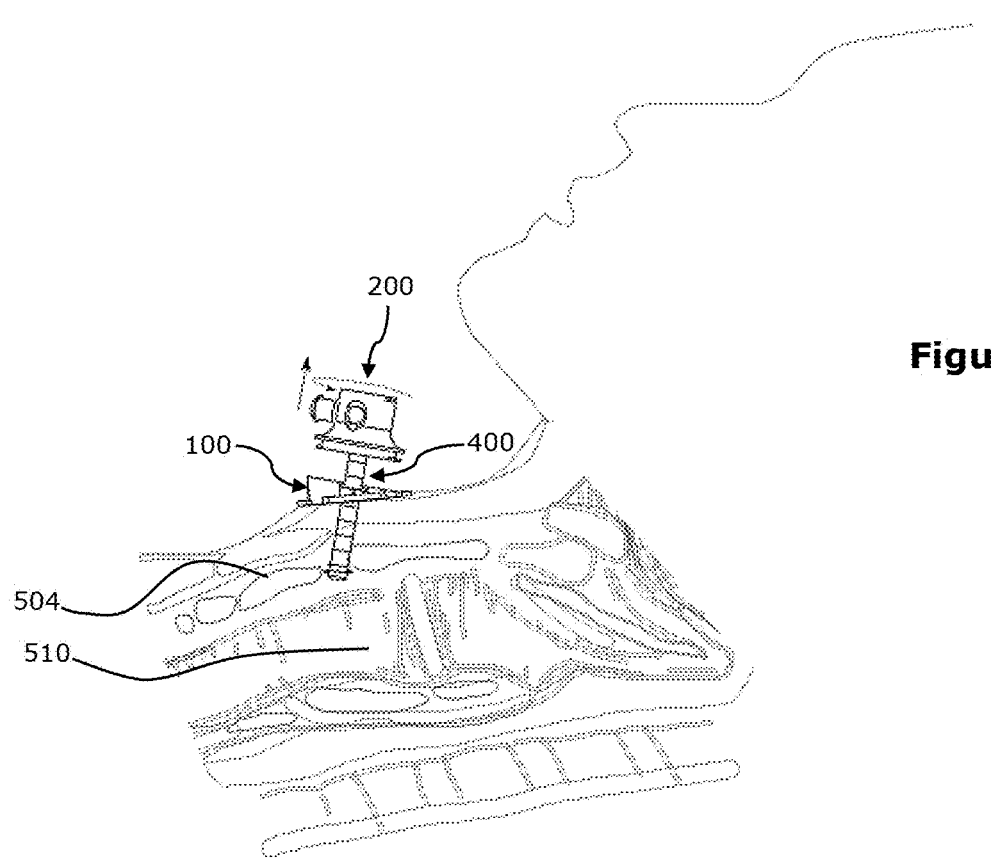
Figure 39A:
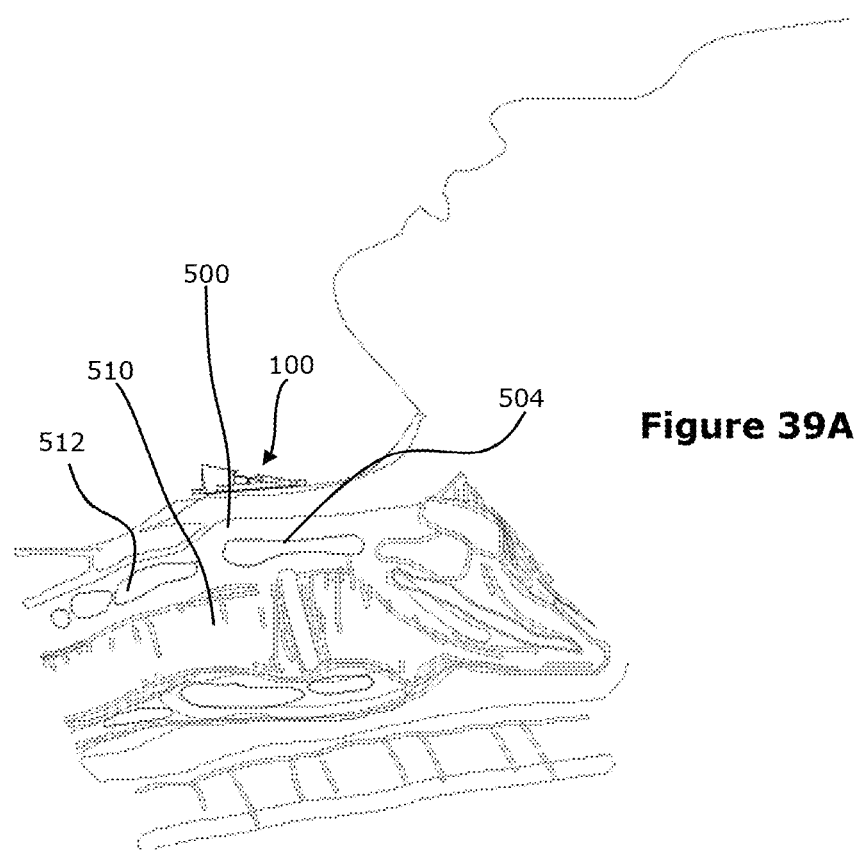
FIGS. 39A to 39E are schematic illustrations showing the steps of deploying a surgical system according to a preferred embodiment of the invention for use in cricothyroidotomy.
Figure 39B:
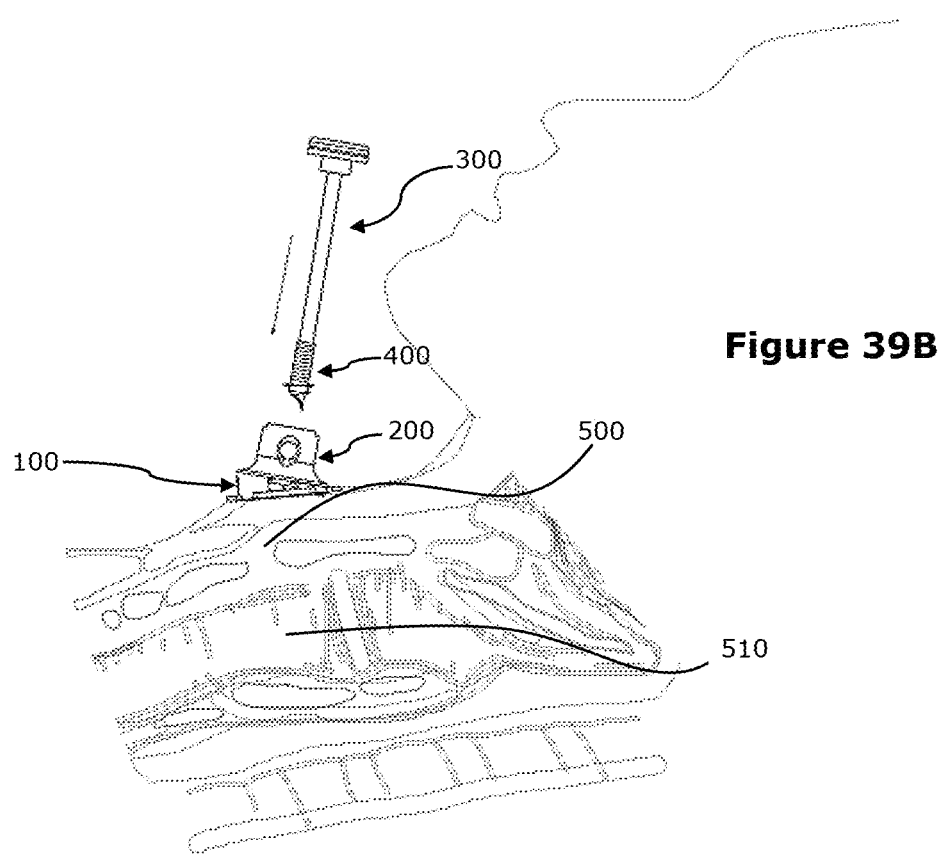
Figure 39C:
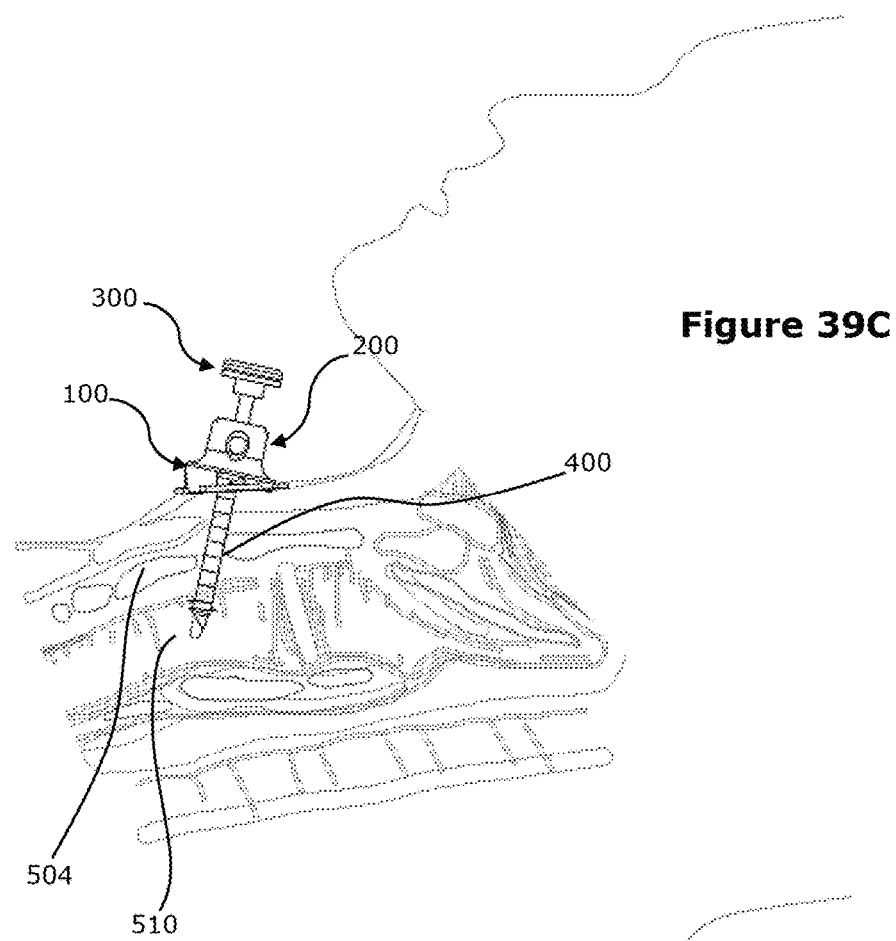
Figure 39D:
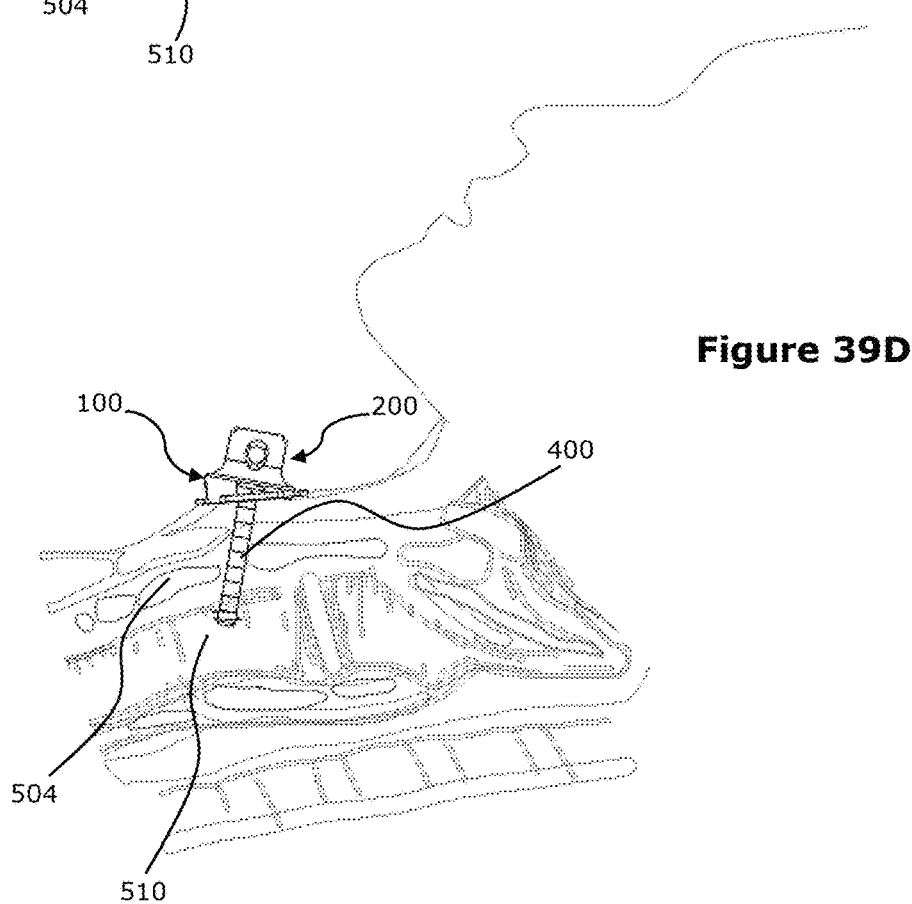
Figure 39E:
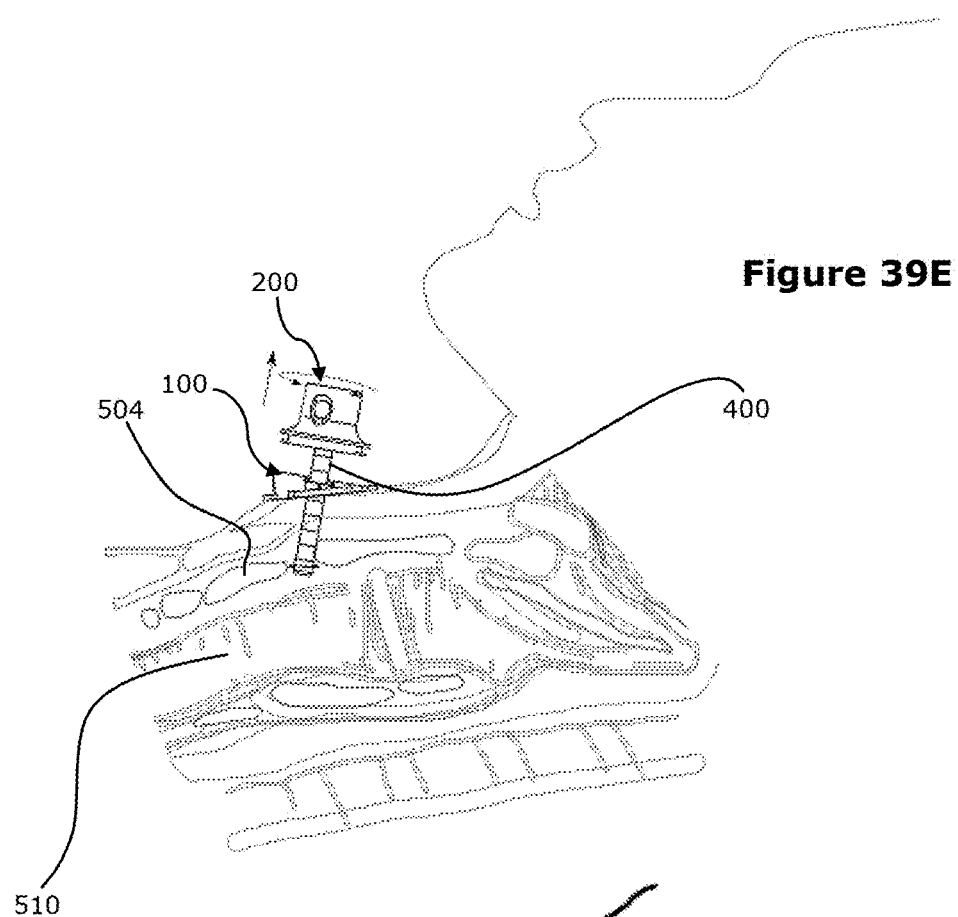
Figure 40A:
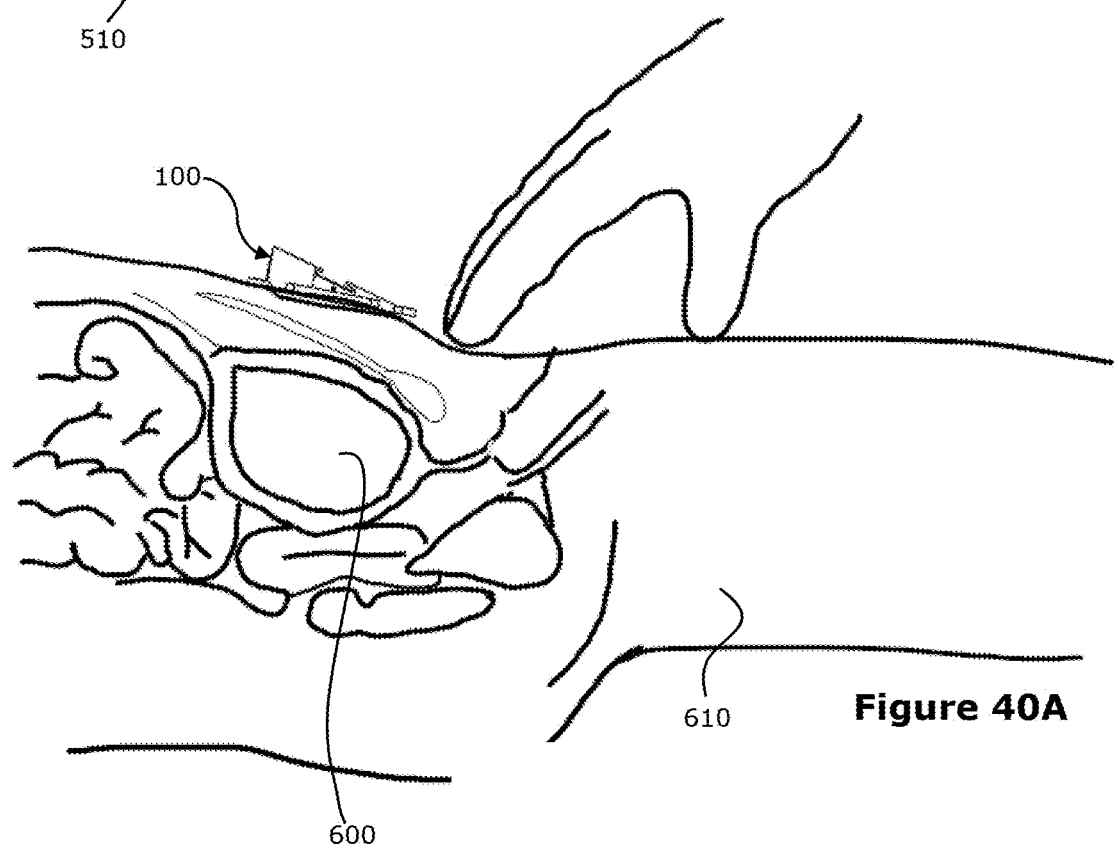
FIGS. 40A to 40E are schematic illustrations showing the steps of deploying a surgical system according to a preferred embodiment of the invention for use in treating obstructed urethra.
Figure 40B:
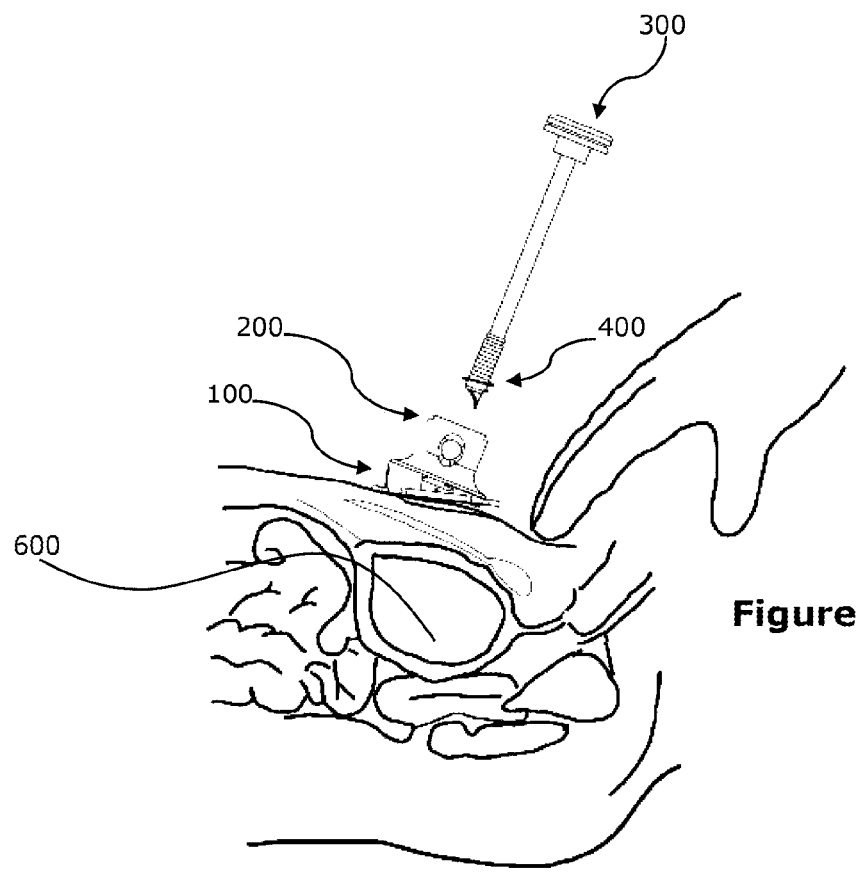
Figure 40C:
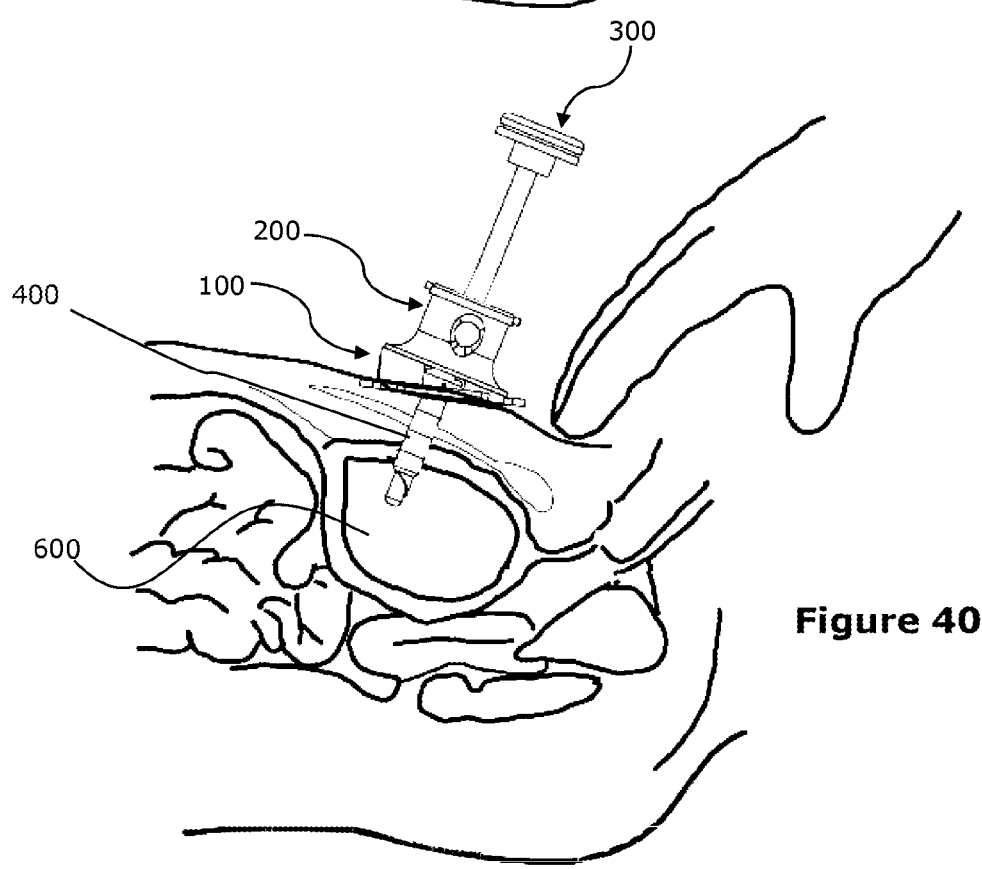
Figure 40D:
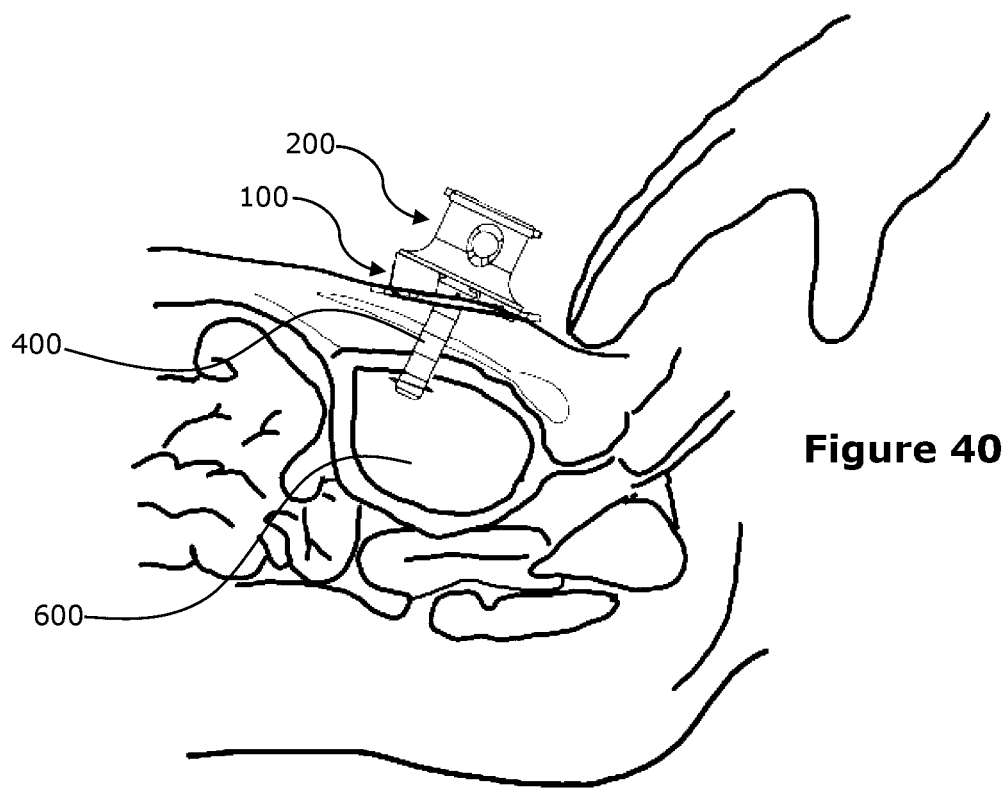
Figure 40E:
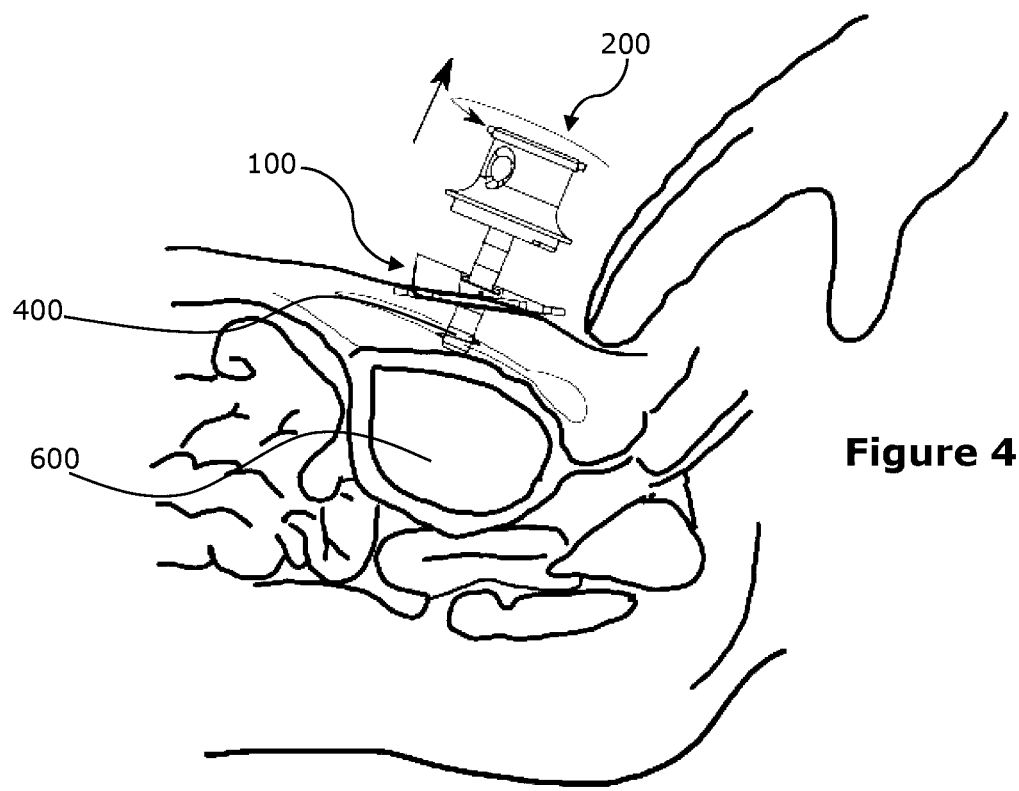

Referring to FIGS. 28 to 30, the cannula is a tube having a proximate end 410 and a distal end 430 for establishing a path between a pleural cavity and the valve assembly 200 for pleural fluid extraction in use. The cannula comprises a locking portion 412, an anchoring portion 440 and a lengthwise extendable body 420 extending therebetween. The distal end 430 of the cannula 400 is provided with a tapered head, tapering from a reduced diameter to a larger diameter of the cannula body 420. This feature allows the cannula to engage and open the locking mechanism 210 of the valve assembly 200 as the cannula passes through the valve assembly 200. The locking portion 412 is sized and dimensioned to be received and held by the locking mechanism 210 with the larger diameter of the proximate end 410 abutting against the top of the locking members 212 as shown in FIG. 15. The anchoring portion 440 can be configured to be in the form of a helical or spiral flange/screw for anchoring the cannula 400 in the chest wall as shown in FIGS. 34D to 34F. The anchoring portion 440 is made from a resilient material such as rubber/silicone so that it can fit through the valve passage 221 and locking mechanism 210 of the valve assembly 200 and the aperture 104 of the base 100, but also retain its flanged shape for anchoring in the chest wall once the cannula enters the thoracic cavity. In embodiments where the anchoring portion 440 is a helical flange, the flange would be operable between an anchoring configuration in which the flange is collapsed in the longitudinal direction, and an extraction configuration in which the flange is extended in the longitudinal direction. In one configuration, the anchoring portion 440 is made from a sterile inert rubber material. The anchoring portion 440 which is part of the cannula assembly (FIG. 31) can be removed by rotating counter-clockwise (unscrewing) and pulling the cannula (attached to the valve assembly 200) from its anchored position in the chest wall. FIGS. 31 to 33 show different embodiments of the anchoring portion 440, including an anchoring portion 440 having an elongated helical flange and an anchoring portion 440 with a disc-like configuration.

The cannula body 420 is extendable lengthwise along its longitudinal length as shown in FIGS. 29 and 30. In one embodiment, a coiled spring 422 is mounted around the cannula body 420 to provide a bias around the body to move towards an extended configuration. The cannula 400 is thus advantageously configured to have a minimum length of about 4 cm and a maximum length of about 8.5 cm. In another embodiment, the cannula 400 is configured to have a minimum length of about 4 cm and a maximum length of about 9 cm. This feature allows the pleural decompression system 1 to establish a path between the pleural cavity and the valve assembly 200 for pleural fluid extraction despite inter-population differences in chest wall thickness. While the extendable body is described to be configured with a coiled spring 422, other suitable configurations may also be used, with non-limiting examples including telescopically walled cannula bodies. It is to be appreciated that owing to the extendable nature of the cannula body 420, the cannula 400 can be configured with a number of different minimum and maximum lengths without departing from the spirit of the invention.

Figure 47:
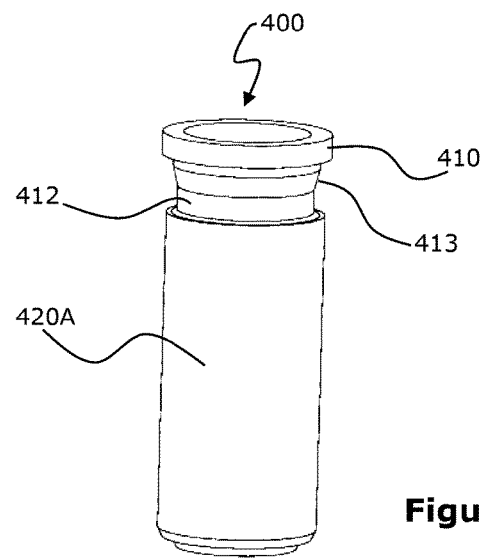
FIG. 47 is a rendered perspective view of a telescopic cannula in accordance with an embodiment of the invention showing the cannula in a retracted condition.
Figure 48:
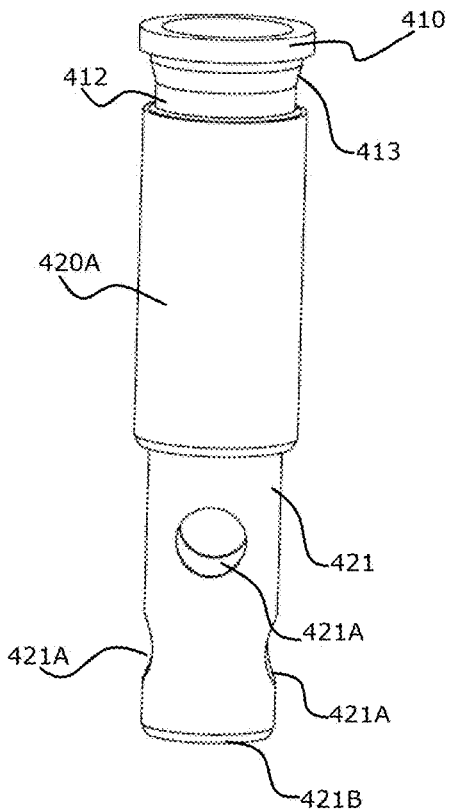
FIG. 48 is a rendered perspective view of the telescopic cannula of FIG. 47 showing the cannula in a partially extended state.
Figure 49:
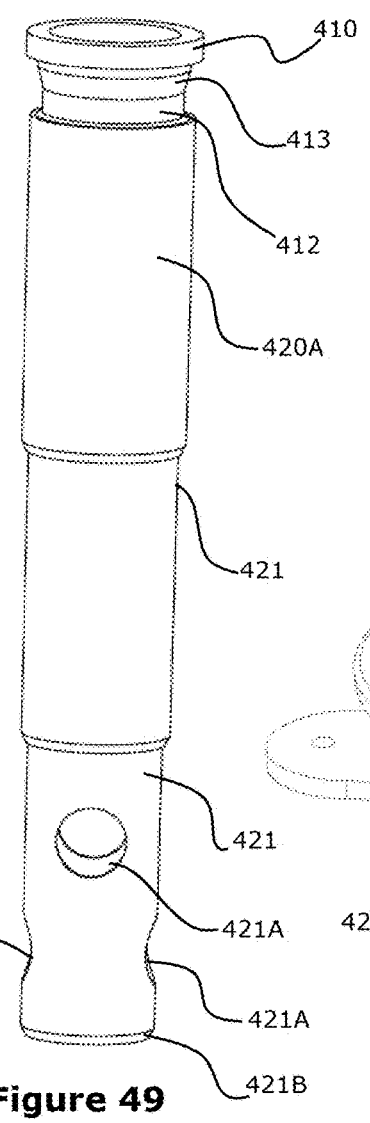
FIG. 49 is a rendered perspective view of the telescopic cannula of FIG. 47 showing the cannula in a fully extended state.

In another embodiment, the cannula 400 can be configured with a telescopic body 420A as seen in FIGS. 47 to 49. The telescopic body 420A may be configured to house a number of sections or stages 421 such that the body 420A is configurable between a retracted, compact, state as seen in FIG. 46 in which all the telescopic sections 421 are retracted within the body 420A, a partially extended state in which one or some of the sections 421 are extended longitudinally from the body 420A as seen in FIG. 48, and a fully extended state in which all sections 421 are extended from the body 420A as seen in FIG. 49. The top of the cannula 400 may likewise be provided with a groove 412 for coupling with the locking members 212 of the valve assembly 200. In one embodiment, the cannula may also be provided with a tapered portion 413 to allow smooth locking transition between the cannula 400 and the valve assembly 200. The bottom-most cannula section 421 can also be provided with one or more pairs of apertures, also known as "Murphy Eyes" to function as side fluid vents to allow air/fluid to escape. The bottom-most cannula section 421 is also configured to be extended first by an obturator assembly 300 when in use and is accordingly provided with a seat or step 421B for catching on to the protruding ridge 336 of the obturator assembly 300. Each cannula section 421 is further configured such that each section 421, once extended to its full individual sectional length, is locked in place to prevent self-collapse post insertion. In one configuration, the top of each section 421 is provided with a groove portion 424 which locks with a bottom wall of the telescopic body 421A. Radio opaque markings may be provided at the bottom tip of the cannula 400 to help operators determine the extent in which the cannula 400 has been inserted into the body cavity.

Figure 50:
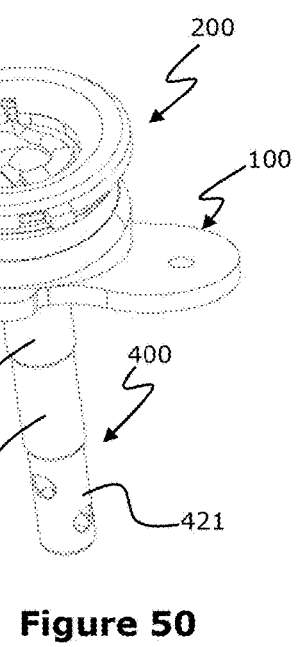
FIG. 50 is a rendered perspective view showing an obturator assembly in accordance with another embodiment of the invention.
Figure 52A:
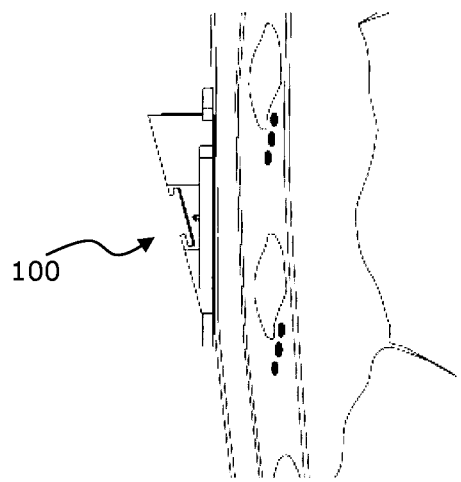
FIGS. 52A to 52G are schematic illustrations showing the steps of deploying a surgical pleural decompression system according to another embodiment of the invention.
Figure 52B:
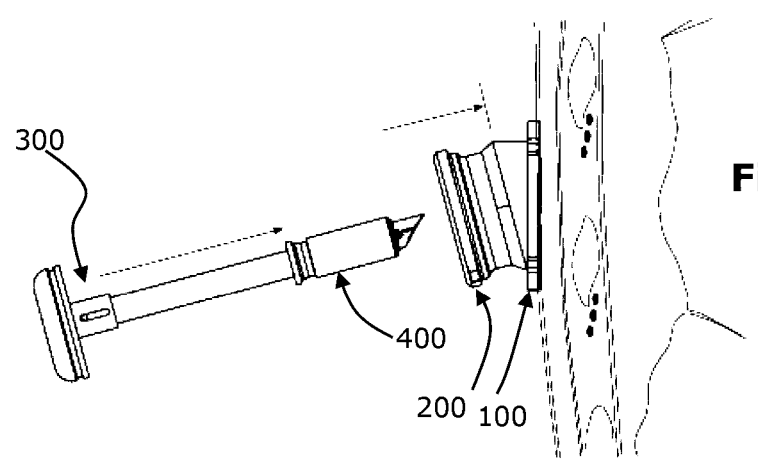
Figure 52C:
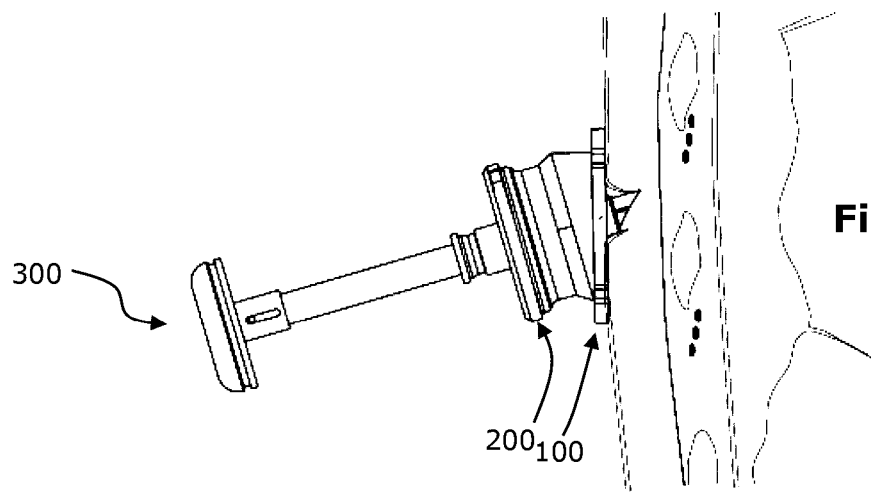
Figure 52D:
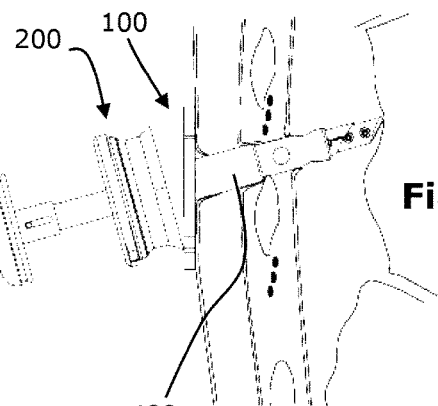
Figure 52E:
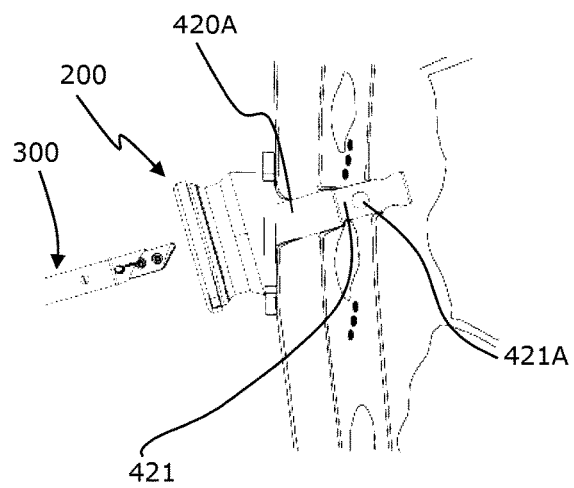
Figure 52F:
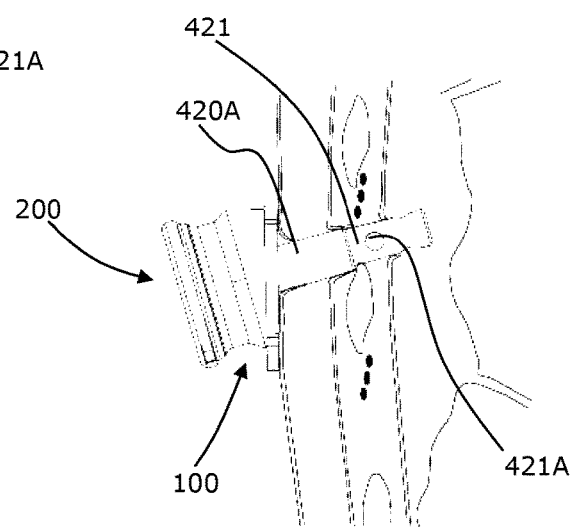
Figure 52G:
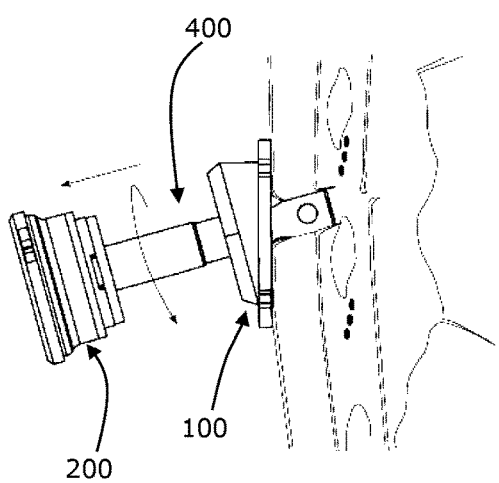

Referring to FIGS. 50 and 51, the process by which the cannula 400 with a telescopic body 420A is deployed by an obturator assembly 300 is illustrated. Firstly, cannula is inserted at the bottom end of the obturator assembly 300 and inserted through the valve assembly 200 and base 100. The cannula 400, together with the obturator assembly 300, passes through the valve assembly 200 and the cannula locks to the valve assembly 200 when the locking members 212 are coupled to the groove 412 of the cannula 400. The protruding ridge 336 of the obturator assembly 300 pushes against the seat 421B of the bottom-most cannula section 421 such that the cannula section 421 extends outwardly when the obturator assembly 300 is inserted/pushed further through the valve assembly 200 and the base 100. The telescopic body 420A can be fully extended in this manner as the obturator is pushed through the valve assembly 200. The cannula 400 with the telescopic body 420A will remain extended when the obturator assembly 300 is subsequently removed from the valve assembly 200. It is to be understood that while a three-staged telescopic cannula is shown in the Figures, preferred embodiments of the invention may have any suitable number of telescopic sections/stages.

Referring specifically to FIGS. 24 and 26, the protruding ridge 336 of the cutting portion 324 and/or the edges of the cannula anchoring portion 440 may be provide with radioactive strips or markers (see highlighted portions) to help the medical operator locate the relative positions the obturator assembly 300 and the cannula 400 with an x-ray device or similar during use.

Referring to FIGS. 34A to 34G, and 52A to 52G, a method of using the pleural decompression system 1 as described above for the treatment of tension pneumothorax is also provided. The method generally includes the following steps to be performed on the patient by a medical practitioner either in a clinical or hospital setting or during field use. The appropriate intercostal space should be identified using the mid-arm point method as described previously to locate a safe zone for performing pleural decompression on the patient. The base 100 is affixed on a patient above or adjacent the intercostal space of the pleural cavity by removing the protective peel 107 and mounting the adhesive 106 to the patient, while observing positional alignment using the rib alignment indicator 108 and orientation indicator 114, if available. Optionally, cardiac monitoring devices may be attached to the electrodes 122 to retrieve physical data from the patient. Remove the aperture cap 112 of the base 100 to expose the aperture 104, if available. Coupling the valve assembly 200 to the base 100 by pushing and clicking the valve assembly 200 into position, observing the alignment indicators if available.

Cutting through muscular tissues of the chest into the thoracic and pleural cavities with the cutting portion 324 of the obturator assembly 300 by inserting the obturator assembly 300 through the passage 221 of the valve assembly 200 and the plate aperture 104 (while observing any alignment indicators where available), and pushing the handle 310 of the obturator assembly 300 so that the cutting portion 324 cuts through the tissues 20. The blunt portion 323 of the obturator assembly 300 automatically extends past the cutting portion 324 through the pleural cavity to abut a lung portion with a loss of cutting pressure and locks the blunt portion 323 in the extended configuration relative to the cutting portion 324 to prevent visceral organ injury. The cannula 400 is then deployed into the pleural cavity 30 of the patient from the obturator assembly 300 by securing the locking portion 412 of the cannula 400 to the locking mechanism 210 of the valve assembly 200. It is to be appreciated that this step is done automatically by pushing the obturator assembly 300 through the valve assembly 200, as the cannula 400 is moving through the valve assembly 200. The anchoring portion 430 of the cannula 400 is pushed through the tissues along with the cutting portion 324 of the obturator assembly 300 and anchors to the chest wall 20 as shown in FIG. 34D. For cannula 400 with a telescopic body 420A, different telescopic sections 421 will extend from the cannula 400 through to the pleural cavity 30 with the bottom-most section 421 being extended by the insertion movement of the obturator assembly 300 first. Each telescopic section 421 stays extended and cannot be compressed as it is locked to the previous telescopic section 421 or telescopic body 420A as the obturator assembly 300 is removed. It is to be understood that due to self-locking configurations of the telescopic sections 421, an anchoring flange may not be required for use with the telescopic cannula.

Once the incision is complete, the obturator assembly 300 is removed by withdrawing the obturator assembly 300 from the valve assembly 200. Withdrawing the obturator assembly 300 automatically detaches the cannula 400 from the cutting portion 324 so that the lengthwise extendable cannula body 420 and distal portion 430 remains inside the chest tissues as shown in FIG. 34E, thereby facilitating a path for pleural fluid extraction into the valve assembly 200.

An external fluid extracting device can then be attached to the valve assembly 200 to extract fluid from the pleural cavity. The transparent housing 202 of the valve assembly 200 allows the medical practitioner to readily see the properties of the fluid being extracted. The flow indicator 224 is also useful in helping the practitioner determine the presence of extracted gas in the valve assembly 200.

Although the steps described above are provided in a specific order, it can be performed in any variation of this order and additional steps may be executed between the steps described above.

While the surgical system 1 has been described to be used deployed above or adjacent the intercostal space for pleural decompression in the treatment of simple and tension pneumothorax, it is to be understood that substantially the same surgical system 1 is also suitable, with little or no modifications required, for use in other surgical applications to establishing and maintaining a percutaneous cannula to an anatomical space (for example a body cavity) to permit controlled passage of fluids between the anatomical space and the valve and the external environment, with non-limiting examples including:

access to the trachea via cricothyroid membrane or sternal notch (for the treatment of emergency cricothyroidotomy, that is for emergency access to a patient's trachea to ventilate the lungs in the event of inability in accessing the trachea through the mouth or nasal passages);

suprapubic access to the bladder in patients in acute urinary retention (for the treatment of an obstructed urethra); and access to the peritoneum via the abdominal wall and access to the extradural space via the cranium.

Referring to FIGS. 35 to 39, the surgical system 1 can be substantially applied for accessing the trachea 510. In use, the base 100 is placed externally above or adjacent the cricothyroid membrane 500 located between the cricoid cartilage 512 and the thyroid cartilage 504 and deployed substantially as previously described. A suitable strap 130 is attached to the base 100 and looped around the neck of the patient to further secure the base in base. In one embodiment, the strap 130 is fed through apertures of the side portions 120 and tightened with a suitable buckle device. The valve assembly 200 is then coupled to the base 100 as previously described. A ventilator connector or port 260 is provided to be secured to the valve assembly 200 (for example with the coupler 230) for connection with a ventilator. This allows the patient to breathe while the surgical system 1 is deployed. In another embodiment, the valve assembly 200 is provided with a side access connector or port 250 for connection with a ventilator (not shown). The connector or port may be 15 mm in diameter. The obturator assembly 300 and the cannula 400 are then deployed substantially as previously described to provide access to the trachea 510 of the patient, with the anchoring portion 440 of the cannula 400 anchored to an anatomical part in the form of the cricothyroid membrane 500. The obturator assembly 300 can be removed substantially as previously described to leave the cannula 400 providing a conduit between the trachea 510 and the valve assembly 200. The valve assembly 200 and the cannula 400 can be subsequently removed substantially as previously described, by rotating the valve anti-clockwise and pulling the units out from the base 100.

Figure 41:
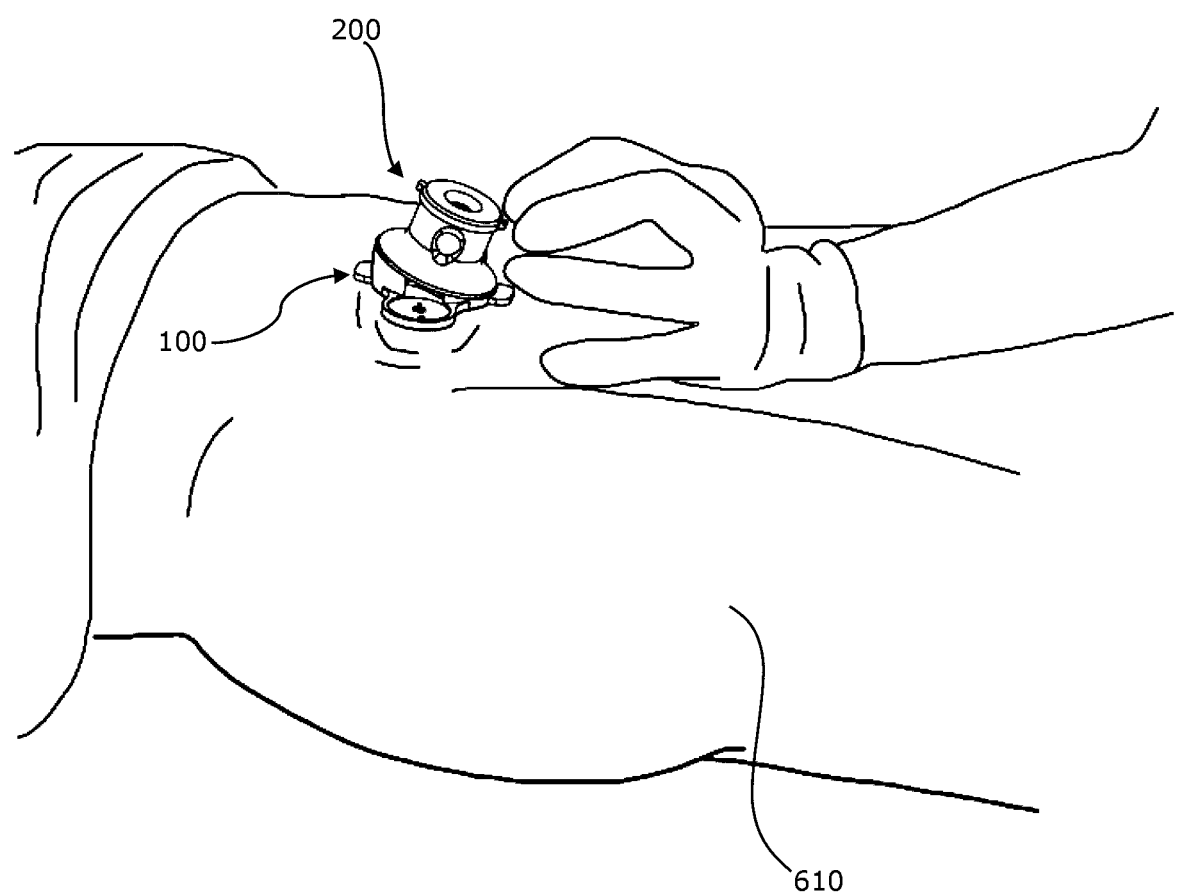
FIG. 41 is a perspective schematic illustration showing a surgical system according to an embodiment of the invention for use in treating obstructed urethra.
Figure 42:
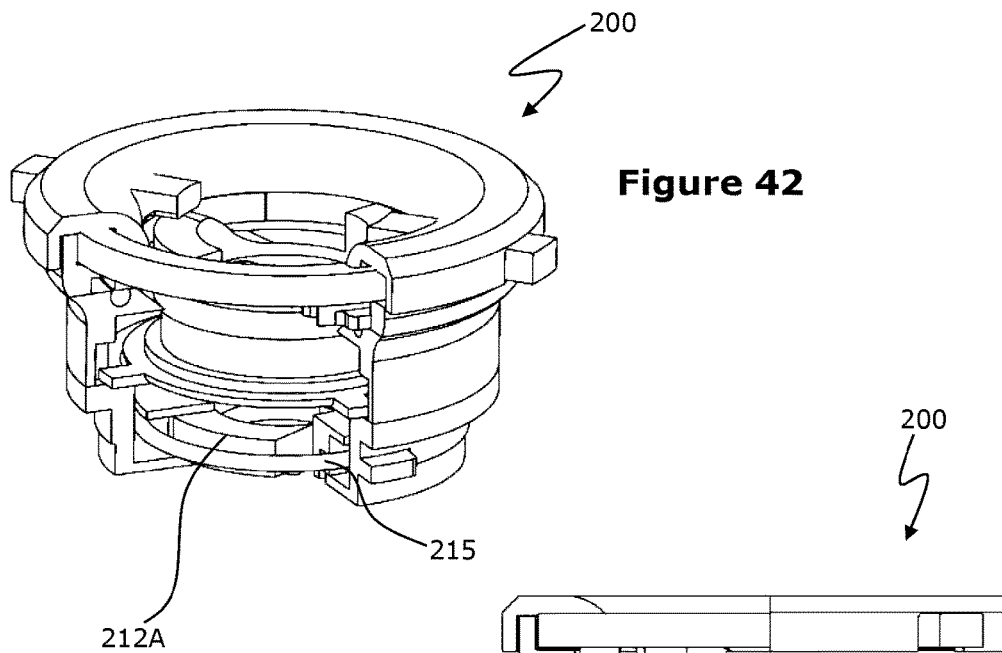
FIG. 42 is a rendered perspective view showing a valve assembly in accordance with another embodiment of the invention.
Figure 43:
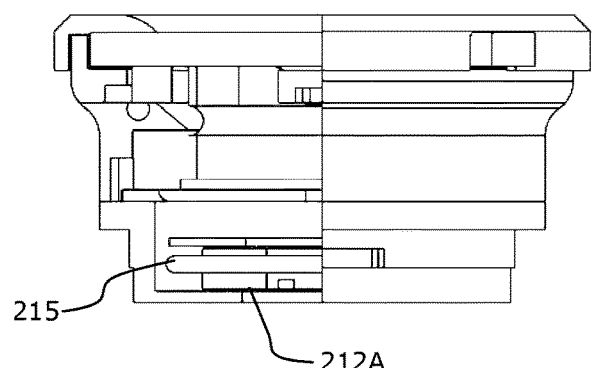
FIG. 43 is a rendered side view of the valve assembly of FIG. 42.

Referring to FIGS. 40 to 41, the surgical system 1 can be substantially applied for access to the bladder 600 of a patient for the treatment of an obstructed urethra. In use, a medical practitioner would deploy the base 100 externally above or adjacent a pubic symphysis area of the patient (see FIGS. 40A to 40E). The valve assembly 200 can then be coupled and the obturator assembly 300 and cannula 400 deployed substantially as previously described, with the anchoring portion 440 of the cannula 400 anchored to an anatomical part in the form of the upper wall of the bladder 600. A catheter can then be fed through the module into the bladder.

Preliminary experimentation results are provided below:

Experimentations have been conducted on the background that Tension Pneumothorax (tPTX) remains a serious and life threatening condition if left untreated. An investigation into the concerns associated with tPTX treatment and current challenges from utilising conventional techniques highlight the importance of developing alternative methods. The existing practices may be appealing in its simplicity and time to perform, yet they continued to be scrutinised for their failure rates and limited set of replicable data in support of their effectiveness. Consequently, an error-free device that can simultaneously address and correct the main issues regarding device placement, cannula length and obturator length, will form the basis for a breakthrough in treating thoracic trauma.

Tests have been conducted in relation to developing an experimental swine model of tPTX to allow SaPD pilot-testing and validation, testing in-vitro prototype SaPD devices against the conventional needle thoracostomy for pleural decompression and to standardize the insertion technique; and lastly, to verify any modifications required prior to in-vivo deployment where a reduction in the complications associated with pleural decompression is improved along with improved outcomes.

In conclusion, the SaPD device presents a valuable and effective treatment for the pre-hospital and clinical treatment of tPTX. This concept aimed to target the multiple aspects leading to the failure of pleural decompression. The cannula does not only contain the capacity to withstands the release of high pressured air, but is also rigid enough to prevent kinking without causing injury, an aspect identified to be lacking in current therapies. Furthermore, the obturator component involving the deployment of the blunt tip was created to reduce the risks associated with blind insertion of tPTX treatments. With the growing numbers of trauma incidences each year, the appreciation for a device that can fit all patient body types will immensely benefit the trauma management of tPTX.

It will be understood that the invention disclosed and defined in this specification extends to all alternative combinations of two or more of the individual features mentioned or evident from the text or drawings. All of these different combinations constitute various alternative aspects of the invention.

In the description and drawings of this embodiment, same reference numerals are used as have been used in respect of the first embodiment, to denote and refer to corresponding features.

While various embodiments of the present invention have been described above, it should be understood that they have been presented by way of example only, and not by way of limitation. It will be apparent to a person skilled in the relevant art that various changes in form and detail can be made therein without departing from the spirit and scope of the invention. Thus, the present invention should not be limited by any of the above described exemplary embodiments.

The claims defining the invention are as follows:

1. A pleural decompression system for use in the treatment of simple and/or tension pneumothorax, the system comprising:
    an obturator assembly having a cutting portion at a distal end, a cannula, and a deployable blunt portion, the cannula being detachably coupled to the cutting portion and deployable along with the blunt portion into a pleural space of a patient, the cannula comprises a locking portion, and a lengthwise collapsibly extendable body;
    a valve assembly comprising a passage for receiving the cannula, a first end for coupling to a fluid extraction device and a second end for placement above an intercostal space;
    a base comprising a plate for placement on the patient above the intercostal space, the plate has an aperture configured for receiving the obturator assembly and coupling means located about the aperture for coupling with the valve assembly; and
    wherein, in use, the locking portion of the cannula is configured to be retained in the valve assembly with the extendable body extended into a chest wall of the patient to facilitate a path for pleural fluid extraction, and wherein the cannula comprises means for retaining the cannula in an extended state.

2. A system according to claim 1, wherein the cannula is configured to have a minimum length of about 4 cm and a maximum length of about 9 cm.

3. A system according to claim 1, wherein a coiled spring is mounted around the cannula body to provide a bias around the body to move towards an extended configuration.

4. A system according to claim 3, wherein the means for retaining the cannula in the extended state comprises an anchoring portion located at a distal end of the cannula.

5. A system according to claim 4, wherein the anchoring portion is in the form of a helical flange.

6. A system according to claim 5, wherein the helical flange is operable between an anchoring configuration in which the flange is collapsed in the longitudinal direction, and an extraction configuration in which the flange is extended in the longitudinal direction.

7. A system according to claim 1, wherein the cannula comprises two or more telescopic sections extendable from the cannula body.

8. A system according to claim 7, wherein the means for retaining the cannula in the extended state comprises locking means for locking each of the two or more telescopic sections in an extended state when the cannula is in the extended state.

9. A system according to claim 1, wherein the coupling means is configured to receive the valve assembly at an angle inclined to an axis perpendicular to the plane of the plate.

10. A system according to claim 1, further comprising an indicator extending from the plate for assisting a user with placement of the plate above the intercostal space.

11. A system according to claim 1, further comprising a pair of side portions extending in directions opposite to each other from the plate for stabilising the plate from movement when secured to the patient.

12. A system according to claim 1, further comprising an electrode embedded in the plate configured for outputting physiological data to an external monitoring device.

13. A system according to claim 1, wherein the valve assembly comprises a one-way efflux valve.

14. A system according to claim 1, wherein the first end of the valve assembly is configured to receive a cap for coupling with the fluid extraction device.

15. A system according to claim 1, wherein the obturator assembly comprises a hollow stem and the cutting portion being located at the distal end of the stem.

16. A system according to claim 15, wherein the obturator assembly further comprises a spring-loaded inner stylet housed within the stem and movable relative to the stem, the stylet having a handle located at a proximate end and the blunt portion, the blunt portion being located at the distal end of the stem, wherein the obturator assembly is configured to operate between a retracted cutting configuration in which the blunt portion of the stylet is received within the stem to expose the cutting portion and an extended configuration in which the blunt portion extends past the cutting portion.

17. A system according to claim 16, wherein the obturator assembly is configured with locking means to hold the stem and stylet in the cutting and extended configurations.

18. A system according to claim 17, wherein the locking means comprises one or more complementary protrusion and aperture formations on the stem and the stylet.

19. A system according to claim 16, wherein the obturator assembly transforms from the cutting configuration to the extended configuration by a user pushing the stylet handle such that the blunt portion extends past the cutting portion and the locking engages the stylet in the extended configuration.

20. A system according to claim 1, wherein the cutting portion comprises a cutting blade having a chamfered tip.

21. A method of extracting fluid from a pleural cavity of a patient using a pleural decompression system in the treatment of simple and/or tension pneumothorax, the method comprising the steps of:
affixing a base comprising a plate on a patient above an intercostal space of the pleural cavity, the plate having an aperture configured for receiving an obturator assembly and coupling means located about the aperture for coupling with a valve assembly;
coupling the valve assembly to the base, the valve assembly comprising a passage for receiving a cannula and an open end for coupling to a fluid extraction device;
cutting through muscular tissues into the pleural cavity with a cutting portion of the obturator assembly by inserting the obturator assembly through the valve assembly passage and the plate aperture, and pushing a handle of the obturator assembly so that the cutting portion cuts through the tissues, a blunt portion of the obturator assembly automatically extends past the cutting portion with a loss of cutting pressure and locks the blunt portion relative to the cutting portion to prevent visceral organ injury;
deploying the cannula into the pleural cavity from the obturator assembly by securing a locking portion of the cannula to the valve assembly and removing the obturator assembly, the cannula further comprises a lengthwise extendable body extendable into a chest wall of the patient to facilitate a path for pleural fluid extraction into the valve assembly, the cannula having means for retaining the cannula in an extended state, in use;
extracting fluid from the pleural cavity by coupling the fluid extraction device to the valve assembly;
locating a mid-point of an upper arm of the patient between the olecranon and the acromion when the patient is in a supine position and the elbow of the patient is flexed to 90 degrees with the patient's forearm in a mid prone position;
projecting a line, perpendicular to the upper arm, from the mid-point of the upper arm across to the torso of the patient; and
marking the area of contact between the projecting line and the torso as a safe zone for performing pleural decompression procedures.

22. A method according to claim 21, wherein the cannula is configured to have a minimum length of about 4 cm and a maximum length of about 9 cm.

23. A method according to claim 21, wherein a coiled spring is mounted around the cannula body to provide a bias around the body to move towards an extended configuration.

24. A system according to claim 21, wherein the cannula comprises two or more telescopic sections extendable from the cannula body.

* * * * *